United States Patent
Keller et al.

(10) Patent No.: US 9,745,553 B2
(45) Date of Patent: *Aug. 29, 2017

(54) MESODERM AND DEFINITIVE ENDODERM CELL POPULATIONS

(71) Applicant: Icahn School of Medicine at Mount Sinai, New York, NY (US)

(72) Inventors: Gordon Keller, Toronto (CA); Paul Gadue, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/067,728

(22) Filed: Mar. 11, 2016

(65) Prior Publication Data

US 2016/0186134 A1    Jun. 30, 2016

Related U.S. Application Data

(63) Continuation of application No. 14/468,211, filed on Aug. 25, 2014, now abandoned, which is a
(Continued)

(51) Int. Cl.
   *C12N 5/00*  (2006.01)
   *C12N 5/071*  (2010.01)
   (Continued)

(52) U.S. Cl.
   CPC ......... *C12N 5/067* (2013.01); *C12N 5/0603* (2013.01); *C12N 5/0606* (2013.01); *C12N 5/0607* (2013.01); *C12N 2500/90* (2013.01); *C12N 2501/11* (2013.01); *C12N 2501/115* (2013.01); *C12N 2501/12* (2013.01); *C12N 2501/148* (2013.01); *C12N 2501/155* (2013.01);
   (Continued)

(58) Field of Classification Search
   CPC ..... C12N 5/067; C12N 5/0603; C12N 5/0607
   See application file for complete search history.

(56) References Cited

U.S. PATENT DOCUMENTS

| 4,997,815 A | 3/1991 | Perrine et al. |
| 5,283,168 A | 2/1994 | Nelson et al. |

(Continued)

FOREIGN PATENT DOCUMENTS

| EP | 1 319 708 A2 | 6/2003 |
| WO | 01/53465 A1 | 7/2001 |

(Continued)

OTHER PUBLICATIONS

Brink (Cells Tissues Organs, 2008, vol. 188, p. 9-22).
(Continued)

*Primary Examiner* — Marcia S Noble
(74) *Attorney, Agent, or Firm* — Fox Rothschild LLP

(57) ABSTRACT

The present invention provides cell populations that are enriched for mesendoderm and mesoderm, and cell populations that are enriched for endoderm. The cell populations of the invention are useful for generating cells for cell replacement therapy. The present invention further provides a method of generating hepatocytes, cell populations enriched for hepatocytes, and a method of hepatocyte replacement therapy.

14 Claims, 44 Drawing Sheets

Related U.S. Application Data continuation of application No. 13/646,995, filed on Oct. 8, 2012, now Pat. No. 8,815,591, which is a continuation of application No. 11/993,432, filed as application No. PCT/US2006/024462 on Jun. 23, 2006, now Pat. No. 8,283,168, which is a continuation of application No. 11/165,930, filed on Jun. 24, 2005, now abandoned.

(51) Int. Cl.
| | | |
|---|---|---|
| C12N 5/073 | (2010.01) | |
| C12N 5/0735 | (2010.01) | |
| C12N 5/074 | (2010.01) | |

(52) U.S. Cl.
CPC .... *C12N 2501/16* (2013.01); *C12N 2501/385* (2013.01); *C12N 2501/40* (2013.01); *C12N 2501/415* (2013.01); *C12N 2506/02* (2013.01); *C12N 2506/03* (2013.01)

(56) References Cited

U.S. PATENT DOCUMENTS

| | | | |
|---|---|---|---|
| 5,563,059 | A | 10/1996 | Alak et al. |
| 6,432,673 | B1 | 8/2002 | Gao et al. |
| 6,908,764 | B2 | 6/2005 | Czichos et al. |
| 7,326,572 | B2 | 2/2008 | Fisk et al. |
| 7,763,466 | B2 | 7/2010 | Keller et al. |
| 8,748,171 | B2 | 6/2014 | Keller et al. |
| 8,815,591 | B2 | 8/2014 | Keller et al. |
| 2002/0146678 | A1* | 10/2002 | Benvenisty .......... C12N 5/0603 435/4 |
| 2003/0003573 | A1 | 1/2003 | Rambhatle et al. |
| 2003/0027331 | A1 | 2/2003 | Yan et al. |
| 2003/0109035 | A1 | 6/2003 | Asashima et al. |
| 2004/0121464 | A1 | 6/2004 | Rathjen et al. |
| 2005/0054102 | A1 | 3/2005 | Wobus et al. |
| 2006/0003446 | A1 | 1/2006 | Keller et al. |

FOREIGN PATENT DOCUMENTS

| | | |
|---|---|---|
| WO | 02/29012 A1 | 4/2002 |
| WO | 03/083088 A2 | 10/2003 |
| WO | 2005063971 A2 | 7/2005 |
| WO | 2005/097980 A2 | 10/2005 |
| WO | 2005097990 A1 | 10/2005 |

OTHER PUBLICATIONS

Stem Cells: Scientific Progress and Future Research Directions. Department of Human Services. Jun. 2001. Chapter 4: The Adult Stem Cell., pp. 23-42.
Kubo, et al., Development of Definitive Endoderm From Embryonic Stem Cells in Culture Development and Disease, Mar. 2004, vol. 13, No. 7, pp. 1651-1662, pulbished by the Company of Biologists 2004.
Weinstein et al, The winged-helix transcription factor HNF-3beta is required for notochord development in the mouse embryo, Cell 1994, vol. 78, pp. 575-588.
Gamer et al., Autonomous Endodermal Determination in Xenopus: Regulation of Expression of the Pancreatic Gene X1Hbox 8, (Dev. Biol., 1995, vol. 171, pp. 240-241).
Boucher et al., (2000) Int. J. Dev. Biol, vol. 44, pp. 279-288.
Kispert et al., (1993) The EMBO Journal, vol. 12; pp. 3211-3220.
Reyes et al., (2001) Blood, vol. 98, pp. 2615-2625.
Tada et al., (2005) Development, vol. 132, pp. 4363-4374.
Wiles et al., (1999) Experimental Cell Research, vol. 247; pp. 241-248.
Muhr et al., "Assignment of Early Caudal Identity to Neural Plate Cells by a Signal from Caudal Paraxial Mesoderm,", Neuron, vol. 19, pp. 487-502, Sep. 1987.
Rodaway et al., "Induction of the mesendoderm in the zebrafish germ ring by yolk cell-derived TGF-β family signals and discrimination of mesoderm and endoderm by FGF", Development vol. 126, pp. 3067-3078 (1999), Printed in Great Britain.
Slager et al., "Secretion of Transforming Growth Factor-β Isoforms by Ebryonic Stem Cells: Isoform and Latency Are Dependent on Direction of Differentiation", Journal of Cellular Physiology, vol. 156, pp. 247-256, (1993).
Brachyury, JCLS, vol. 43, No. 10, pp. 1347-1354; 1420, Aug. 1998, Printed in Japan.
Wilson et al., Chimeric analysis of T (Brachyury) gene function, Development, vol. 117, pp. 1321-131 (1993), Printed in Great Britain.
Fehling et al. (2003) Development 130:4217-4227.
Rambhatle et al. (2003) Cell Transplantation 12:1-11.
Yasunaga et al. (2005) Nature Biotechnology 23:1542-1550.
Conquet. Neuropharmacology 34(8):865-870, 1995.
Mao et al. Blood 97:324-326, 2001.
Schuldiner (PNAS, Oct. 10, 2000, vol. 97, No. 21, p. 11307-11312).
Takahashi et al. (1998) Protein, Nucleic Acid and enzyme 43:1347-1354.
Lagasse et al. (2000) Nature Medicine 6:1229-1234.
Asashima et al., Transplantation Now, 2000, 13: 330-336.
Edwards et al., Genome Res., 1996, 6: 226-233.
Eiges et al., Current Biol., 2001, 11: 514-518.
Guan et al., Cytotechnology, 1996, 30: 211-226.
Hamazaki et al., FEBS Lett., 2001, 497: 15-19.
Kimelman et al., Curr.Opin.Genetics Dev., 2000, 10: 350-356.
Davis et al., Blood, 2008, 111: 1876-1884.
Hockemeyer et al., Nature Biotechnology, 2009, 27: 851-858.
Urbach et al., Stem Cells, 2004, 22: 635-641.
Zou et al., Cell Stem Cell, 2009, 5: 97-110.
Zwaka et al., Nature Biotechnology, 2008, 21: 319-321.
Assady et al. "Insulin Production by Human Embryonic Stem Cells." Diabetes 50: 1691-1697. (Aug. 2001).
Davidson et al. "Exogenous FGF-4 Can Suppress Anterior Development in the Mouse Embryo during Neurulation and Early Organogenesis." Developmental Biology 221: 41-52. (2000).
Ito et al., Cultivation of hepatitis C virus in primary hepatocyte culture from patients with chrinic hepatitis C results in release of high titre infectious virus, Journal of General Virology 77:1043-1054, 1996.
Smith, A. G., "Embryo-Derived Stem Cells: Of Mice and Men", Annu. Rev. Cell Dev. Biol. 17: 435-462. (2001).
Ang, et al. "The formation and maintenance of the definitive endoderm lineage in the mouse: involvement of the HNF3/forkhead proteins." Development 119: 1301-1315. (1993).
Srinivas, et al. Cre reporter strains produced by targeted insertion of EYFP and ECFP into the ROSA26 locus. BMC Development (2001) 1:4. <<http://www.biomedcentral.com/1471-213X/1/4>> Last accessed Dec. 20, 2007.
Abe, et al. Molecular and Embryological Characterization of a New Transgene-induced Null Allele of Mouse Brachyury Locus. Mammalian Genome 11: 238-240. (2000).
Ansari-Lari, et al. A gene-rich cluster between the CD4 and triosephosphate isomerase genes at human chromosome 12p13. Genome Research 5(4): 314-326. (1996).
Johansson, et al. Evidence for involvement of Activin A and Bone Morphogenetic Protein 4 in Mammalian Mesoderm and Hematopoietic Development. Molecular and Cellular Biology 15(1): 141-151. (1995).
Dellow, et al. Identification of novel cardiac-restricted transcription factors binding to a CACC-box within the human cardiac troponin I promoter. Cardiovascular Research 50: 24-33. (2001).
Clozel, et al. Specific Binding of Endothelin on Human Vascular Smooth Muscle Cells in Culture. J. Clin. Invest. 83: 1756-1761. (1989).
Abe et al., Endoderm-speclfic Gene Expression in Embryonic Stem Cells Differentiated to Embryoid Bodies. Exp Cell Res., Nov. 1996, vol. 229, No. 1, pp. 27-34.
Keller et at, "Hematopoietic Commitment During Embryonic Stem Cell Differentiation in Culture" Jan. 1993. Molecular and Cellular Biology, vol. 13, No. 1, pp. 473-486.

(56) References Cited

OTHER PUBLICATIONS

Rodaway et al., Mesendoderm: An Ancient Germ Layer, Cell, vol. 105, pp. 169-172, Apr. 20, 2001.
Rashbass et al. Nature 353:348-351, Sep. 26. 1991.

* cited by examiner

GFP-Bry (+)

GFP-Bry (-)

SEQUENCE LISTING

<160> NUMBER OF SEQ ID NOS: 15

<210> SEQ ID NO 1
<211> LENGTH: 40
<212> TYPE: DNA
<213> ORGANISM: artificial
<220> FEATURE:
<223> OTHER INFORMATION: Synthetic

<400> SEQUENCE: 1
gttaactcga gaattctttt tttttttttt tttttttttt          40

<210> SEQ ID NO 2
<211> LENGTH: 32
<212> TYPE: DNA
<213> ORGANISM: artificial
<220> FEATURE:
<223> OTHER INFORMATION: Synthetic

<400> SEQUENCE: 2
tggagtcaaa gagggcatca tagacacatg gg          32

<210> SEQ ID NO 3
<211> LENGTH: 24
<212> TYPE: DNA
<213> ORGANISM: artificial
<220> FEATURE:
<223> OTHER INFORMATION: Synthetic

<400> SEQUENCE: 3
cagtacactg gccaatccca tgtg          24

<210> SEQ ID NO 4
<211> LENGTH: 23
<212> TYPE: DNA
<213> ORGANISM: Mus musculus

<400> SEQUENCE: 4
aaggagctaa ctaacgagat gat          23

<210> SEQ ID NO 5
<211> LENGTH: 21
<212> TYPE: DNA
<213> ORGANISM: Mus musculus

<400> SEQUENCE: 5
taccttcagc accgggaaca t          21

<210> SEQ ID NO 6
<211> LENGTH: 17
<212> TYPE: DNA
<213> ORGANISM: artificial
<220> FEATURE:
<223> OTHER INFORMATION: Synthetic

<400> SEQUENCE: 6
gctagctaat ggatcca          17

<210> SEQ ID NO 7
<211> LENGTH: 25
<212> TYPE: DNA
<213> ORGANISM: artificial
<220> FEATURE:
<223> OTHER INFORMATION: Synthetic

<400> SEQUENCE: 7

```
gatctggatc cattagctag ctgca                                         25

<210> SEQ ID NO 8
<211> LENGTH: 36
<212> TYPE: DNA
<213> ORGANISM: artificial
<220> FEATURE:
<223> OTHER INFORMATION: Synthetic

<400> SEQUENCE: 8
gatcttaatg aacggcaggt gggtgcgcgt ccggag                             36

<210> SEQ ID NO 9
<211> LENGTH: 36
<212> TYPE: DNA
<213> ORGANISM: artificial
<220> FEATURE:
<223> OTHER INFORMATION: Synthetic

<400> SEQUENCE: 9
tcgactccgg acgcgcaccc acctgccgtt cattaa                             36

<210> SEQ ID NO 10
<211> LENGTH: 21
<212> TYPE: DNA
<213> ORGANISM: artificial
<220> FEATURE:
<223> OTHER INFORMATION: Synthetic

<400> SEQUENCE: 10
cgcgttacta gtaagacgtc t                                             21

<210> SEQ ID NO 11
<211> LENGTH: 21
<212> TYPE: DNA
<213> ORGANISM: artificial
<220> FEATURE:
<223> OTHER INFORMATION: Synthetic

<400> SEQUENCE: 11
ccggagacgt cttactagta a                                             21

<210> SEQ ID NO 12
<211> LENGTH: 23
<212> TYPE: DNA
<213> ORGANISM: artificial
<220> FEATURE:
<223> OTHER INFORMATION: Synthetic

<400> SEQUENCE: 12
caggtagaac ccacaactcc gac                                           23

<210> SEQ ID NO 13
<211> LENGTH: 22
<212> TYPE: DNA
<213> ORGANISM: artificial
<220> FEATURE:
<223> OTHER INFORMATION: Synthetic

<400> SEQUENCE: 13
ccggacacgc tgaacttgtg gc                                            22

<210> SEQ ID NO 14
<211> LENGTH: 30
<212> TYPE: DNA
```

```
<213> ORGANISM: artificial
<220> FEATURE:
<223> OTHER INFORMATION: Synthetic

<400> SEQUENCE: 14
acaggatccc taagcctcaa aagagtcgct                              30

<210> SEQ ID NO 15
<211> LENGTH: 33
<212> TYPE: DNA
<213> ORGANISM: artificial
<220> FEATURE:
<223> OTHER INFORMATION: Synthetic

<400> SEQUENCE: 15
tcttggatcc tcctatccta tcccgaagct cct                          33
```

MESODERM AND DEFINITIVE ENDODERM CELL POPULATIONS

CROSS-REFERENCE TO RELATED APPLICATION

This application is a Continuation of U.S. patent application Ser. No. 14/468,211, filed on Aug. 25, 2014, which is a Continuation of U.S. patent application Ser. No. 13/646,995, now U.S. Pat. No. 8,815,591, filed Oct. 8, 2012, which is a Continuation of U.S. patent application Ser. No. 11/993,432, now U.S. Pat. No. 8,283,168, having a 371(c) filing date of Jan. 21, 2010, which is the U.S. National Phase of International Patent Application Serial No. PCT/US2006/024462, filed Jun. 23, 2006, which claims priority to U.S. patent application Ser. No. 11/165,930, filed Jun. 24, 2005, now abandoned. The contents of the foregoing applications are hereby incorporated by reference in their entireties.

STATEMENT REGARDING FEDERALLY SPONSORED RESEARCH

This invention was made with government support under Grant Nos. 2RO1 HL 48834-09 and 2RO1 HL 65169-02 awarded by the National Institutes of Health. The United States government has certain rights in the invention.

BACKGROUND OF THE INVENTION

During embryonic development, the tissues of the body are formed from three major cell populations: ectoderm, mesoderm and definitive endoderm. These cell populations, also known as primary germ cell layers, are formed through a process known as gastrulation. Following gastrulation, each primary germ cell layer generates a specific set of cell populations and tissues. Mesoderm gives rise to blood cells, endothelial cells, cardiac and skeletal muscle, and adipocytes. Definitive endoderm generates liver, pancreas and lung. Ectoderm gives rise to the nervous system, skin and adrenal tissues.

The process of tissue development from these germ cell layers involves multiple differentiation steps, reflecting complex molecular changes. With respect to mesoderm and its derivatives, three distinct stages have been defined. The first is the induction of mesoderm from cells within a structure known as the epiblast. The newly formed mesoderm, also known as nascent mesoderm, migrates to different positions that will be sites of future tissue development in the early embryo. This process, known as patterning, entails some molecular changes that are likely reflective of the initial stages of differentiation towards specific tissues. The final stage, known as specification, involves the generation of distinct tissues from the patterned mesodermal subpopulations. Recent studies have provided evidence which suggests that mesoderm is induced in successive waves which represent subpopulations with distinct developmental potential. The mesoderm that is formed first migrates to the extraembryonic region and gives rise to hematopoietic and endothelial cells, whereas the next population migrates anteriorly in the developing embryo and contributes to the heart and cranial mesenchyme. These lineage relationships were defined initially through histological analysis and have been largely confirmed by cell tracing studies. While this segregation of developmental fates is well accepted in the field of developmental biology, to date, there are no available methods of isolating mesoderm and endoderm, prior to commitment to these lineages.

The present invention provides a method for isolating mesoderm and definitive endoderm cell populations. These cell populations are useful to identify agents that affect cell growth and differentiation, to identify genes involved in tissue development, and to generate differentiated cells and tissues for cell replacement therapies.

SUMMARY OF THE INVENTION

The present invention provides cell populations that are enriched for mesendoderm and mesoderm cells. Mesendoderm cells are defined herein as cells that express brachyury (brach$^+$) and which, in the presence of differentiation-inducing conditions, are capable of generating mesoderm and mesoderm derivatives including cardiac and skeletal muscle, vascular smooth muscle, endothelium and hematopoietic cells, and also are capable of generating endoderm and endoderm derivatives including liver cells and pancreatic cells. Mesoderm cells are defined herein as cells that are brach$^+$ and which, in the presence of differentiation inducing conditions, are capable of generating cardiac and skeletal muscle, vascular smooth muscle, endothelium and hematopoietic cells, and are not capable of generating endoderm and endoderm derivatives.

The present invention further provides cell populations that are enriched for endoderm cells. Endoderm cells are defined herein as cells that do not express brachyury (brach)) and which, in the presence of differentiation-inducing conditions, are capable of generating lung cells, liver cells and pancreatic cells.

The present invention also provides methods of isolating cell populations enriched for mesendoderm and mesoderm cells, and cell populations enriched for endoderm cells. In another embodiment the present invention provides cell populations that are enriched for hepatocytes, and methods of making such populations.

In another embodiment, the invention provides a method of hepatocyte replacement therapy.

In another embodiment, the present invention provides methods of identifying agents that affect the proliferation, differentiation or survival of the cell populations of the invention. A method of identifying genes involved in cell differentiation and development of specific lineages and tissues is also provided.

Antibodies that specifically recognize brach cells are also provided. The antibodies are useful, for example, for isolating mesendoderm and mesoderm cell populations.

In another embodiment, the present invention provides a method for generating cells in vitro. Such cells are useful, for example, for cell replacement therapy.

The present invention also provides a transgenic non-human mammal having a genome in which DNA encoding a selectable marker is present in the brachyury locus such that one brachyury allele is inactivated and the selectable marker is expressed in cells in which the brachyury locus is transcribed.

BRIEF DESCRIPTION OF THE DRAWINGS

FIG. 2A depicts the kinetics of brachyury expression determined by reverse transcriptase-polymerase chain reaction (RT-PCR). FIG. 2B depicts the kinetics of GFP expression determined by fluorescence activated cell sorting (FACS) analysis. Numbers above the figure in FIG. 2A and the histograms in FIG. 2B represent day of EB differentiation.

FIG. 3A is a histogram showing developmental potential of day 6 EBs. (Mac/Ery: colonies of macrophages and definitive erythroid cells; Mac: pure macrophage colonies; $Ery^d$: colonies of definitive erythroid cells; Mix: multilineage colonies; $Ery^p$: primitive erythroid colonies. FIG. 3B is a histogram depicting blast colony-forming cell (BL-CFC) potential of EBs. FIG. 3C shows gene expression patterns during EB development for wild-type and GFP-Bry cells. Numbers at the top of the lanes represent day of EB differentiation.

FIG. 4A shows the profile of GFP expression in day 3.5 EBs. 1 and 2 represent the gates used to isolate the GFP$^-$ and GFP$^+$ fractions. FIG. 4B depicts RT-PCR expression analysis of isolated fractions.

FIG. 5A depicts the profiles and gates used to isolate the GFP$^-$/Flk-1$^-$, GFP$^+$/Flk-1$^-$ and GFP$^+$/Flk-1$^+$ fractions from day 3.0 and 3.5 EBs Numbers next to the gates represent the three different populations. FIG. 5B shows the Blast colony (Blast) and secondary EB)(2° potential of the different fractions. FIG. 5C shows the expression analysis of the isolated fractions. Expression shown in the top panel was evaluated using a polyA$^+$ global amplification PCR method described by Brady et al. (1990) Meth. In Mol. And Cell Bio. 2:17-25. The data in the lower panels was obtained by RT-PCR analysis using gene specific oligonucleotides. Numbers on the top of each row indicate the cell population as designated in FIG. 5A.

In FIG. 7A, the numbers on the bottom refer to the cell population: 1 is the presort, 3 is the GFP$^+$/Flk-1$^-$ fraction and 4 is the GFP$^+$/Flk-1$^+$ fraction. Cells were cultured for 20 hours, and the aggregates were then dissociated and analyzed for BL-CFC. Data are shown for cells isolated from day 3, 3.5 and 4.0 EBs. In FIG. 7B, the top row represents GFP$^+$/Flk-1$^-$ cells isolated from day 3.0, 3.5 and 4.0 EBs prior to culture (pre). The bottom row shows the Flk-1 expression pattern of the same fraction, following culture (post). Numbers above the bars represent the percentage of Flk-1$^+$ cells.

FIG. 8B depicts expression of brachyury and Flk-1 on cell populations generated from GFP+//Flk-1$^-$ cells cultured for 20 hours under the indicated conditions.

FIG. 30A depicts the scheme of the vector and strategy used for targeting CD4. FIG. 30B shows the southern blot of ES cell clones electroporated with the targeting vector.

FIG. 31A shows dot plots of GFP versus hCD4 expression determined by flow cytometric analysis. FIG. 31B shows the mean fluorescence intensity (MFI) of both GFP and hCD4 expression of the plots in part A. The MFI is displayed as a percent of maximum detected during the time course for each marker. FIG. 31C depicts the expression of Brachyury and HNF3β by RT PCR in the same samples used in part A for flow cytometry.

FIG. 32A shows dot plots of GFP versus hCD4 expression before and after cell sorting for these populations. GFP+ hCD4$^{lo}$, GFP+ hCD4$^{med}$, and GFP+ hCD4$^{hi}$ populations were sorted to the purity indicated. FIG. 32B shows expression of genes by RT PCR in the samples sorted in part A. FIG. 32C shows expression of genes by RT PCR in tissue dissected from the primitive streak dissected from day 7.25 embryos. Abbreviations used: Pre, presort; ant, anterior primitive streak tissue; mid, middle primitive streak tissue, pos, posterior primitive steak tissue.

FIG. 33A shows cardiac potential of the sorted populations after plating on matrigel another 24-48 hours. The percentage of EBs containing beating cells was calculated. FIG. 33B shows hematopoietic potential of the sorted populations determined by plating in methycelluose with hematopoietic cytokines. FIG. 33C shows expression of endodermal genes by RT PCR of the sorted populations after plating on matrigel for an additional 5 days in serum free media.

FIG. 34A shows dot plots of GFP versus hCD4 expression for days 3 through 6 with EBs that were reaggregated with media alone, Activin A 25 ng/ml, Wnt3a 100 ng/ml, or these stimulations plus either DKK1 100 ng/ml or SB-431542 6 uM. FIG. 34B shows RT PCR gene expression data from RNA obtained from cultures shown in FIG. 34A. FIG. 34C shows RT PCR gene expression data from RNA obtained from EBs plated on matrigel for an addition 6 days that had initially been stimulated with media alone, Activin or Wnt3a as indicated above.

FIG. 35A shows histograms for hCD4 and GFP expression of the sorted cells after 1 day reaggregation. FIG. 35B depicts endodermal gene expression by RT PCR. The sorted populations were treated as indicated above for 2 days, then plated on matrigel in serum free media without factors added. Gene expression was analyzed an additional 5 days after plating.

DETAILED DESCRIPTION OF THE INVENTION

Figure 1:
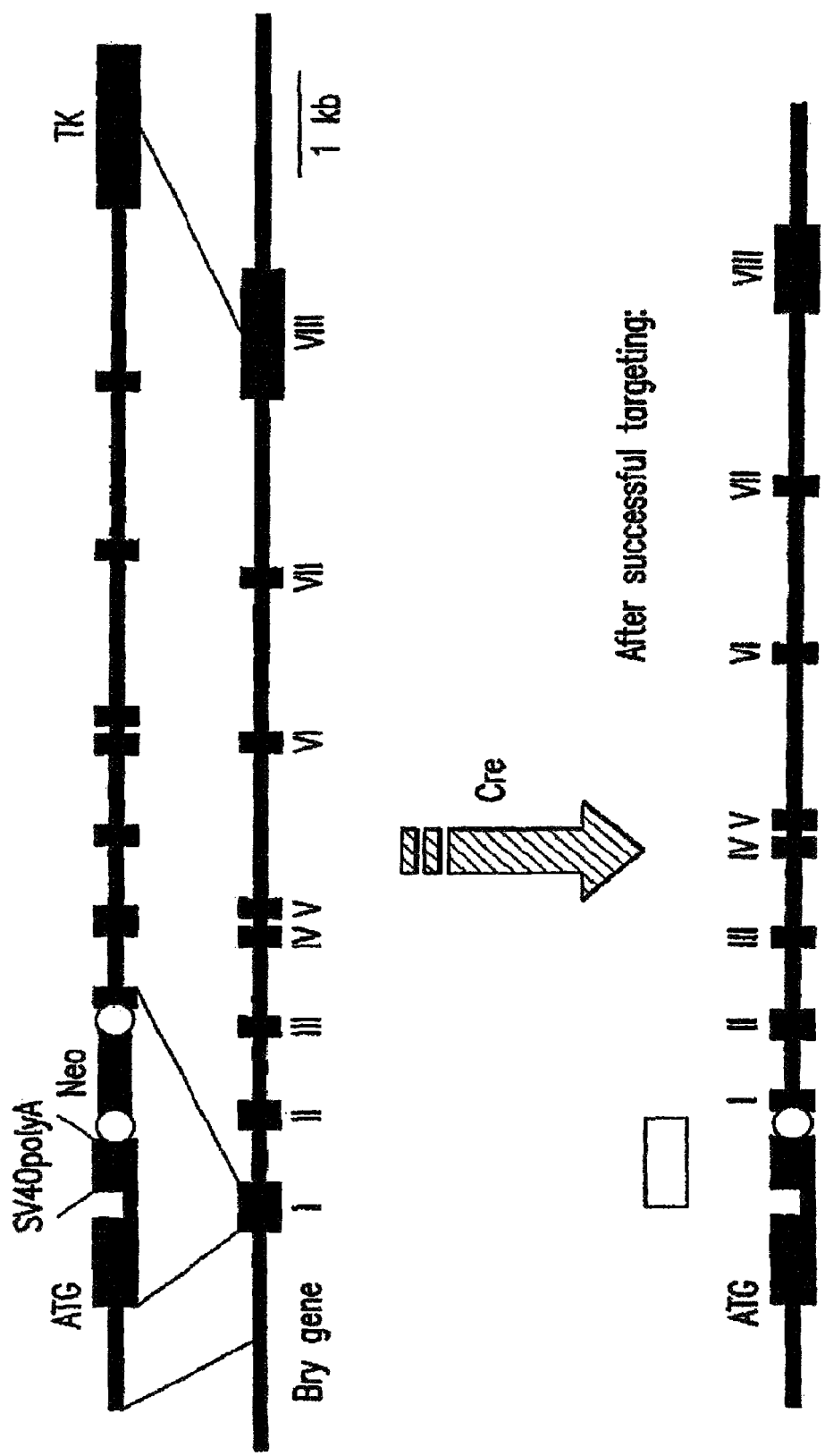
FIG. 1 depicts the scheme of the vector and the strategy used for targeting the green fluorescence protein (GFP) to the brachyury locus.

During embryogenesis, the formation of mesoderm is a critical step in the establishment of a body plan and in the development of multiple organ systems such as blood, endothelium, heart and skeletal muscle. The molecular mechanisms that control mesoderm formation, however, are poorly defined. A model system based upon the differentiation of embryonic stem (ES) cells in culture has been used to study mesodermal-derived populations including hematopoietic, endothelial, cardiac and skeletal muscle and adipocyte lineages. The in vitro model supports the induction and specification of mesoderm, but these differentiation events take place in complex colonies known as embryoid bodies (EBs) generated from ES cells. It would be advantageous to isolate mesoderm cell populations from EBs as they are formed, in order to better understand mesoderm formation and tissue development. However, it has not been possible to isolate these populations by cell sorting using antibodies, because antibodies specific for nascent mesoderm cell populations are not well-defined.

Brachyury (also known as T) is the founding member of a family of transcription factors known as T-box genes and was first identified as a naturally occurring mutation in mice. Papaioannou et al. (1998) Bioessays 20:9-19. Heterozygous mice are viable but have a shorter tail than wild type animals. Homozygous mutants, which die at approximately day 10 p.c, lack a notochord and display defects in the development of posterior mesodermal tissues. Through the analysis of chimeric animals, brachyury has been shown to affect the migratory properties of the mesodermal cells. Wilson et al. (1995) Development 121:877-86. Expression analysis revealed a unique and interesting pattern for brachyury. It is expressed transiently in all cells ingressing through the primitive streak as well as in the nascent and early migrating mesoderm. Wilkinson et al. (1990) Nature 343:657-9; Herrmann et al. (1991) Development 113:913-7. Expression is rapidly downregulated in paraxial, lateral and extraembryonic mesoderm and following regression of the steak, is confined to the tailbud and notochord. Given this pattern, brachyury is considered to be one of the best markers of early mesoderm and is used to track the development of this lineage. Brachyury has been identified in all species analyzed, suggesting that its role in mesoderm development is preserved throughout phylogeny. Papaioannou et al. (1998).

In accordance with the present invention, a selectable marker gene has been recombinantly targeted to the brachyury locus. It has been discovered that, following the initiation of ES cell differentiation, the selectable marker is expressed in a pattern that reflects brachyury expression. The selectable marker has allowed the sorting of brachyury positive (Brach$^+$) cells from EBs, and thereby the isolation and characterization of cell populations that are enriched for mesendoderm and mesoderm cells.

The selectable marker exemplified in accordance with the present invention is the enhanced green fluorescence protein (EGFP or GFP). Other selectable markers that will facilitate cell sorting are known to those of ordinary skill in the art and may be used in the present invention. The cDNA encoding GFP is known in the art (and is commercially available, for example as plasmid pEGFP.Cl from Clontech, Palo Alto, Calif.), and may be targeted to the brachyury locus by constructing targeting vectors (GFP-Bry) by methods known in the art. The vectors are preferably designed to replace approximately two-thirds of the first exon of the brachyury gene with a GFP expression cassette.

Brachyury genes from numerous species, including human and mouse, are known in the art and reviewed, for example, by Smith (1997) Current Opinion in Genetics & Development 7:474-480. The GFP expression cassette preferably contains GFP cDNA and one or more translational stop codons to prevent translation of downstream brachyury exons. The cassette may further contain an exon encoding the SV40 polyadenylation signal sequence to prevent transcription of downstream regions of the brachyury gene.

The vectors are introduced into ES cells by methods known in the art to integrate the GFP-Bry construct by homologous recombination. ES cells may be isolated from blastocysts by methods known in the art and disclosed for example by Evans et al. (1981) Nature 292:154-156, Thomson et al. (1995) Proc. Nat'l. Acad. Sci. USA 92; 7844; U.S. Pat. No. 5,843,780; and Reubinoff et al. (2000) Nature Biotech. 18:399. In a preferred embodiment the ES cells are mouse or human ES cells. Following successful targeting the brachyury start codon becomes the start codon of GFP, resulting in the disruption of the targeted brachyury allele. The resulting cells are designated GFP-Bry ES cells. GFP-Bry ES cells are defined herein as ES cells in which one brachyury allele is inactivated and GFP is expressed under the control of the brachyury regulatory elements.

It has been discovered in accordance with the present invention that GFP-Bry ES cells, in which one brachyury allele is inactivated, are viable and develop and differentiate normally. Further, it has been discovered that GFP expression mirrors endogenous brachyury expression. Accordingly, brach$^+$ cells may be isolated by selecting for cells that express GFP. Cells that express GFP may conveniently be isolated by flow cytometry, for example by fluorescence-activated cell sorting (FACS). Methods for sorting cells based on fluorescent properties are well-known to those of ordinary skill in the art.

The present invention also provides GFP-Bry ES cells that have a selectable marker gene recombinantly targeted to the HNF3β locus. HNF3β is known to be expressed in most endodermal cell types. HNF3β is also known as Foxa2, and these terms are used interchangeably herein. The marker allows the sorting of HNF3β+ cells. The marker exemplified in accordance with the present invention is a truncated human CD4 that lacks most of the intracellular domain. This cell surface molecule is preferred because it cannot transduce signals and antibodies are available for flow cytometry. Other markers that will facilitate cell sorting are known to those of ordinary skill in the art and may be used in the present invention. The cDNA encoding human DC4 is known in the art and may be targeted to the HNF3β locus by methods known in the art. A targeting vector having cDNA encoding the truncated human CD4 cloned between two arms of homology of HNF3β may be electroporated into GFP-Bry ES cells to provide CD4-HNF/GFP-Bry ES cells. The expression of human CD4 in these cells reflects endogenous expression of HNF3β.

Cell populations that are enriched for mesendoderm and mesoderm cells, as defined hereinabove, may be obtained by culturing GFP-Bry ES cells in the presence of serum for a time sufficient to obtain GFP$^+$ cells, for example for from about one to about four days for mouse cells, and sorting and isolating GFP$^+$ cells, for example by flow cytometry. The cell population that is isolated contains at least about 50%, and preferably at least about 75%, and more preferably at least about 90%, and most preferably at least about 95% or at least about 99% mesendoderm and mesoderm cells. The relative amounts of mesendoderm and mesoderm may be varied by adjusting the length of the culture in serum, with shorter culture times favoring the presence of mesendoderm and mesoderm patterned to the hematopoietic and endothelial lineages, and longer culture times favoring the presence of mesoderm patterned to the cardiac and skeletal muscle lineages. For example, a cell population enriched for mesoderm may be obtained by culturing in serum for about 2.5 to 4.5 days, followed by sorting and isolating GFP$^+$ cells. Culturing in the presence of serum is defined herein as culturing in media supplemented with animal serum, for example fetal calf serum (FCS). In a preferred embodiment, the media is supplemented with from about 5% to about 25% serum. The optimal concentration may be serum batch dependent and can be determined by one of ordinary skill in the art.

Cell populations that are enriched for mesendoderm and mesoderm cells may be obtained from GFP-Bry ES cells generated from human ES cells by a similar method in which the length of time of culture in serum is lengthened to account for difference in times of differentiation in vitro for human and mouse cells. Accordingly, GFP-Bry ES cells generated from human ES cells are cultured in serum for a time sufficient to obtain GFP$^+$ cells, for example about 2 to about 18 days, before sorting and isolating GFP$^+$ cells.

For both mouse and human cell populations, it can be easily determined whether the isolated cells have differentiated beyond mesoderm, for example to hemangioblasts, by assaying for the presence of the tyrosine kinase receptor, human KDR or mouse Flk-1. KDR and Flk-1 are not expressed in mesendoderm and nascent mesoderm, but as these cells differentiate to a hemangioblast/pre-erythroid population, KDR or Flk-1 expression is detectable. KDR$^+$ and Flk-1$^+$ cells may be identified by flow, cytometry using antibodies to KDR or Flk-1. Such antibodies are known in the art, and may also be generated using standard methods of antibody production. The cell populations enriched for mesendoderm and mesoderm may be further enriched by removing KDR or Flk-1+ cells by cell sorting.

Figure 17:
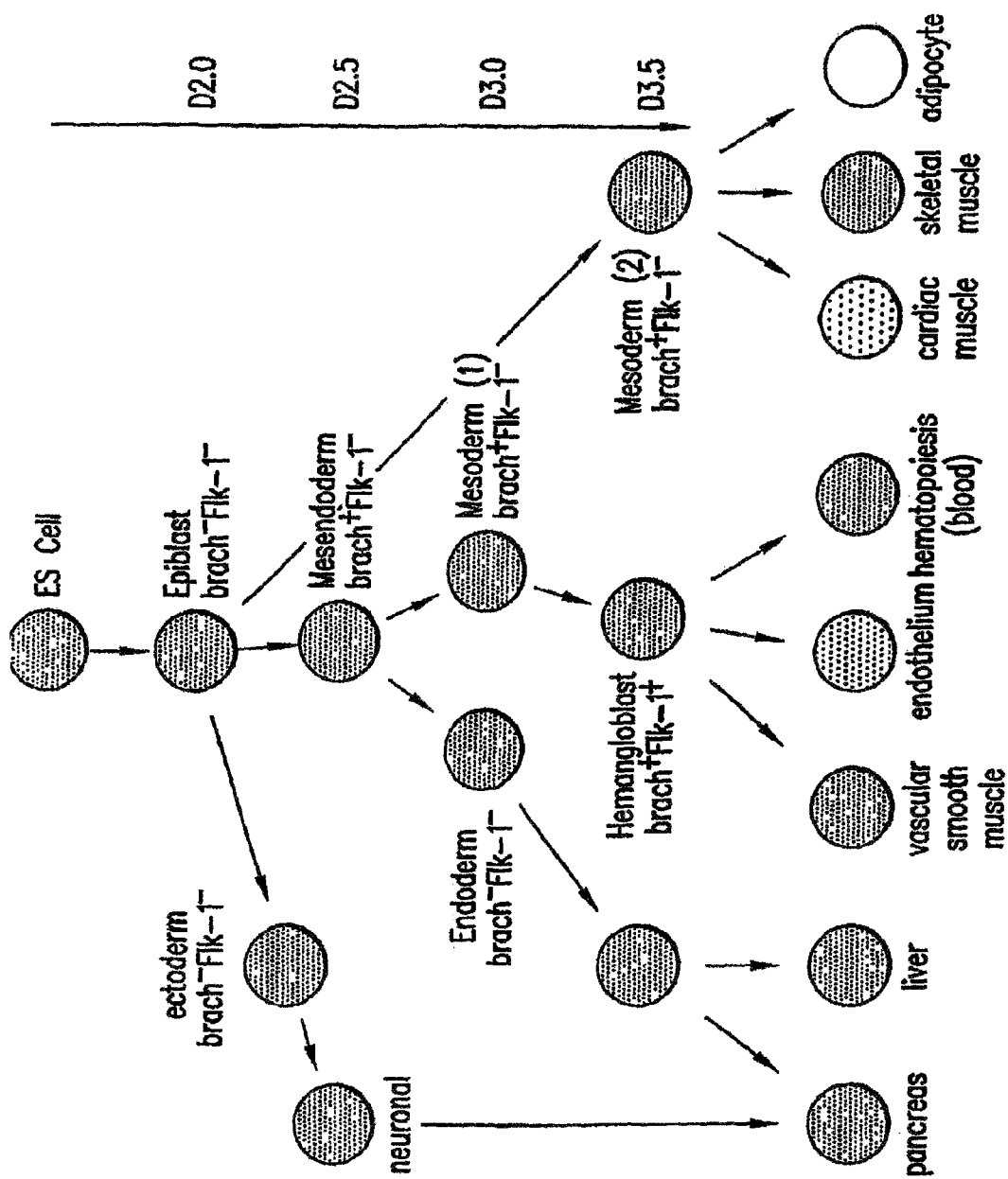
FIG. 17 is a diagram of the mesoderm and endoderm populations of the present invention and the differentiation of these population to derivative cell types.

As depicted in FIG. 17, it has been discovered in accordance with the present invention that mesendoderm is a previously unidentified cell population that gives rise to both endoderm and mesoderm and their corresponding lineages. It has been further discovered that presence or absence of serum in the in vitro culture may be used to dictate which lineage is generated from mesendoderm. In particular, a cell population that is enriched for endoderm cells may be obtained by culturing GFP-Bry ES cells generated from mouse ES cells in the presence of serum for about two to four days, sorting and isolating GFP+ cells, for example by flow cytometry, followed by culturing the GFP in the absence of serum for from about one to about ten days. The cell population that is isolated contains at least 50%, and preferably at least about 75%, and more preferably at least about 90%, and most preferably at least about 95% or at least about 99% endoderm cells, as defined hereinabove.

Cell populations that are enriched for endoderm cells may be obtained from GFP-Bry ES cells generated from human ES cells by culturing the GFP-Bry ES cells in the presence of serum for about 2 to 10 days, and then sorting and isolating GFP+ cells followed by culturing the GFP+ cells in the absence of serum for from about 1 to about 15 days.

The populations enriched for endoderm cells may be further enriched by identifying and sorting out KDR+ or Flk-1+ cells as described above.

It has further been discovered in accordance with the present invention that cell populations enriched for endoderm may be obtained by culturing GFP-Bry embryonic stem cells in the absence of serum and in the presence of the growth factor activin or nodal, for about two to about ten days, and isolating cells that express brachyury. The amount of activin or nodal is sufficient to induce differentiation of embryonic stem cells to endoderm. Such differentiation may be measured by assaying for the expression of genes associated with endoderm development, including for example HNF3β, Mixl-1, Sox17, Hex-1 or pdx-1. In a preferred embodiment, the concentration of activin is at least about 30 ng/ml. In another preferred embodiment the concentration of activin is about 100 ng/ml. In another embodiment, the GFP-Bry embryonic stem cells are cultured in the absence of serum and the presence of activin or nodal and an inhibitor of Wnt signalling for about two to about 10 days, and cells expressing brachyury are isolated. In a preferred embodiment the inhibitor is DKK-I. In other preferred embodiments the concentration of DKK-I is at least about 30 ng/ml, or about 100 ng/ml.

Cell populations enriched for mesoderm may be obtained by culturing GFP-Bry embryonic stem cells in the absence of serum and the presence of activin or nodal for about two to about ten days, and isolating cells that express brachyury. The amount of activin or nodal is sufficient to induce differentiation of embryonic stem cells to mesoderm, but insufficient to induce differentiation to endoderm. Differentiation to mesoderm may be measured by assaying for the expression of genes associated with mesoderm development, including for example GATA-I, and the absence of expression of genes associated with endoderm development. In a preferred embodiment, the concentration of activin is less than 30 ng/ml. In another preferred embodiment the concentration of activin is about 3 ng/ml.

It has been further discovered in accordance with the present invention that cell populations enriched for endoderm may be obtained by culturing embryonic stem cells in the absence of serum and the presence of activin or the related protein nodal and a Wnt molecule for about one to about six days, isolating brach+ HFN3β3 cells, and culturing the isolated cells in the absence of serum and the presence of an inhibitor of Wnt signaling for at least about one day. Isolation of brach+/HFN3β3+ cells may be facilitated by using the C4-HNF/GFP-Bry ES cells described hereinabove and selecting for CD4 and GFP, for example by cell sorting.

Wnt refers to a family of polypeptides well-known in the art. See, e.g. U.S. Pat. No. 6,159,462. The Wnt growth factor family includes proteins encoded by at least ten genes in mice and at least seven genes in human. In a preferred embodiment of the present invention, the Wnt molecule is recombinant Wnt 3d.

Inhibitors of Wnt signalling are also well-known in the art and include, for example, Wnt-I disclosed in U.S. Pat. No. 6,844,422 and Dickkopf-1 (DKK-I) disclosed by Glinka et al. (1998) Nature 391:357-362.

The present invention also provides a method of making cell populations enriched for endoderm comprising culturing mouse embryonic stem cells in the absence of serum for about two to about four days, or human embryonic cells in the absence of serum for about two to about ten days, isolating brach+/HFN3β3+ cells, and culturing the isolated cells for about one to about ten days in the absence of serum and the presence of activin or nodal and an inhibitor of Wnt signalling Isolation of brach+/HFN3β3+ cells may be facilitated by using the CD4-HNF/GFP-Bry ES cells as described above.

In each of the foregoing two methods, the amounts of activin or nodal and Wnt inhibitor are sufficient to induce differentiation of ES cells to endoderm. Differentiation may be measured by assaying for the expression of genes associated with endoderm development. In a preferred embodiment the concentration of activin is at least about 30 ng/nil. In another preferred embodiment the concentration of activin is about 100 ng/ml. In a preferred embodiment the Wnt inhibitor is DKK-I and the concentration of DKK-I is at least about 30 ng/ml. In another preferred embodiment the concentration of DKK-I is about 100 ng/ml.

The present invention further provides a method for making cell populations enriched for hepatocytes comprising culturing mouse embryonic stem cells in the absence of serum and the presence of activin or nodal for about two to four days, or human embryonic cells in the absence of serum and the presence of activin or nodal for about two to ten days, isolating brach+/HFN3β3+/cKit+ cells, culturing the isolated cells in the absence of serum and the presence of BMP-4 and bFGF under conditions sufficient for the production of hepatoblasts, and culturing the hepatoblast under conditions sufficient for the maturation of the hepatoblasts to hepatocytes. The amount of activin or nodal is sufficient to induce differentiation of ES cells to endoderm. In a preferred embodiment, activin is present at a concentration of at least about 30 ng/ml, BMP-4 is present at a concentration of at least about 10 ng/ml, and bFGF is present at a concentration of at least about 1.0 ng/ml. Hepatocytes may be identified by assays for glycogen storage or by observation, for example by electron microscopy, of characteristics of hepatocytes such as a large nucleus/cytoplasmic ratio, a large amount of glycogen storage and the presence of bile canaliculi.

The foregoing method provides cell populations that comprise at least about 10% hepatocytes. In a preferred embodiment, the cell populations comprise at least about 50% hepatocytes. In more preferred embodiments, the cell populations comprise at least about 60%, or at least about 70%, or at least about 80%, or most preferably at least about 90% hepatocytes.

The present invention further provides a method of identifying agents that affect the proliferation, differentiation or survival of the cell populations described above. The method comprises culturing cells from one of the cell populations described hereinabove in the absence and presence of an agent to be tested, and determining whether the agent has an effect on proliferation, differentiation or survival of the cell population. The agent to be tested may be natural or synthetic, one compound or a mixture, a small molecule or polymer including polypeptides, polysaccharides, polynucleotides and the like, an antibody or fragment thereof, a compound from a library of natural or synthetic compounds, a compound obtained from rational drug design, or any agent the effect of which on the cell population may be assessed using assays known in the art, for example standard proliferation and differentiation assays as described in U.S. Pat. No. 6,110,739. Such agents are useful for the control of cell growth and differentiation in vivo and in vitro.

The present invention further provides a method of identifying genes involved in cell differentiation and development of specific lineages and tissues. The method comprises isolating populations of GFP+ cells of the invention after different amounts of time in culture, comparing gene expression profiles in the different populations, and identifying genes that are uniquely expressed in a population. In a preferred embodiment, microarray analysis and subtractive hybridization are used to compare gene expression profiles.

In another embodiment, the present invention provides methods of making antibodies that recognize brachyury positive (brach+) cells but not brachyury negative (brach−) cells. Polyclonal antibodies may be made by injecting an animal with the cells of the invention in an immunogenic form. Also, antibodies may be made by identifying cells surface markers present in GFP+ but not GFP− cells, and making antibodies against the markers or fragments thereof. The antibodies may be monoclonal or polyclonal, and may be fragments, genetically engineered antibodies, single chain antibodies, and so on. Antibodies may be made by methods well-known in the art. Such antibodies are useful for identifying and isolating brach cells such as mesendoderm and mesoderm.

The present invention also provides a method for generating mammalian cells in vitro. In one embodiment, the method comprises culturing cells from a cell population enriched in mesendoderm and mesoderm cells under conditions effective for the differentiation of mesoderm into cardiac muscle, vascular smooth muscle, endothelium or hematopoietic cells. Conditions effective for differentiation into the various cell types in vitro are known in the art. In another embodiment, the method comprises culturing cells from a cell population enriched in endoderm cells under conditions effective for the differentiation of endoderm into liver cells or pancreatic cells. Effective conditions for such differentiation are known in the art. The production of insulin-producing pancreatic islet cells is specifically contemplated.

As demonstrated in accordance with the present invention, brach+ cells isolated from different aged EBs have different developmental potentials. BrachVFlk− cells from about day 3 mouse EBs efficiently generate hemotopoietic and endothelial lineages, while the cells from about day 3 to 10 EBs generate cells of cardiomyocyte lineages. Accordingly, by adjusting the time of culture of the ES cells used for obtaining the cell population enriched for mesendoderm and mesoderm, one of ordinary skill in the art can select for efficient production of hemotopoetic and endothelial lineages or cardiomyocyte lineages.

Such cells are useful, for example, for cell replacement therapy for the treatment of disorders that result from destruction or dysfunction of a limited number of cell types. Such disorders include diabetes mellitus, liver failure, heart failure, cardiovascular and other vascular disease, Duchenne's muscular dystrophy, osteogenesis imperfecta, and disorders treatable by bone marrow transplant, for example leukemias and anemias. See, Odorico et al., (2001) Stem Cells 19:193-204.

The cell populations of the present invention are useful for generating differentiated cells and tissues for cell replacement therapies. The suitability of the cell populations of the present invention for cell replacement therapy may be assessed by transplanting the cells into animal models of disorders that are associated with the destruction or dysfunction of a limited number of cell types. For example, the fumarylacetoacetate (FAH) deficient mouse disclosed for example by Grompe et al. (1993) Genes & Dev. 7:2298, incorporated herein by reference, provides a model for liver failure. FAH deficient mice suffer from progressive liver failure and renal tubular damage unless treated with NTBC (2-(2-nitro-4-trifluoromethyl benzoyl)-1,3-cyclohexedione) or transplanted with normal hepatocytes. These mice thus provide an ideal model for testing the potential of cells with characteristics of immature hepatocytes generated from EBs. Methods for transplantation of hepatocytes into FAH deficient mice removed from NTBC are known in the art and disclosed for example by Oversturf et al. (1996) Nature Genet. 12:266-273. Normal liver function is indicated by survival of the mice, and may also be assessed by measuring serum aspartate transaminase levels, plasma bilirubin levels, and by determining normal structure of the regenerated liver.

Animal models for other disorders that result from the destruction or dysfunction of particular cells types are known in the art. Such models may similarly be used to assess other cell populations of the present invention.

In a preferred embodiment, the present invention provides a method of hepatocyte replacement therapy comprising administering to a subject in need of such treatment a composition comprising hepatocytes produced by the method of the invention. In a preferred embodiment the subject is a human The composition may be administered by a route that results in delivery to hepatic tissue, including, for example, injection, implantation or infusion. The present method is useful for the treatment of liver failure, liver-based metabolic disease, and chronic liver disease.

The present invention also provides a transgenic non-human mammal in which DNA encoding a selectable marker is present in the brachyury locus such that one brachyury allele is inactivated and the selectable marker is expressed in cells in which the brachyury locus is transcribed. In a preferred embodiment the mammal is a mouse and the selectable marker is GFP. In particular, the transgenic mouse has a genome comprising a transgene in which a DNA sequence encoding GFP is operably linked to brachyury regulatory elements, and the transgene is expressed in cells that normally express brachyury. The transgenic mouse may be obtained by injecting the GFP-Bry ES cells described hereinabove into blastocysts, which are then implanted into pseudopregnant females. Transgenic pups are identified by the short-tail phenotype associated with brach +/−, and by molecular analysis. Such transgenic animals are useful for obtaining early embryos from which to isolate mesoderm to be used in accordance with the methods of the invention, and for the identification, isolation and characterization of any adult cell populations that express the brachyury gene. Such cells may represent novel stem cell populations.

All references cited herein are incorporated herein in their entirety.

The following examples serve to further illustrate the present invention.

EXAMPLE 1

Materials and Methods

ES cell growth and differentiation. ES cells were maintained on irradiated embryonic feeder cells in Dulbecco's Modified Eagle Medium (DMEM) supplemented with 15% fetal calf serum (FCS), penicillin, streptomycin, LIF (1% conditioned medium) and $1.5 \times 10^{-4}$ M monothioglycerol (MTG; Sigma). Two days prior to the onset of differentiation, cells were transferred on gelatinized plates in the same media. For the generation of EBs, ES cells were trypsinized and plated at various densities in differentiation cultures. Differentiation of EBs was carried out in 60 mm petri grade dishes in IMDM supplemented with 15% FCS, 2 mM L-glutamine (Gibco/BRL), transferrin (200 ug/ml), 0.5 mM ascorbic acid (Sigma), and $4.5 \times 10^{-4}$ M MTG. Cultures were maintained in a humidified chamber in a 5% $CO_2$/air mixture at 37° C.

Serum Free Medium. Two different serum-free media were used in different aspects of the following examples: IIMD supplemented with Knockout™ SR (Gibco BRL) and StemPro® 34 (Gibco BRL).

Methylcellulose Colony Assay. A) Blast colonies: For the generation of blast cell colonies (BL-CFC assay), EB-derived cells were plated at $0.5 \times -1.5 \times 10^5$ cells/ml in 1% methylcellulose supplemented with 10% FCS (Hyclone), vascular endothelial growth factor (VEGF; 5 ng/ml), c-kit ligand (KL; 1% conditioned medium), IL-6 (5ng/ml) and 25% D4T endothelial cell conditioned medium (Kennedy et al. (1997) Nature 386:488-93). Transitional colonies were generated in the absence of VEGF. Colonies were scored following four days of culture. B) Hematopoietic colonies: For the growth of primitive and definitive hematopoietic colonies, cells were plated in 1% methylcellulose containing 10% plasma-derived serum (PDS; Antech), 5% protein-free hybridoma medium (PFHM-II; Gibco-BRL) plus the following cytokines: c-kit ligand (KL; 1% conditioned medium), erythropoietin (2 U/ml), IL-11 (25 ng/ml), IL-3 (1% conditioned medium), GM-CSF (3 ng/ml), G-CSF (30 ng/ml), M-CSF (5 ng/ml), IL-6 (5 ng/ml) and thrombopoietin (TPO; 5ng/ml). Cultures were maintained at 37° C., 5% $CO_2$. Primitive erythroid colonies were scored at day 5-6 of culture, whereas definitive erythroid (BFU-E), macrophage, and multilineage colonies were counted at 7-10 days of culture. C-kit ligand was derived from media conditioned by CHO cells transfected with KL expression vector (kindly provided by Genetics Institute). IL-3 was obtained from medium conditioned by X63 AG8-653 myeloma cells transfected with a vector expressing IL-3. VEGF, GM-CSF, M-CSF, IL-6, IL-11, activin BMP2, BMP4, bFGF, FGF8, and Ihh were purchased from R&D systems.

Reaggregation Cultures. Cells were cultured at $2 \times 10^5$ per ml IMDM supplemented with 15% FCS (or Knockout SR), 2 mM L-glutamine (Gibco/BRL), 0.5 mM ascorbic acid (Sigma), and $4.5 \times 10^{-4}$ M MTG in 24-well petri-grade plates. These were used to prevent adhesion of the cells to the bottom of the well.

Cardiac muscle assays. GFP+ cells were reaggregated in IMDM supplemented with 15% serum replacement. Twenty hours later the aggregates were cultured in wells of either a 24- or 96-well plate in IMDM with 10% serum replacement (serum-free). The wells were pre-treated with gelatin. Cultured were monitored daily for the development of the appearance of beating cells. Beating cells were usually detected between days 2 and 6 of culture.

Cell surface markers staining and FACS analysis. Standard conditions were used to stain the cells. Stained suspensions were analyzed on a FACScan™ (Becton Dickinson, Calif.).

Gene Expression Analysis For the poly A+ RT-PCR analysis the method of Brady et al. ((1990) Meth. in Mol. and Cell Bio. 2:17-25) was used. Reverse transcription, poly-A tailing and PCR procedures were performed as described, with the exception that the X-dT oligonucleotide was shortened to 5'-GTTAACTCGAGAATTC(T)$_{24}$-3' (SEQ. ID. NO. 1). The amplified products from the PCR reaction were separated on agarose gels and transferred to a Zeta-probe® GT membrane (Biorad) or transferred to the membrane with a slot blot apparatus (Schleicher & Schuell). The resulting blots were hybridized with $^{32}$P randomly primed cDNA fragments (Ready-to-Go Labelling, Pharmacia) corresponding to the 3' region of the genes (for all except (β-H1). A β-H1-specific probe was prepared by annealing two oligonucleotides, (5'-TGGAGTCAAAGAGGGCATCATAGACACATGGG-3' (SEQ. ID. NO. 2), 5'-CAGTACACTGGCAATCCCATGTG-3' (SEQ. ID. NO. 3)) which share an 8 base homology at their 3' termini. This β-H1 specific oligonucleotide was labeled with $^{32}$P using a Klenow fill-in reaction. For gene specific PCR, total RNA was extracted from each sample with RNeasy® mini kit and treated with RNase free DNase (Qiagen). Two microgram of total RNA was reverse-transcribed into cDNA with random hexamer using a Omniscript™ RT kit (Qiagen). PCR was carried out using appropriate oligonucleotides. The PCR reactions were performed with 2.5 U of Taq polymerase (Promega), PCR buffer, 2.5 mM $MgCl_2$, 0.2 uM of each primer and 0.2 mM dNTP. Cycling conditions were as follows; 94° C. for 5 min followed by 35 cycles of amplification (94° C. denaturation for 1 min, 60° C. annealing for 1 min, 72° C. elongation for 1 min) with a final incubation at 72° C. for 7 min

EXAMPLE 2

Generation of Targeted ES Cells

Under appropriate conditions in culture, embryonic stem (ES) cells will differentiate and form three dimensional colonies known as embryoid bodies (EBs) that contain developing cell populations from a broad spectrum of lineages. Smith (2001) Annu. Rev. Cell Dev. Biol. 17:435-62. Among these EB-derived populations, one can detect mesodermal derivatives including those of the hematopoietic, endothelial, cardiac muscle and skeletal muscle lineages.

In order to track the onset of mesoderm in EBs and to isolate cells representing this population, the green fluorescence protein (GFP) was targeted to the brachyury locus. The targeting construct contained the GFP cDNA, and artificial intron, SV40 poly(A) sequences and a loxP flanked neo cassette in the first exon and is depicted in FIG. 1. The thymidine kinase (TK) gene was included at the 3' end of the targeting construct to select against random integration. The targeting vector was constructed as follows.

A BAC clone carrying the entire mouse Brachyury (Bry) gene was isolated by PCR screening of a 129/Ola strain genomic library (Genome Systems) with primers 5'-AAGGAGCTAACT AACGAGATGAT-3' (SEQ. ID. NO. 4) and 5'-TACCTTCAGCACCGGGAACAT3' (SEQ. ID. NO. 5). These primers anneal within the first and second Bry exon, respectively, and amplify a diagnostic band of ~600 bp. An approximately 3 kb long PstI restriction fragment carrying the 1 exon of the Bry gene along with more than 2 kb of 5' flanking region was identified and subcloned from the BAC into plasmid pBSK (Strategene), resulting in construct pBSK.Bry-5'. Approximately 2 kb of the region immediately upstream of the start codon were sequenced to identify appropriate primer annealing sites for the construction of vectors.

Oligos 5'-GCTAGCTAATGGATCCA-3' (SEQ. ID. NO. 6)/5'-GATCTGGATCCATTAGCTAGCTGCA-3' (SEQ. ID. NO. 7) and 5'-GATCTTAATGAACGGCAGGTGGGT-GCGCGTCCGGAG-3' (SEQ. ID. NO. 8)/5'TCGACTCCG-GACGCGCACCCACCTGCCGTTCATTAA-3' (SEQ. ID. NO. 9) were inserted into the PstI/SalI sites of plasmid pBSK to create a new, more suitable polylinker with two successive translational stop codons and an artificial 3' splice site (construct pBry-AA). Plasmid pEGFP.Cl (Clontech) was double-digested with NheI/BglII and the resulting ~760 bp DNA fragment encoding EGFP without stop codon was cloned into the NheI/BglII sites of pBRY-AA, resulting in construct pBry-AB. An XhoI/SalI fragment of plasmid pL2-Neo2 carrying a loxP-flanked neomycin resistance gene was inserted into the SalI site of pBry-AB to give rise to plasmid pBry-AC (transcription of EGFP and Neo in same direction).

A 556 bp XmaI/MluI fragment carrying a consensus splice donor site, an artificial intron, a splice acceptor site and a short exon including the SV40 polyadenylation sequence, was excised from the commercial expression vector pBK-CMV (Stratagene). This fragment was inserted into plasmid pBry-AC in the following way: the XmaI end was ligated into the BspEI site following the last EGFP codon, whereas the Mlu end was inserted along with oligos 5'-CGCGTTACTAGTAAGACGTCT-3' (SEQ. ID. NO. 10)/ 5'-CCGGAGA CGTCTTACTAGTAA-3' (SEQ. ID. NO. 11) as linkers into the BspEI site located just upstream of the loxP-neo-loxP cassette. Resulting construct: pBry-AE. An ~1.9 kb XhoI/SalI fragment encoding the HSV thymidine kinase gene was inserted into the XhoI site of pBry-AE to allow selection against random integration (construct pBry-AH). A NotI/Eco47lII fragment encoding the "short arm" of homology was excised from pBry-AF and cloned into the NotI/Eco47lII sites of pBry-AH to give rise to plasmid pBry-AI. The "long arm" of homology was excised from pBry-AK with SalI and inserted in the correct orientation into the SalI site of pBry-AI to yield final targeting vector B.

Embryonic stem cells (E14. 1, 129/Ola Hooper et al. (1987) Nature 326:292) were electroporated with NotI-linearized targeting vector pBry-AM. Four dishes with transfected cells were subjected to G418 single-and another four dishes to G418+Gancyclovir (Ganc) double-selection. Clones that had undergone a homologous recombination event were identified by PCR with one primer (5'-CAGG-TAGAACCCACAACTCCGAC-3' (SEQ. ID. NO. 12)) annealing to genomic sequences in the 5' region of the Bry gene, just upstream of the "short arm of homology", the other (5'-CCGGACACGCTGAACTTGTGGC-3' (SEQ. ID. NO. 13)) to the 5' portion of EGFP (diagnostic band: approximately 1.3 kb). Correctly targeted clones were confirmed by Southern blot analysis: genomic DNA of candidate clones was digested with HincII and hybridized to a probe located outside of the targeting construct. The probe was derived from the Bry 5' flanking region (-2018 to -1249 with respect to the Bry ATG start codon) by PCR using the oligonucleotide pair 5'-ACAGGATCCCTAAGCCT-CAAAAGAGTCGCT-3' (SEQ. ID. NO. 14)/5'-TCTTG-GATCCTCCTAT CCTATCCCGAAGCTCCT-3' (SEQ. ID. NO. 15). 384 G418 single- and 80 G418+Ganc double-selected clones were screened, of which 4 respectively 3 proved to be positive, corresponding to a targeting efficiency of 1.04% and 3.75%. Two positive clones were transiently transfected with a modified Cre recombinase expression vector to remove the neo gene. These targeted clones are referred to hereinafter as GFP-Bry ES cells.

Brachyury is expressed transiently in developing EBs with the onset preceding the expression of genes that define the establishment of the hematopoietic and endothelial lineages. To determine whether GFP expression in GFP-Bry ES cells accurately reflects expression of the brachyury gene during EB development, GFP expression was assessed.

Figure 2A:
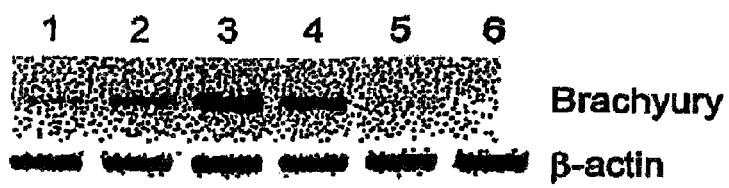
FIGS. 2A and 2B depict the expression of GFP and brachyury in developing embryoid bodies (EBs).
Figure 2B:
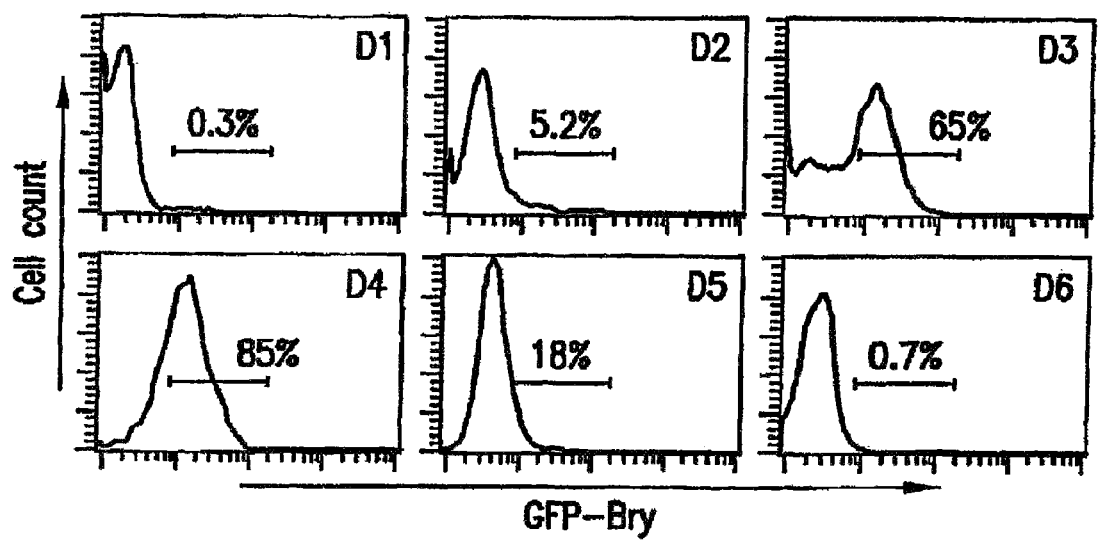

A typical expression pattern during a 6-day EB differentiation period is shown in FIG. 2A. In this experiment, low levels of message were detected within 24 hours of differentiation. Expression was upregulated over the next 48 hours, persisted through day 4 and then declined sharply to undetectable levels by day 6 of differentiation. GFP expression, as defined by FACS analysis, followed a similar temporal pattern. Low levels of GFP$^+$ cells (~5%) were detected as early as day 2 of differentiation. More than half (65%) of the EB-derived cells expressed GFP at day 3 and almost all the cells were positive at day 4 of differentiation. As observed by PCR, expression dropped sharply after this point and by day 6 few, if any, GFP$^+$ cells were present. This rapid decline in GFP expression indicated that it did not persist within the cells for extended periods of time. The high proportion of GFP$^+$ cells at days 3 and 4 of differentiation suggests that development of mesoderm within the EBs under these conditions is extensive. Taken together, these findings indicate that GFP expression accurately reflects expression of the brachyury gene during EB development.

Figure 3A:
FIGS. 3A, 3B and 3C depict the developmental potential of wild type and GFP-Bry ES cells.
Figure 3B:
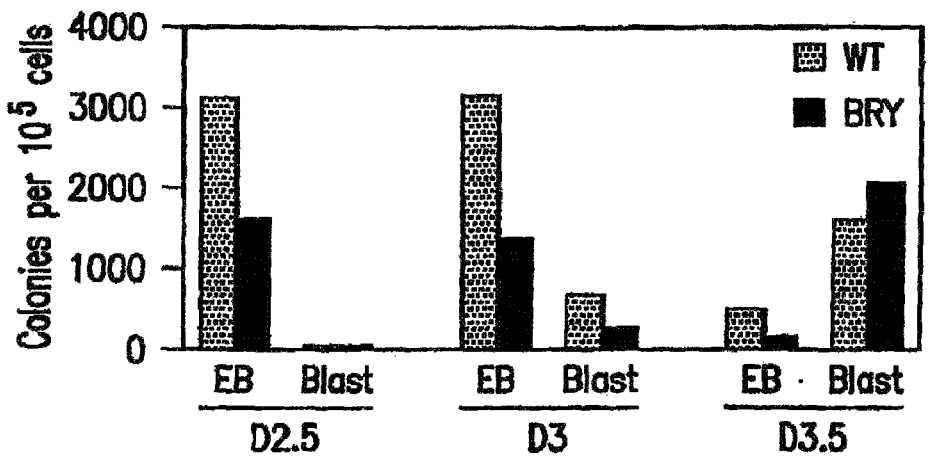
Figure 3C:
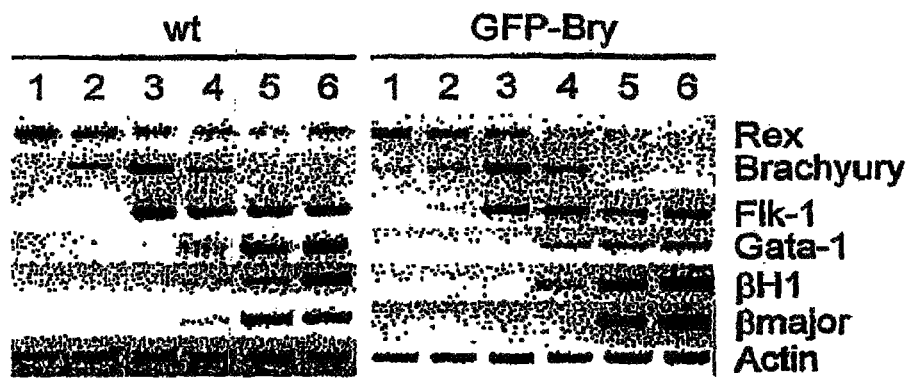

The possibility that inactivation of a single brachyury allele could have detrimental effects on the in vitro developmental potential of the ES cells was assessed. As indicated, heterozygous mice demonstrate a mild phenotype. To determine if the GFP-Bry ES cells display any detectable defects in hematopoietic development, EBs generated from them were analyzed for hematopoietic precursor and blast colony-forming cell (BL-CFC) content and for gene expression patterns. The data in FIGS. 3A and 3B indicate that GFP-Bry ES cells generate comparable numbers of primitive (Ery$^p$) and definitive (Ery$^d$, Mac, Mac/Ery, and Mix) hematopoietic precursors and BL-CFC compared to the wild type cells. Gene expression patterns (FIG. 3C) confirmed the precursor analysis and show little difference between the EBs generated from the GFP-Bry and wild type ES cells. Both sets of EBs showed a decline in Rex-1 expression over the first 3 days of differentiation. Rex-1 is a transcription factor that is expressed in ES cells and downregulated as they undergo differentiation. Rogers et al. (1991) Development 113:815-24. The decline in Rex-1 is followed by the typical transient wave of brachyury expression which immediately precedes the onset of genes involved in the development of the hematopoietic and endothelial lineages. Flk-1, a receptor tyrosine kinase essential for the establishment of these lineages (Shalaby et al. (1995) Nature 376:62-6) is expressed between day 3 and 6 of differentiation. GATA-1, a hematopoietic transcription factor, and the embryonic and adult globin genes, βH1 and βmajor, were detected at low levels at day 4 of differentiation. Expression of all 3 genes was upregulated over the next 24 hours, reflecting the expansion and maturation of the primitive erythroid lineage at this developmental stage. Palis et al. (1999) Development 126:5073-84. The precursor numbers and the gene expression patterns observed in this example are consistent with those found in previous studies and indicate that the molecular programs leading to the establishment of the hematopoietic system are intact in the targeted GFP-Bry ES cells.

EXAMPLE 3

Isolation of Brachyury+ Cells

Figure 4A:
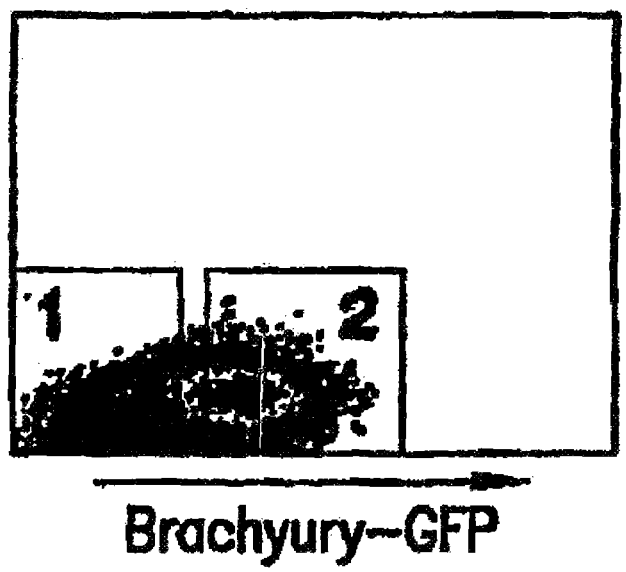
FIGS. 4A and 4B depict the gene expression profile of EB fractions isolated on the basis of GFP.

To determine if brachyury+ cells could be isolated based on GFP expression, the GFP+ population from day 3.5 EBs was sorted and analyzed for expression of appropriate genes. FIG. 4A shows the gates used for the isolation of the GFP positive (2) and negative(1) populations. RT-PCR analysis revealed brachyury expression was restricted to the GFP+ fraction indicating that cell sorting based on GFP expression can be used to isolate brachyury+ cells. Flk-1, one of the earliest makers of hematopoietic and endothelial development, was present at higher levels in GFP+ that in the GFP− fraction indicating that it was expressed in at least a subpopulation of brachyury+ cells. In contrast to brachyury and Flk-1, Pax-6, a gene involved in early neuronal development [79,80], was expressed at higher levels in the GFP− fraction consistent with precursors of this lineage being brachyury negative. These cell-sorting studies indicate that expression of GFP under the control of the brachyury locus provides a novel marker for the isolation, characterization and manipulation of brachyury+ cells from EBs.

This example demonstrates that GFP+ cells can be isolated from day 3.5 EBs by cell sorting. Gene expression analysis of the GFP+ and GFP− fractions shows that brachyury expression segregates predominantly to the positive fraction, a finding which clearly demonstrates that fractionation based on GFP provides a method for isolating brachyury positive cells. In addition to brachyury, the receptor tyrosine Flk-1 involved in early hematopoietic and endothelial development is also expressed at higher levels in the positive than in the negative fraction. In contrast, Rex-1 and Pax-6, markers of early ectoderm and neuroectoderm, are expressed in the GFP− fraction. These findings demonstrate that expression of GFP in the context of brachyury can be used to separate mesoderm from ectoderm.

EXAMPLE 4

Figure 4B:
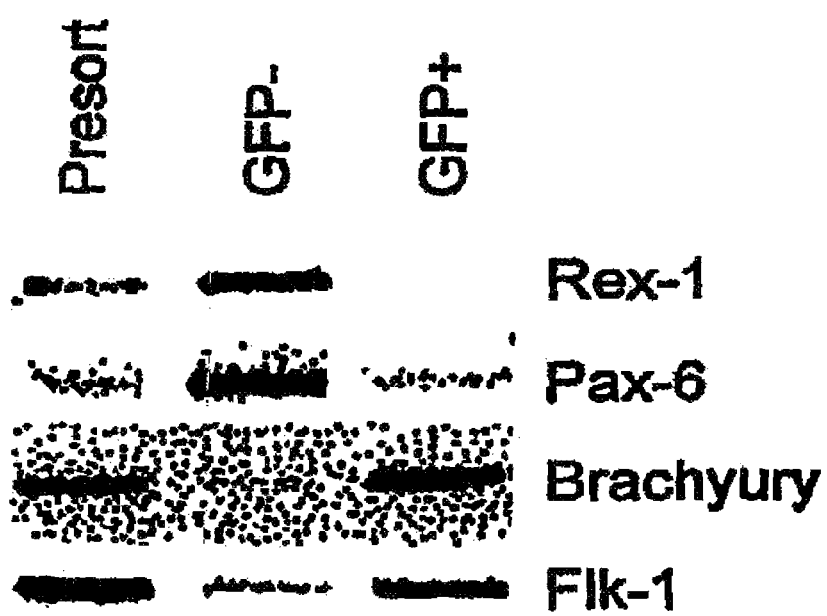

Separation of Brachyury Positive Cells Into Subpopulations Based Upon Flk-1 Expression Flk-1 has been shown to be essential for the establishment of the hematopoietic and endothelial lineages in the early embryo and is expressed on the earliest precursors of these lineages, including the BL-CFC [Faloon et al. (2000) Development 127:1931-41]. Given this pivotal role in blood and vascular development, its expression within the GFP+ population was hypothesized to define a subpopulation of mesoderm undergoing specification to these lineages. To investigate this possibility further, EBs were analyzed at several stages of development for the presence of GFP and Flk-1 positive cells. In the experiment illustrated in FIG. 5A, 4.8% of the day 3.0 EB population expressed GFP but not Flk-1, whereas 1.2% of the cells expressed both markers. The size of both fractions increased dramatically over the next 12 hours with the GFP+/Flk-1− and GFP+/Flk-1+ cells representing 52% and 26% of the total EB population, respectively. To assess the developmental potential of the three populations defined by GFP and Flk-1 expression, GFP−/Flk-1− (fraction 2), GFP+/Flk-1− (fraction 3) and GFP+/Flk-1+ (fraction 4) cells were isolated at both time points and analyzed for BL-CFC and 2° EB content and for gene expression patterns. The potential of the fractions was compared to that of the pre-sorted population (fraction 1). The majority of the BL-CFC were found in the GFP+/Flk-1+ fraction at both day 3.0 and 3.5 of differentiation (FIG. 5B). This is not surprising given that previous studies have shown that all BL-CFC express Flk-1. The 2° EB were restricted to the GFP−/Flk-1− fraction, a finding consistent with the fact that they derive from residual undifferentiated ES cells in the primary EBs. The GFP+/Flk-1− fraction generated few colonies under the conditions used in these cultures. The gene expression analysis revealed some interesting differences between the populations isolated at the 2 time points (FIG. 5C). Rex-1, the ES cell marker, was expressed at lower levels in the GFP+ than in the GFP− fraction, indicating that these populations are undergoing differentiation. Brachyury was expressed in the GFP+ fractions at both time points. The levels appear to be higher in the GFP+/Flk-1− than the GFP+/Flk-1+ fraction isolated from day 3.5 EBs, suggesting that its expression could be downregulated as these cells mature towards the hematopoietic and endothelial lineages. As expected, Flk-1 was expressed predominantly in the GFP+/Flk-1+ cells at both time points. Scl, a helix-loop-helix transcription factor that is essential for both primitive and definitive hematopoietic development (Shivdasani et al. (1995) Nature 373:432-4), appears to be restricted to the GFP+/Flk-1+ fraction. Similarly, the transcription factor Runx1, required for establishment of the definitive hematopoietic system (Wang et al. (1996) Proc. Natl. Acad. Sci. 93:3444-9), was most readily detected in GFP+/Flk-1+ fraction. There was some Runx1 expression in the GFP+/Flk-1− fraction isolated from day 3.0 EBs. Nodal is expressed in all 3 fractions at day 3 of differentiation. At day 3.5, the levels of expression in the GFP+/Flk-1+ fraction appear to be significantly lower than in the other fractions. Wnt3a and Wnt8a showed a remarkably restricted pattern of expression and were found only in the GFP+/Flk-1− fraction at both time points, consistent with an early mesoderm function prior to the expression of lineage restricted markers. BMP2 was expressed in both GFP+ fractions whereas BMP4 was found predominantly in the GFP+/Flk-1+ cells, indicating that these molecules play a role at distinct stages of development in this system. The BL-CFC potential and gene expression pattern of the GFP+/Flk-1+ cells indicates that they are representative of the extraembryonic mesoderm found in the mouse embryo.

Figure 5A:
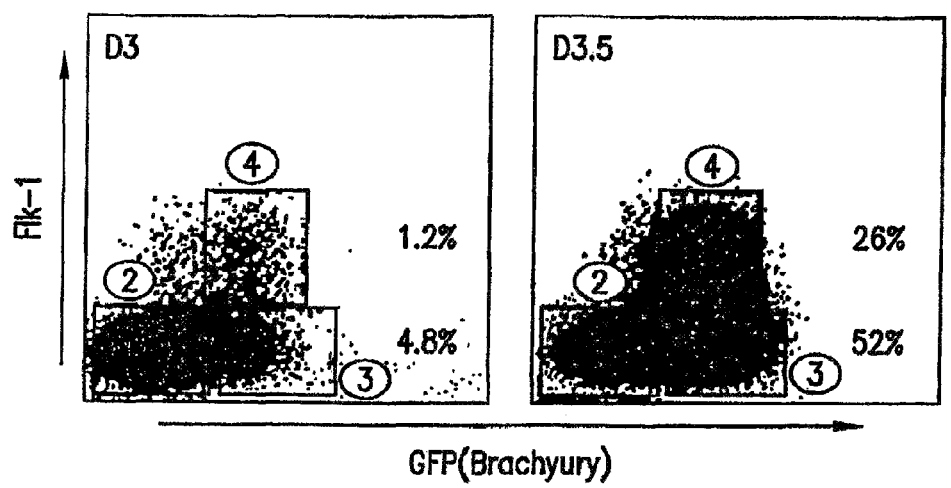
FIGS. 5A, 5B and 5C demonstrate the isolation and characterization of GFP and Flk-1 populations.
Figure 5B:
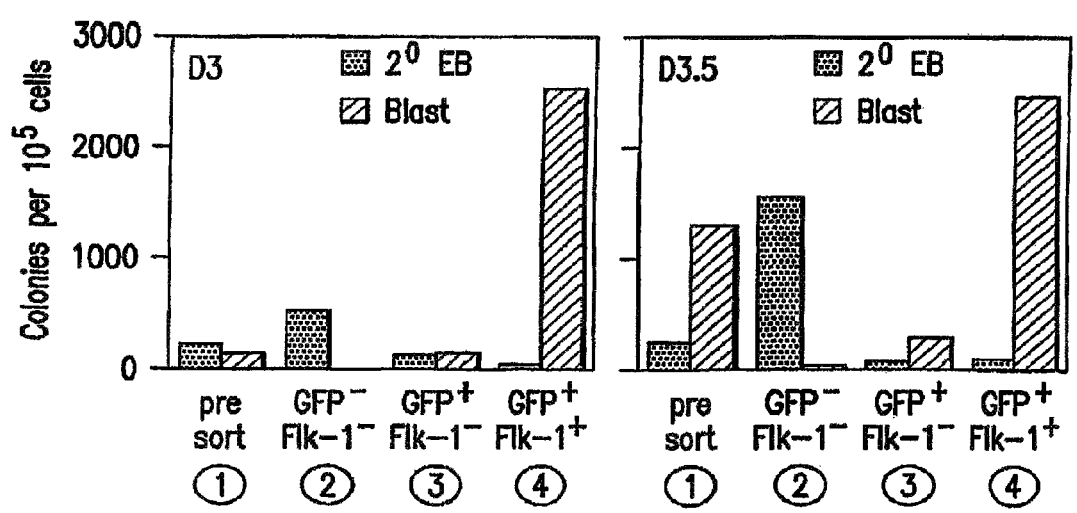
Figure 5C:
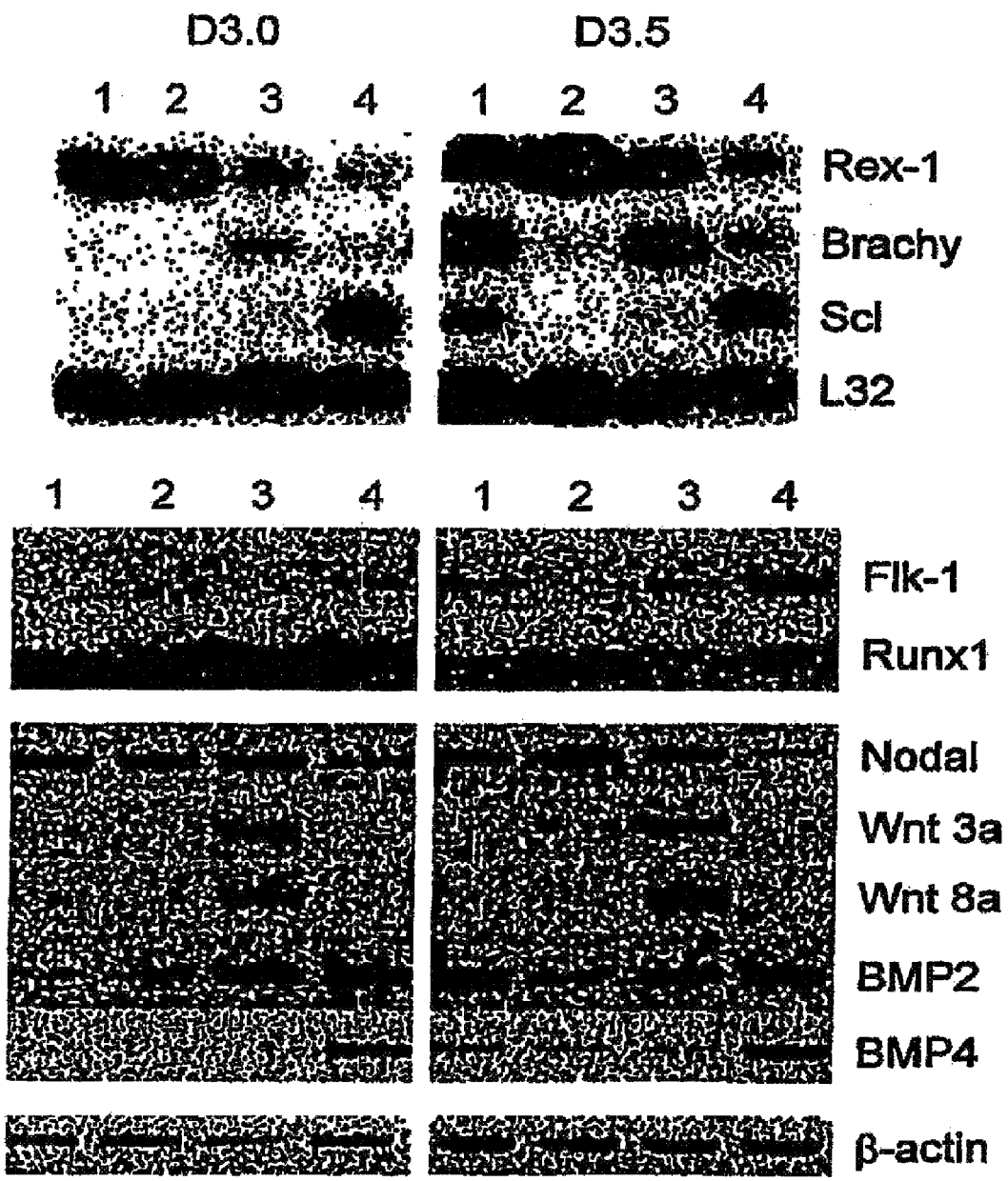

This example demonstrates that the brachyury fraction of day 3 and day 3.5 EBs can be separated into two fractions based on Flk-1 expression: brachyury+/Flk-1− (GFP+/Flk-1−) and brachyury+/Flk-1+ (GFP+/Flk-1+) (FIG. 5A). Functional studies demonstrated that precursors (BL-CFC) able to generate both hematopoietic and endothelial cell segregated to the (GFP+/Flk-1+) fraction, suggesting that upregulation of Flk-1 is indicative of commitment to these lineages (FIG. 5B). Gene expression studies demonstrated distinct differences between the GFP+/Flk-1− and GFP+/Flk-1+ populations (FIG. 5C).

EXAMPLE 5

Developmental Relationships among the GFP/FLK Fractions

Figure 6:
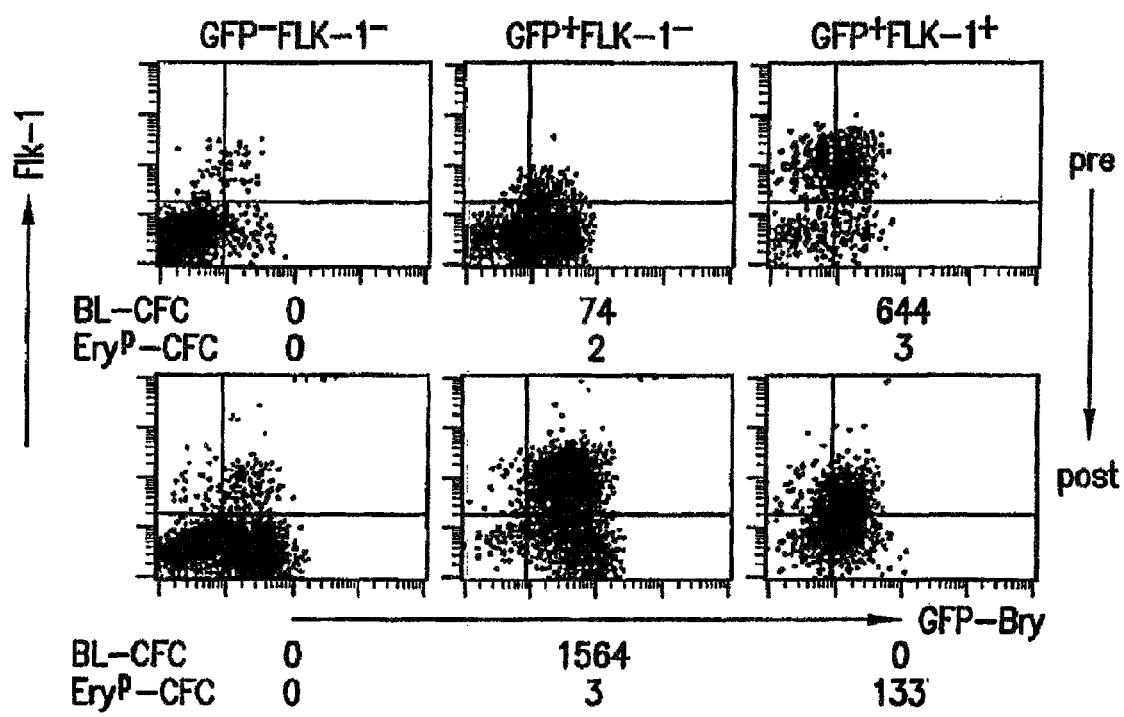
FIG. 6 depicts the expression of GFP and Flk-1 in isolated day 3 EB-derived fractions. The top row shows the expression profiles of the three fractions prior to culture (pre). The bottom row indicates the profile of the same cell populations following 20 hours of culture (post). The numbers below each profile indicate the BL-CFC and primitive erythroid ($Ery^P$-CFC) potential (precursors per 1×10$^5$ cells plated) of each population.

The expression patterns observed in FIG. 5 are consistent with the interpretation that the three fractions represent a developmental continuum with the GFP$^-$/Flk-1$^-$ cells giving rise to the GFP$^+$/Flk-1$^-$ cells which in turn give rise to the GFP$^+$/Flk-1$^+$ cells. To determine if these fractions do represent specific stages within a common developmental pathway, each was isolated from day 3 EBs, cultured for 20 hours and then re-analyzed for GFP and Flk-1 expression. BL-CFC and Ery$^P$-CFC potential was determined for each of the populations prior to and following culture. The isolated cells were cultured at densities of 1×10$^5$ cells or greater in petri-grade 24-well plates in the same medium used for EB differentiation. Under these conditions, the cells rapidly reaggregate and form EB-like structures that appear to follow a normal developmental program with little expansion or loss in cell number. Following the 20-hour reaggregation culture, the GFP$^-$/Flk-1$^-$ cells gave rise to a significant population of GFP$^+$/Flk-1$^-$ cells as well as to a small number of GFP$^+$/Flk-1$^+$. GFP$^+$/Flk-1$^-$ cells generated a substantial population of GFP$^+$/Flk-1$^+$ cells during the same culture period. The GFP$^+$/Flk-1$^+$ population appeared to lose some GFP and Flk-1 expression following the reaggregation culture. Results are shown in FIG. 6. The changes in precursor potential were consistent with the changes in surface markers. The GFP$^-$/Flk-1$^-$ fraction, the most immature of the three, contained an undetectable number of BL-CFC and Ery$^P$-CFC before or after culture. The GFP$^+$/Flk-1$^-$ fraction also contained few BL-CFC and Ery$^P$-CFC prior to culture. However, following culture, the BL-CFC potential increased dramatically, from 74 to 1564 per 10$^5$ cells, consistent with the increase in Flk-1 expression. The frequency of Ery$^P$-CFC did not change during the culture period. The GFP$^+$/Flk-1$^+$ fraction contained BL-CFC but few Ery$^P$-CFC prior to culture. No BL-CFC were detected following culture, however, the population now contained Ery$^P$-CFC. Together with the surface marker analysis, these precursor data support a developmental progression from a pre-mesoderm (GFP$^-$/Flk-1$^-$) to a mesoderm/pre-hemangioblast (BL-CFC) population (GFP$^+$/Flk-1$^-$) to a hemangioblast/pre-erythroid population (GFP$^+$/Flk-1$^+$) to a post hemangioblast/erythroid population (possibly GFP$^{lo}$/Flk-1$^{lo}$). Not all the cells in a given population appear to differentiate following the 20-hour culture period as cells with the starting phenotype persisted in the GFP$^-$/Flk-1$^-$ and GFP$^+$/Flk-1$^-$ cultures.

This example indicates that when isolated and recultured for 20-24 hours, each of the three populations isolated from day 3 EBs continued to differentiate and in a pattern that indicates that these populations represent a developmental continuum. For instance, GFP$^-$/Flk-1$^-$ gave rise to GFP$^+$/Flk-1$^-$ cells which in turn gave rise to GFP$^+$/Flk-1$^+$. These changes in cell surface characteristics were associated with the expected changes in developmental potential. The GFP$^+$/Flk-1$^-$ fraction contained few hematopoietic/endothelial precursors (BL-CFC) prior to culture. Following culture, these precursors were detected, clearly demonstrating that the GFP$^+$/Flk-1$^-$ fraction from day 3 EBs does contain the potential to give rise to Flk-1$^+$ cells with hematopoietic and endothelial potential.

EXAMPLE 6

Potential of GFP/Flk-1$^-$ Cells

Figure 7A:
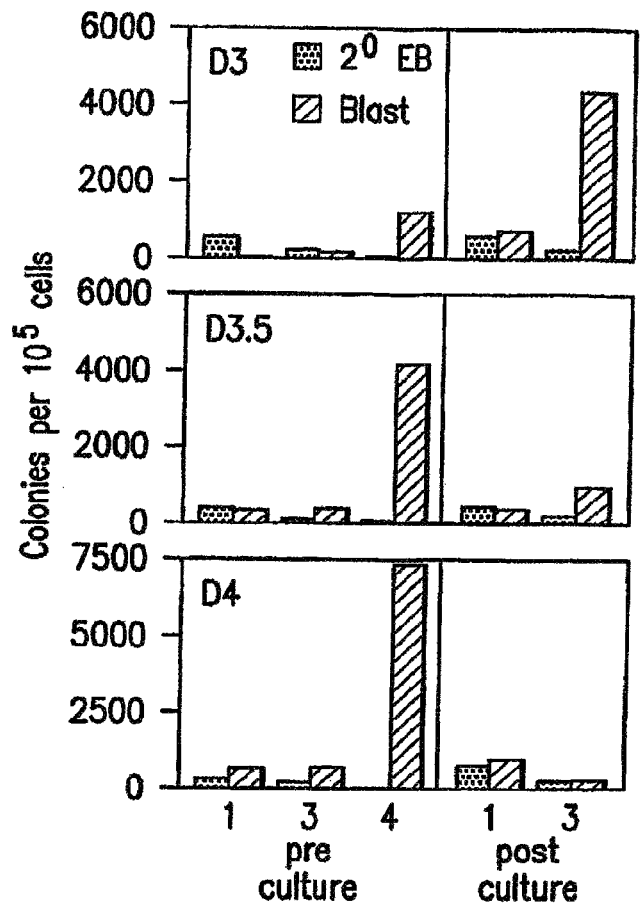
FIGS. 7A and 7B depict the BL-CFC potential and Flk-1 expression of the isolated cell populations prior to and following culture.
Figure 7B:
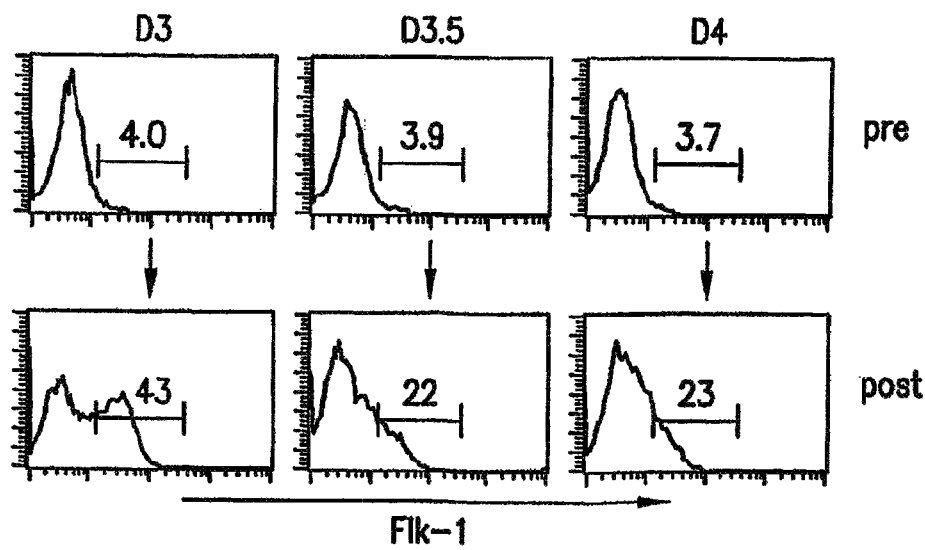

The foregoing examples demonstrated that GFP$^+$/Flk-1$^-$ cells isolated from day 3.0 EBs efficiently generated GFP$^+$/Flk-1$^+$ cells and BL-CFC following overnight culture. To determine if this pre-BL-CFC potential was specific to the GFP$^+$/Flk-1$^-$ fraction isolated at this stage of development, GFP$^+$/Flk-1$^-$ cells from different aged EBs were assayed for their ability to give rise to BL-CFC. As shown in FIG. 7A, the capacity to generate BL-CFC was most robust in the day 3 GFP$^+$/Flk-1$^-$ cells. This developmental potential decreased dramatically by day 3.5 of differentiation and was almost non-existent at day 4.0. The BL-CFC content of the freshly isolated GFP$^+$/Flk-1$^+$ fraction from these same EBs increased over this period of time, indicating that differentiation was progressing in a normal fashion. The Flk-1 expression patterns in the reaggregated cultures from the different staged EB cells were consistent with BL-CFC data. The cultures from the reaggregated day 3.0 GFP$^+$/Flk-1$^-$ cells contained a distinct Flk-1 fraction that represented more than 40% of the total population (FIG. 7B). Flk-1 expression in the day 3.5 and 4.0 cultures was significantly lower and consisted of a shoulder of the total population rather than a distinct peak.

EXAMPLE 7

Cardiomyocyte Potential of GFP and Flk-1 Subpopulations

Given the sequence of events in the mouse embryo in which the development of hematopoietic and endothelial mesoderm is followed by the development of cardiac and cranial mesoderm, the cardiomyocyte potential of the isolated populations was determined For this analysis, aggregates from the cultures of the different populations were transferred to microtiter or 24-well plates in serum-free medium and monitored for the development of beating cell masses, indicative of cardiomyocytes. These conditions are known to support the efficient development of cardiomyocytes from the reaggregated cells. As an independent confirmation of the cardiomyocyte nature of the cells within these masses, a representative group was transferred to microscope slides, fixed and stained for the presence of the cardiac-specific isoform of Troponin T. All beating cell masses analyzed were found to contain Troponin T positive cells indicating that they were cardiomyocytes. Using this assay, the cardiomyocyte potential of the reaggregated GFP$^+$/Flk-1$^-$ and GFP$^+$/Flk-1$^+$ fractions from different staged EBs was determined. For comparison, the BL-CFC potential of the freshly isolated GFP$^+$/Flk-1$^+$ cells and of the cultured GFP$^+$/Flk-1$^-$ cells was analyzed.

TABLE I

BL-CFC, pre-BL-CFC and cardiomyocyte potential of the GFP+/Flk-1− and GFP+/Flk-1+ fractions isolated from different staged EBs.

| | GFP$^+$ Flk$^-$ | | GFP$^+$ Flk$^+$ | |
| --- | --- | --- | --- | --- |
| EB Age | BL-CFC following culture | beating following culture | BL-CFC direct plating | beating following culture |
| 2.75 | +++ | − | + | − |
| 3.5 | + | ++ | +++ | − |
| 4.0 | +/− | ++ | +++ | − |

As shown in Table 1, the BL-CFC potential of the different fractions was similar to that observed in previous experiments. The GFP+/Flk-1+ cells isolated from the three different EB populations generated BL-CFC, with the highest number found at day 3.5 and 4.0. The pre-BL-CFC potential in the GFP+/Flk-1− cells was greatest at day 2.75 and decreased significantly at 3.5 and 4.0. The cardiomyocyte potential of the fractions showed a reverse pattern. A significant proportion (>80%) of the transferred aggregates from day 3.5 and 4.0 GFP+/Flk-1− cells generated beating cardiomyocytes. No beating cells were observed in the aggregates generated from the earliest (day 2.75) GFP+/Flk-1− cells. Beating cells were not detected in aggregates generated from the GFP+/Flk-1+ cells isolated from EBs at any of the three stages of development. The findings from this analysis are consistent with the notion that GFP+/Flk-1− cells isolated at different stages have different potentials. Those that develop early appear to have a hemangioblast fate, whereas those that develop later generate the cardiac lineage and possibly other populations. The GFP+/Flk-1+ populations appear to have lost the cardiomyocyte potential and may be restricted to the hemangioblast lineages. Given these findings, the early developing (day 2.75-3.0) GFP+/Flk-1− cells are referred to as pre-hemangioblast mesoderm whereas the population that develops between day 3.5 and 4.0 are referred to as pre-cardiac mesoderm. The day 3.0-3.5 GFP+/Flk-1+ populations generate BL-CFC, whereas those isolated from later stage EBs (day 4.0) contain primitive erythroid progenitors, indicating the onset of hematopoietic commitment. Given this developmental potential, the GFP+/Flk-1+ population is referred to as hemangioblast mesoderm.

Examples 5 and 6 demonstrate that GFP+ cells isolated from different aged EBs have different developmental potential. As indicated in the previous examples, GFP+/Flk-1− cells from day 3 EBs efficiently generate both hematopoietic and endothelial lineages. These cells did not give rise to cardiotiyocytes (heart tissue) as demonstrated by the lack of beating cell masses. In contrast, GFP+ cells from day 4 EBs gave rise to few Flk-1+ cells and BL-CFC following culture. This population did, however, generate cells of the cardiomyocyte lineage. These findings demonstrate that the GFP+ (brachyury+) fraction isolated from different aged EBs have become patterned to distinct populations with different developmental fates. In addition to the conditions used and potentials observed in the foregoing examples, other potentials may be observed by altering conditions and additives.

EXAMPLE 8

Role of Serum-Derived Factors

Figure 8A:
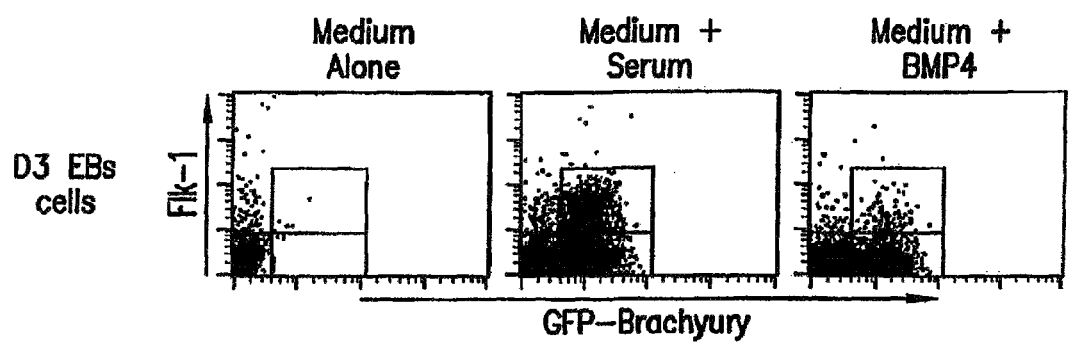
FIGS. 8A and 8B demonstrate the effects of BMP-4 and fetal calf serum (FCS) on the development of brachyury and Flk-1$^+$ in/on day 3.0 EB derived cells under the conditions indicated at the top of each histogram.
Figure 8B:
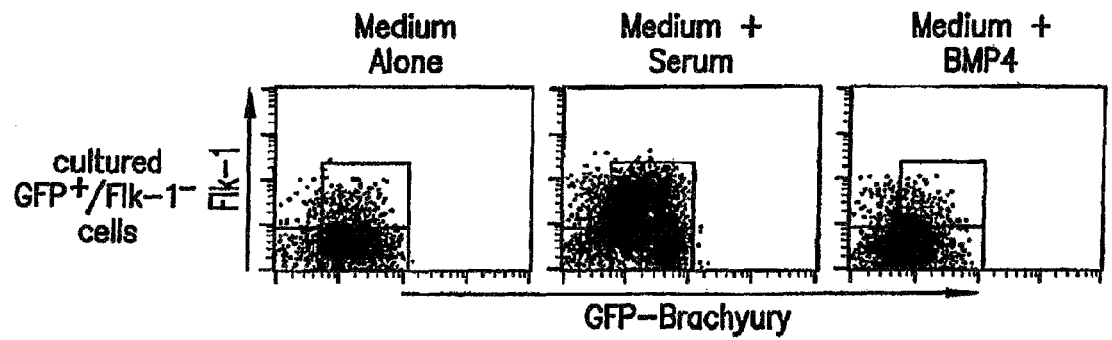

To assess the role of serum in the development of brachyury+ cells, EBs were differentiated the absence of serum. EBs did develop under these conditions, although they were somewhat smaller than those found in normal conditions. In the absence of serum, no GFP+ cells were detected within these EBs, indicating that mesoderm was not induced under these conditions (FIG. 8). Significant numbers of GFP+/Flk-1− and GFP+/Flk-1+ cells did develop when serum was added to the cultures. These findings clearly demonstrate that components found within serum are able to induce the development and differentiation of brachyury+ cells. As a first step in identifying factors that might play a role in this process, BMP4 (20 ng/ml) was added to the developing EBs in the serum free cultures. At this concentration, BMP4 did induce a significant population of brachyury+ cells within 3 days of differentiation. However, in contrast to the serum, BMP4 did not support the development of the GFP+/Flk-1+ population in this period of time. To determine if BMP4 could induce GFP+/Flk-1+ from GFP+/Flk-1− cells that were induced in the presence of serum, GFP+/Flk-1− cells were isolated from EBs differentiated for three days in the presence of serum. These cells were reaggregated in medium alone, in medium with serum or in medium with BMP4. As shown in the lower row of FIG. 8, GFP+/Flk-1− cells did not differentiate substantially when reaggregated in the absence of serum. As expected, the same population generated a large GFP+/Flk-1+ population when serum was added to the cultures. Consistent with the findings in the primary differentiation cultures, BMP4 was unable to induce the development of significant numbers of GFP+/Flk-1+ cells from the cultured GFP+/Flk-1− cells.

Figure 9:
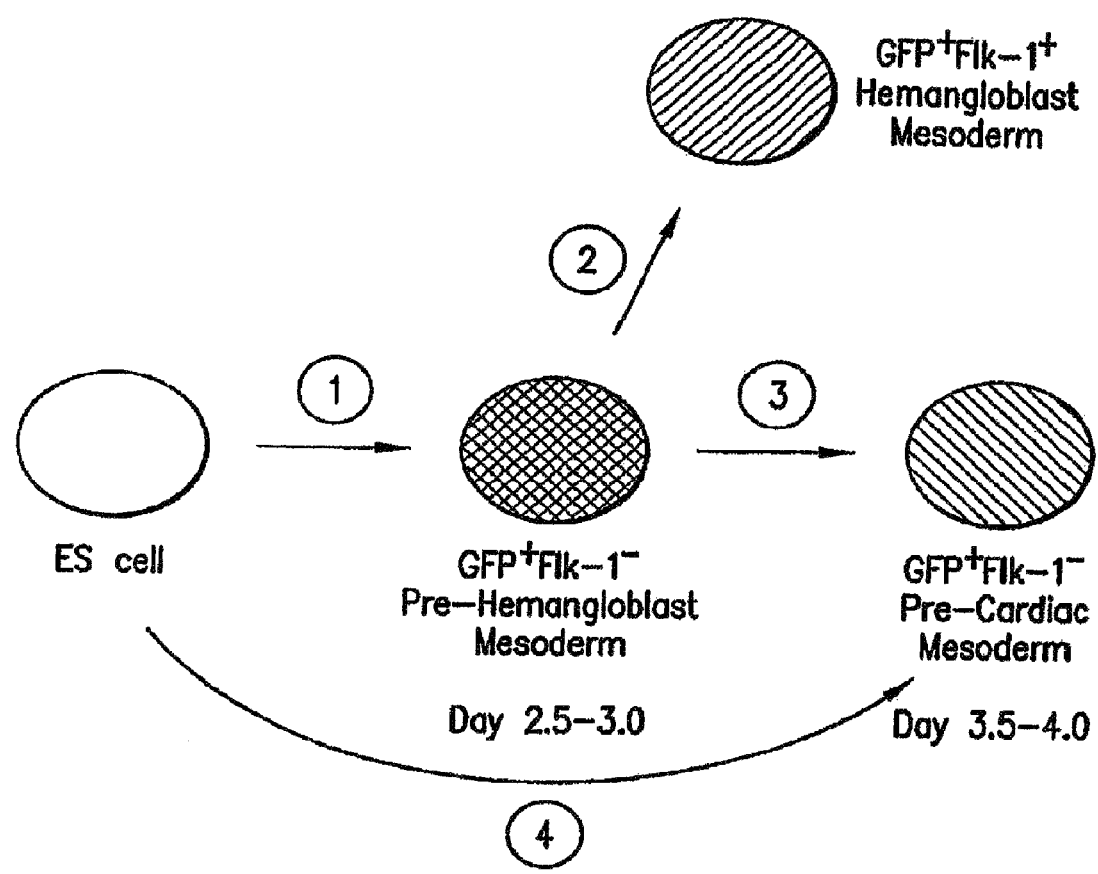
FIG. 9 is a schematic model of mesoderm formation and specification in EBs.

FIG. 9 summarizes the stages in mesoderm development based upon the foregoing examples. Step #1 represents mesoderm induction and patterning to a pre-hematopoietic and endothelial (pre-hemangioblast) fate. Step #2 represents specification to the hematopoietic and endothelial lineages. Steps #3 and #4 represent patterning to the pre-cardiac fate.

EXAMPLE 9

Isolation and Characterization of Endoderm Potential of Cell Populations

Figure 10:
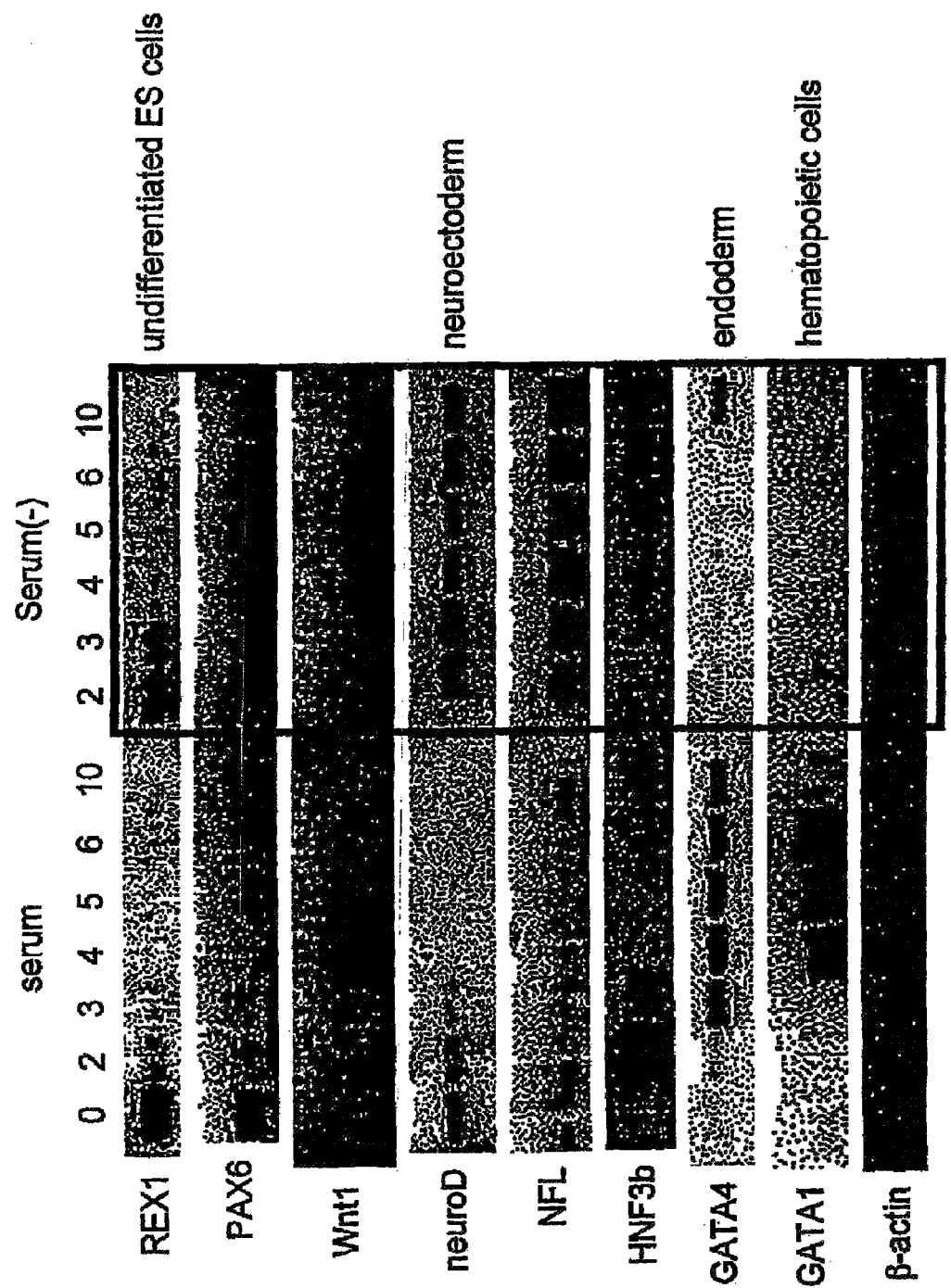
FIG. 10 shows the expression of genes in EBs in the presence and absence of serum.
Figure 11:
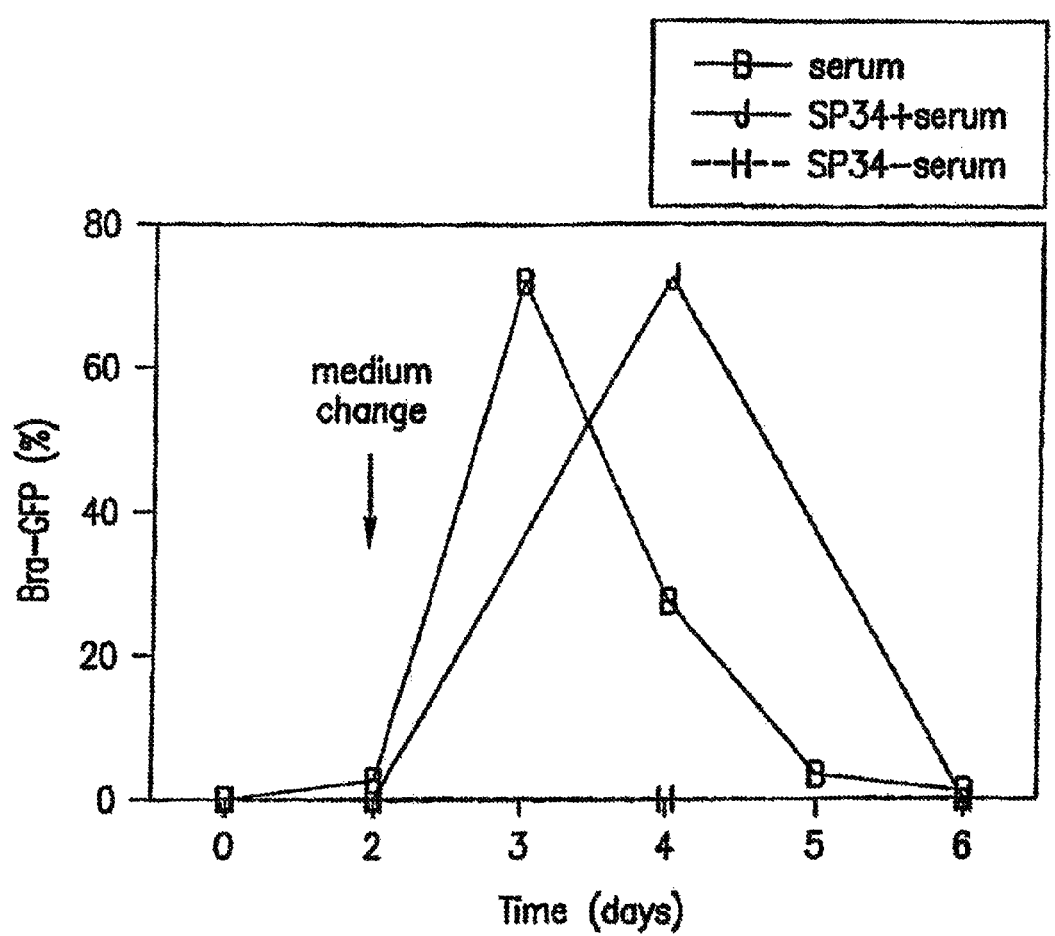
FIG. 11 is a graph depicting brachyury expression in EBs generated under different conditions.
Figure 12:
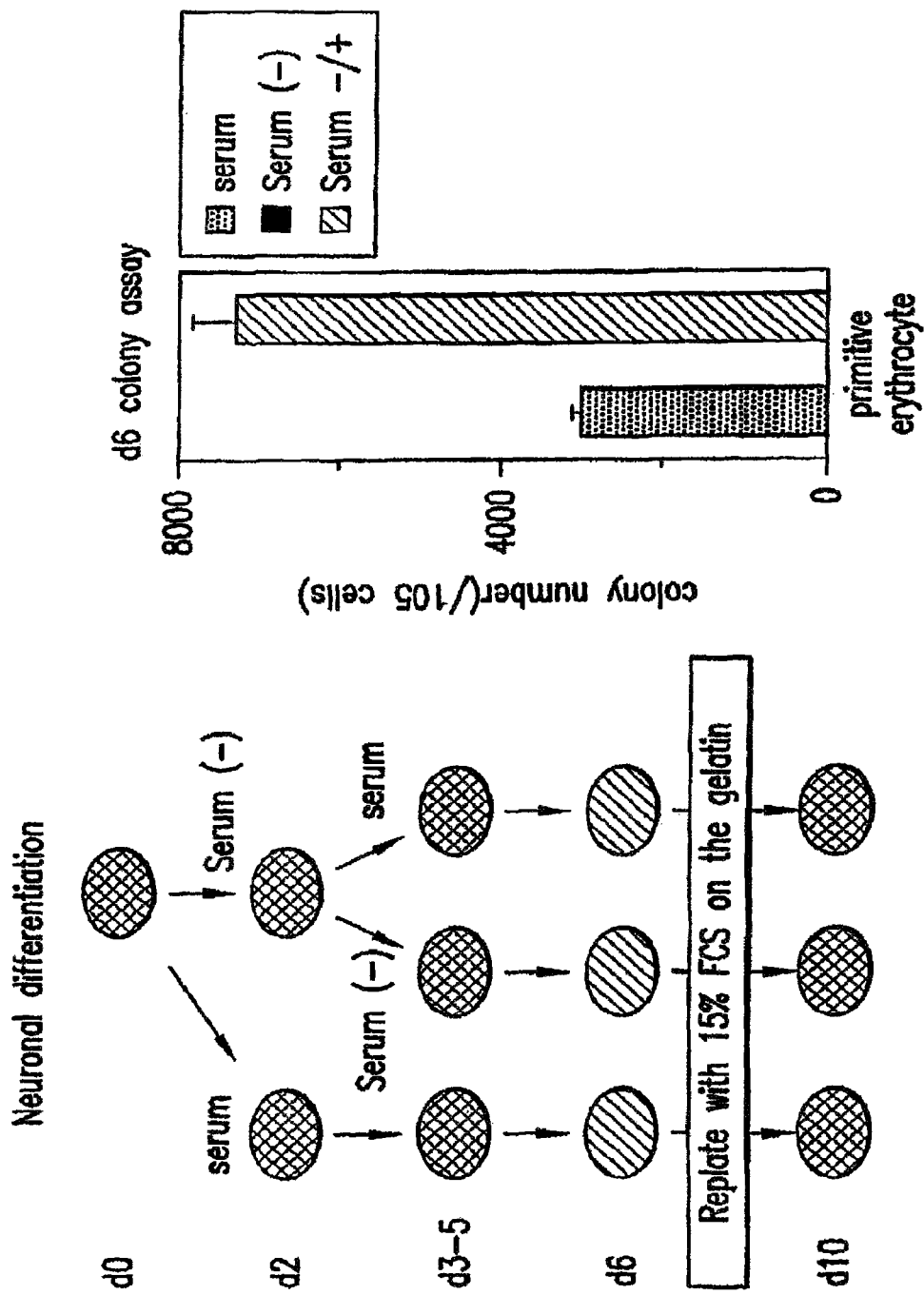
FIG. 12 shows that EBs grown in serum contained hematopoietic precursors, whereas those grown without serum did not.
Figure 13:
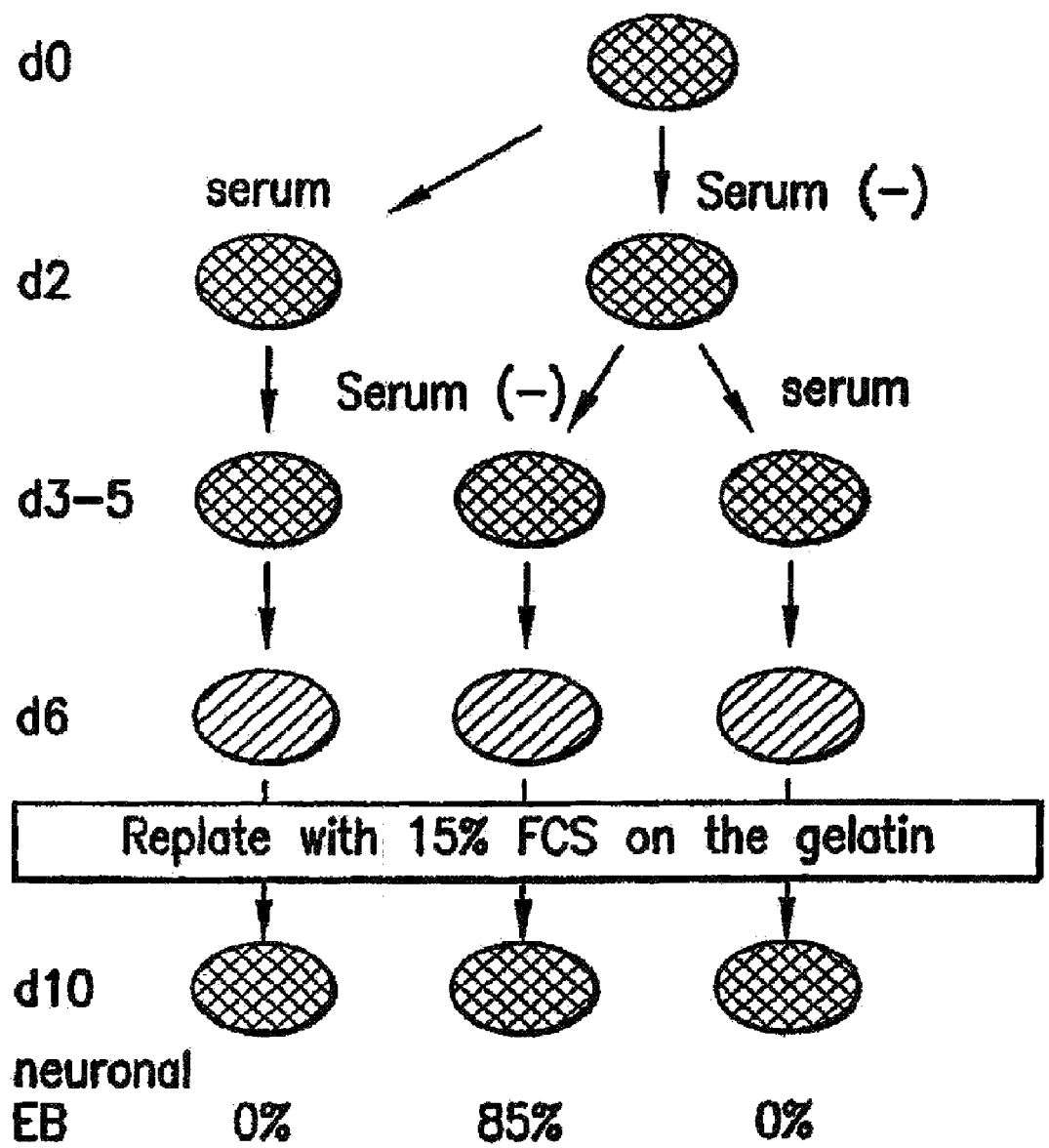
FIG. 13 is a schematic diagram showing neuronal differentiation is the presence and absence of serum.

Studies using model systems such as *Xenopus* and Zebrafish have suggested that mesoderm and endoderm develop from a common precursor population known as mesendoderm. To determine whether or not a mesendoderm stage of development does exist in EBs, conditions for the development of the endoderm lineage were established. As a first step in establishing culture conditions for the development of this lineage, the amount of serum in the differentiation cultures was varied. EBs were generated in the presence and absence of serum (SP34 and then IMDM plus SR) and assayed at different stages for expression of genes associated with ectoderm, endoderm and mesoderm development. For the ectoderm lineage, development of the neuronal lineage was assessed analyzing expression of PAX6, Wntl, neruoD and neurofilament (NFL). These genes are known to be expressed at different stages of neruonal development. The early stages of endoderm development were monitored by expression of HNF3β. To evaluate later stages of endoderm development and specification, genes involved in liver development were analyzed. These included Hex, α-fetoprotein (AFP), HNF4, Albumin (Alb), α-1-antittrypsin (AAT) and tyrosine aminotransferase (TAT). Mesoderm development was monitored by expression of brachyury and GATA-1. In addition to gene expression patterns, neuronal development was assayed by monitoring neurite outgrowth from EBs. The neuronal nature of these neurites was demonstrated by βIII-Tubulin expression. Mesoderm development was also assessed by enumeration of hematopoietic progenitors in the EBs. FIG. 10 shows the impact of serum on the developmental potential of EBs over a 10-day differentiation period. In the presence of serum (serum) there is little neuro-ecotderm differentiation as demonstrated by the lack of expression of the genes associated with development of this lineage. HNF3β is expressed at early stages of differentiation (day 2-3) and then downregulated. As expected, GATA-1 is expressed in the EBs generated under these conditions. The pattern of expression of these genes was basically reversed in EBs grown in the absence of serum (serum-). These EBs expressed all the genes associated with neuroectoderm, but did not express the mesoderm/hematopoietic marker GATA-1. HNF3β was expressed in late stage EBs (day 10) grown under these conditions. The patterns of brachyury expression as monitored by GFP expression were consistent with these findings. EBs generated in the presence of serum generated a substantial brachyury$^+$ population that was present between days 2 and 5 of differentiation (FIG. 11,-B-line). Brachyury was not detected in EBs grown in the absence of serum (FIG. 11,-H-line). Hematopoietic precursor assays confirmed these findings. EBs generated in serum contained precursors (FIG. 12, speckled bar), whereas those grown without serum did not (FIG. 12, solid bar, not visible). Finally, evaluation of neurite potential of the EBs was consistent with these various analyses. None of the EBs grown in serum generated neurites. In contrast, 85% of those generated in the absence of serum displayed this activity (FIG. 13). Taken together, these findings demonstrate the importance of culture conditions (serum) for the generation of specific lineages. They also demonstrate that neither serum complete—nor serum-free—conditions were optimal for endoderm development.

Figure 14:
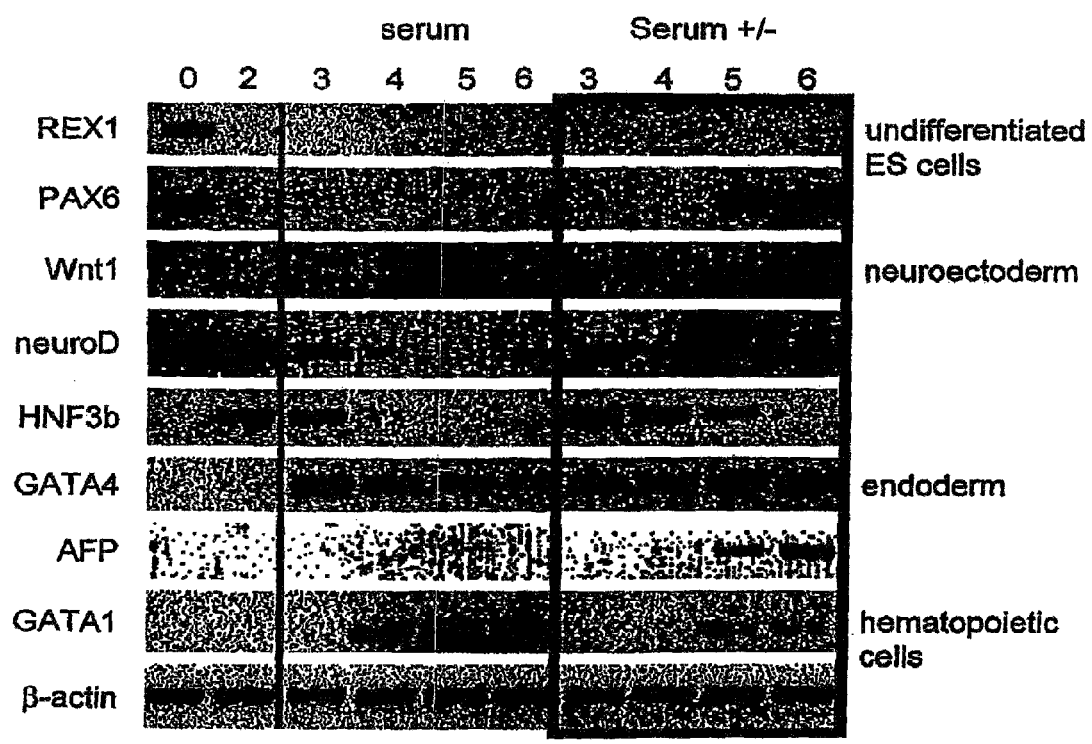
FIG. 14 shows the expression of genes in EBs initiated for two days in serum and then switched to serum free conditions.
Figure 15:
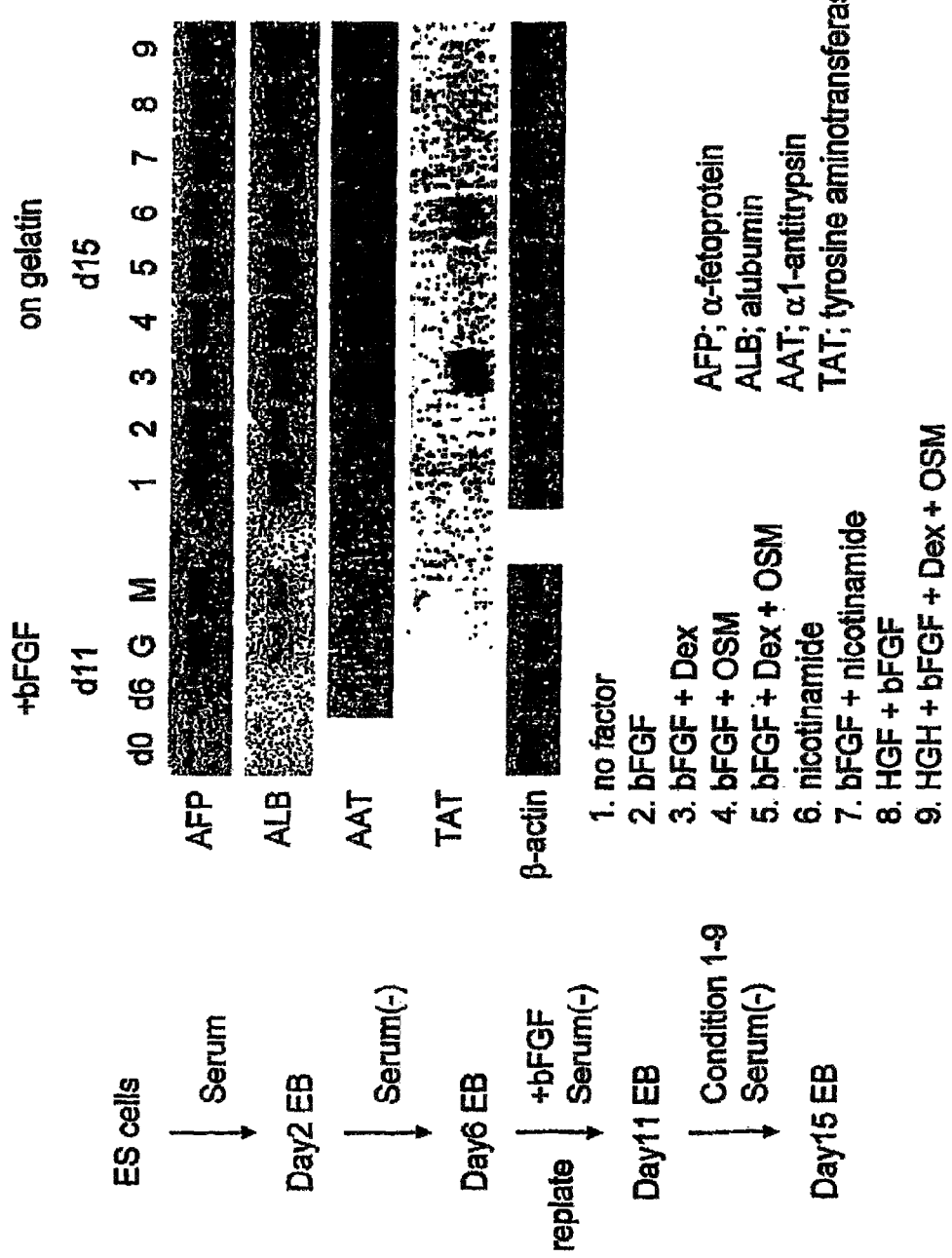
FIG. 15 shows gene expression in EBs cultured in the presence of bFGF.

The strong upregulation of HNF3β in the early stage EBs generated in serum suggested that serum might be important for the establishment, but not the maturation of the endoderm lineage. To test this possibility, EBs were initiated for 2 days in the presence of serum and then switched to serum-free conditions (SR). As shown in FIG. 14, EBs generated under these conditions (serum+/−) expressed HNF3β between days 3 and 5 of differentiation. AFP was upregulated at day 5 of differentiation. GATA-1 expression levels were reduced compared to those found in serum-stimulated EBs. Next, day 6 EBs generated under the serum+/− conditions were plated in tissue culture grade dishes (to allow them to adhere) in the presence of the growth factor bFGF. The dishes were coated with either gelatin or matrigel to determine if substrate had any impact on further endoderm differentiation. Five days later, the medium was changed and additional factors were added to these cultures to promote the development of the liver lineage. The experimental outline and data are shown in FIG. 15. In this experiment AFP was not expressed at the day 6 EB stage. Its levels of expression were upregulated when cultured in the presence of bFGF on either gelatin of matrigel. Low levels of ALB were also detected at this stage. ALB expression increased following the additional culture period in all conditions tested. AAT and TAT were also expressed following the last culture step. The highest levels of TAT were found when EB-derived cells were cultured in the presence of bFGF and Dex. These findings clearly indicate that it is possible to generate cells of the endoderm lineage and that under appropriate conditions, they will give rise to cells that express genes associated with the developing liver.

Figure 16:
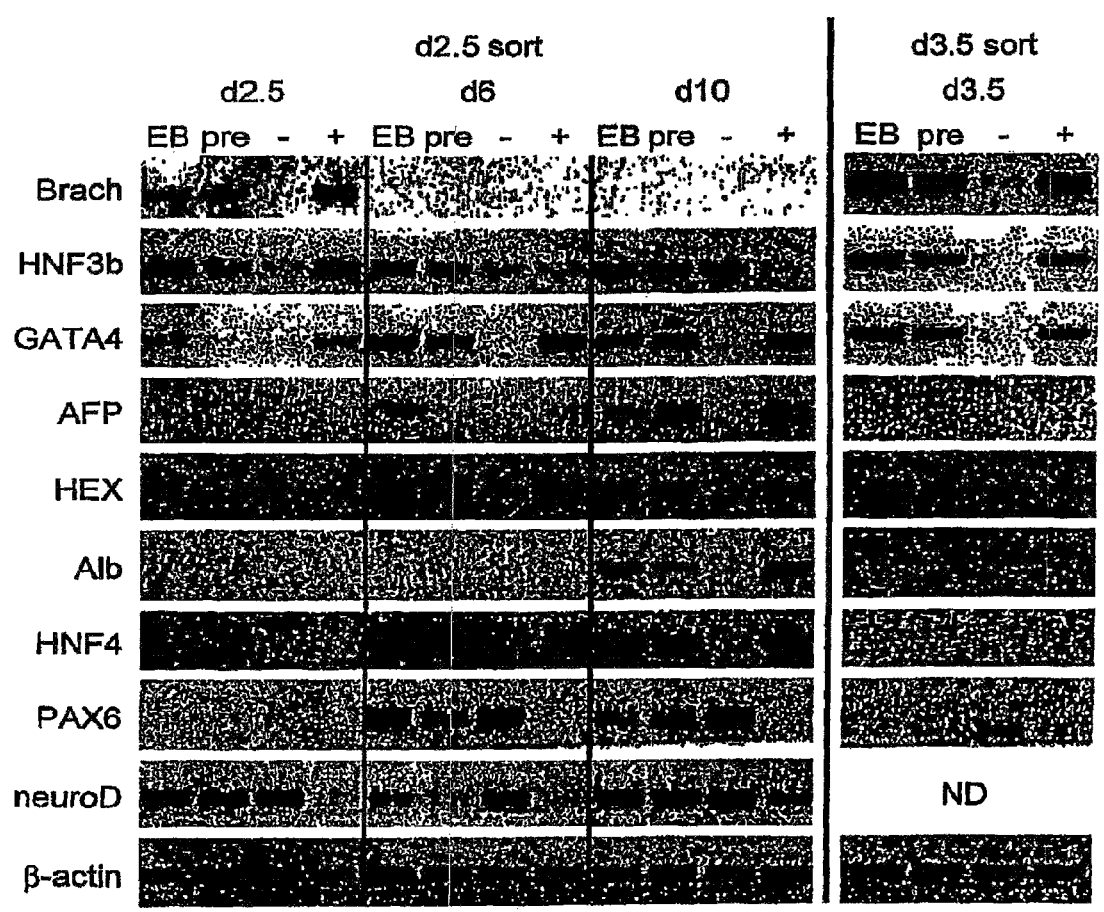
FIG. 16 shows gene expression patterns in Bry$^+$ and Bry$^-$ cells cultured in the presence of bFGF.

It was further determined if these endodermal cells developed from brachyury$^+$ or brachyury$^-$ cells. To address this question, GFP (Bry)$^+$ and GFP (Bry)$^-$ cells were isolated from day 2.5 EBs by cell sorting. These populations were allowed to reaggregate and cultured as clusters until day 6. On day 6, they were moved to the tissue culture grade dishes in medium with bFGF for 4 days (total of 10 days). Gene expression analysis indicated that cells, which express HNF3β, segregated to the GFP$^+$ fraction (d2.5) (FIG. 16). With time in culture, this gene was expressed in cells generated from the GFP$^-$ fraction. This likely reflects the fact that at later stages of expression HNF3β is expressed in non-endodermal population. AFP, HEX, ALB and HNF4 were all expressed in derivatives of the GFP$^+$ fraction, but not in cell populations generated from the GFP$^-$ cells. In contrast, PAX6 and neuroD, markers of neuroectoderm, were found predominantly in cells generated from the GFP$^-$ fraction. These findings indicate that the endoderm lineage is established from a brachyury$^+$ population, which also gives rise to the mesodermal lineage, and that these lineages derive from a common precursor, the mesendoderm.

To further evaluate the liver potential of the brachyury expressing cells, cell populations derived from both the bry$^+$ and bry$^-$ fractions were analyzed for expression of genes representing early hepatocyte development such as α-feto-protein (AFP), albumin (ALB) and transthyretin (TTR) and genes indicative of maturation of the lineage including alpha1-antitrypsin (AAT), tyrosine aminotransferase (TAT) and carbamoyl phosphate synthetase I (CPase). β-actin expression was used as a control. Cells were analyzed prior to sorting and subsequent to sorting into bry$^+$ and bry$^-$ populations. Fetal liver and adult liver controls were also analyzed. Expression of all of these genes was restricted to the cells derived from the bry$^+$ population, indicating that cells with hepatocyte characteristics develop from brachyury expressing cells.

EXAMPLE 10

Kinetics of Mesoderm and Endoderm Development in EBs

Figure 18:
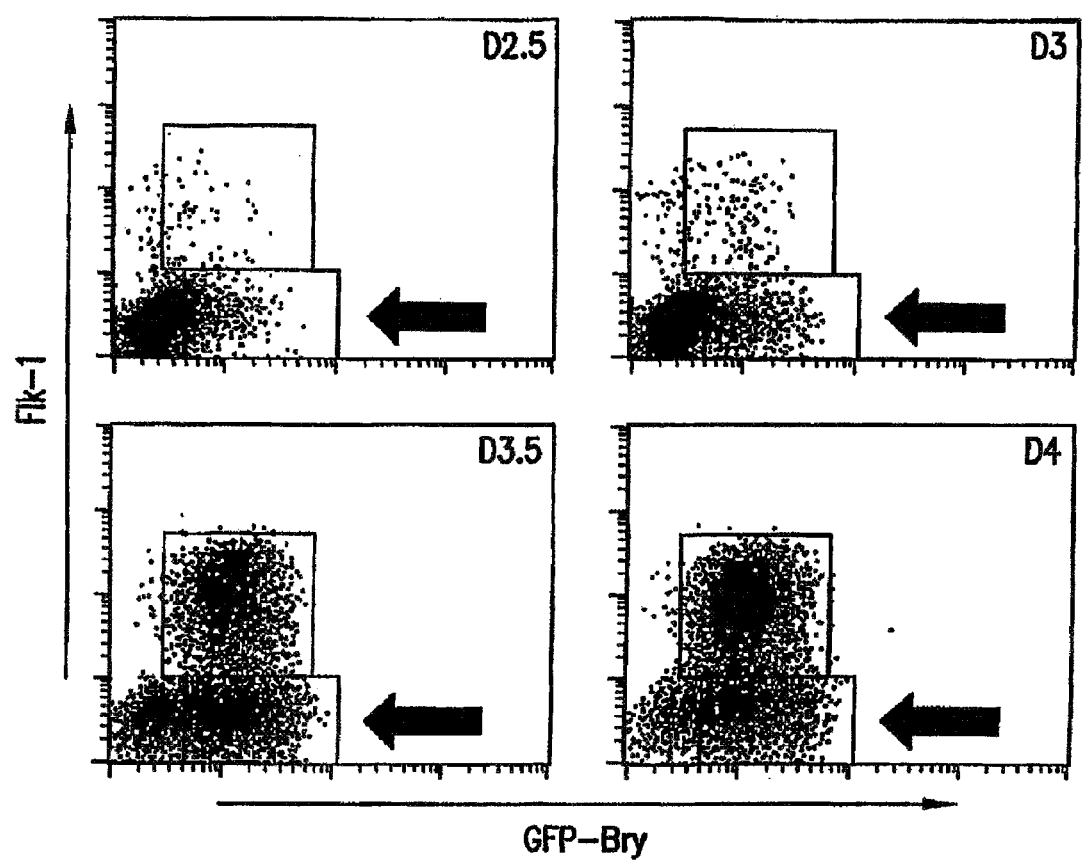
FIG. 18 depicts the kinetics of expression of GFP (brachyury) and Flk-1 in EBs differentiated for 2.5, 3.0, 3.5 and 4.0 days. Arrows indicate the GFP$^+$ population isolated used for the analyses in subsequent studies.
Figure 19:
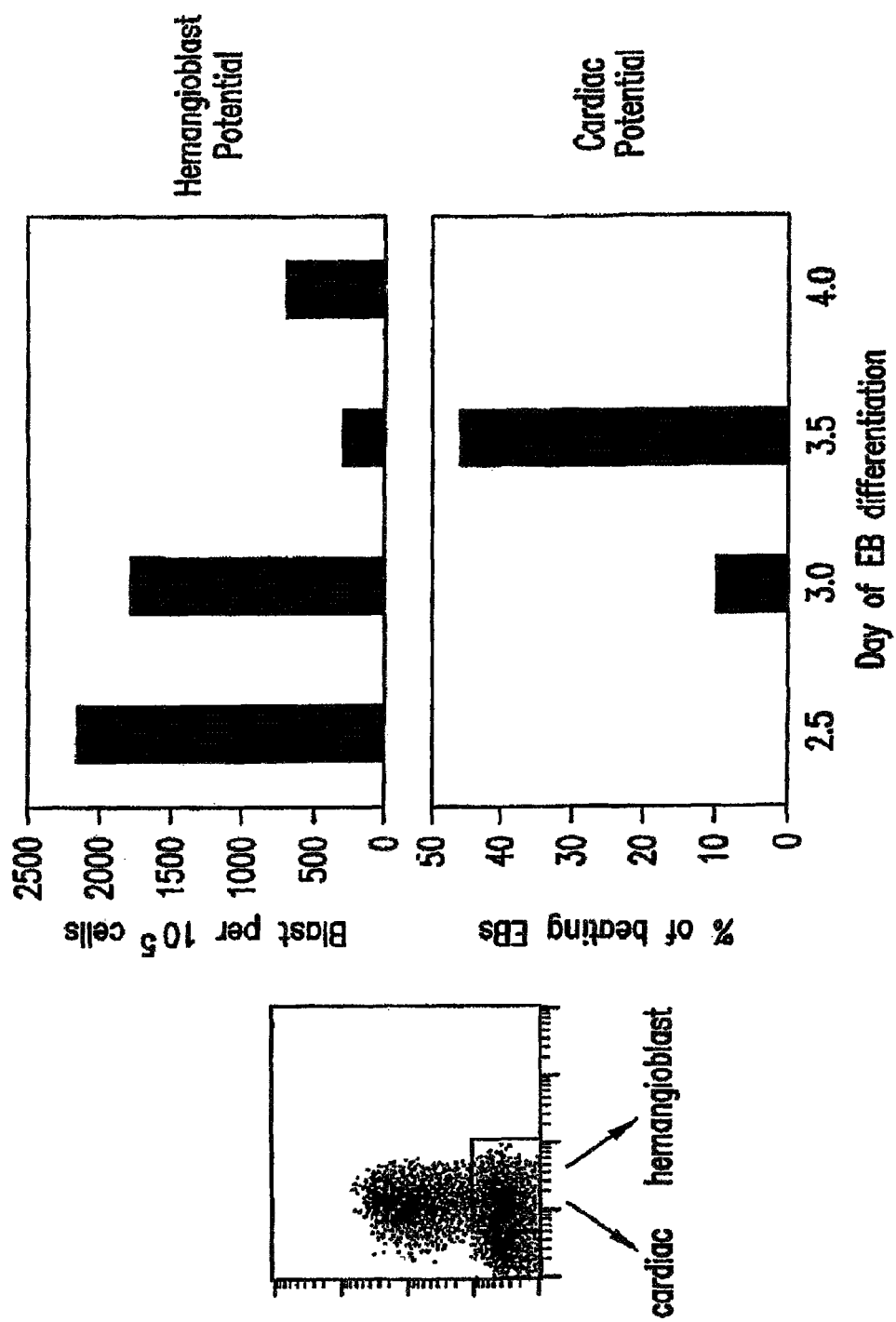
FIG. 19 depicts the hemangioblast and cardiac potential of the GFP$^+$ populations isolated from the four stages of EB differentiation. Cells from each stage were isolated by cell sorting, reaggregated for 24 hours and analyzed for hematopoietic and cardiac potential. Data are indicated as blast colonies (hemangioblast) per 1×10$^5$ cells recovered from the reaggregation culture or as the % of aggregates that gave rise to beating cell masses indicative of cardiac muscle differentiation.
Figure 20:
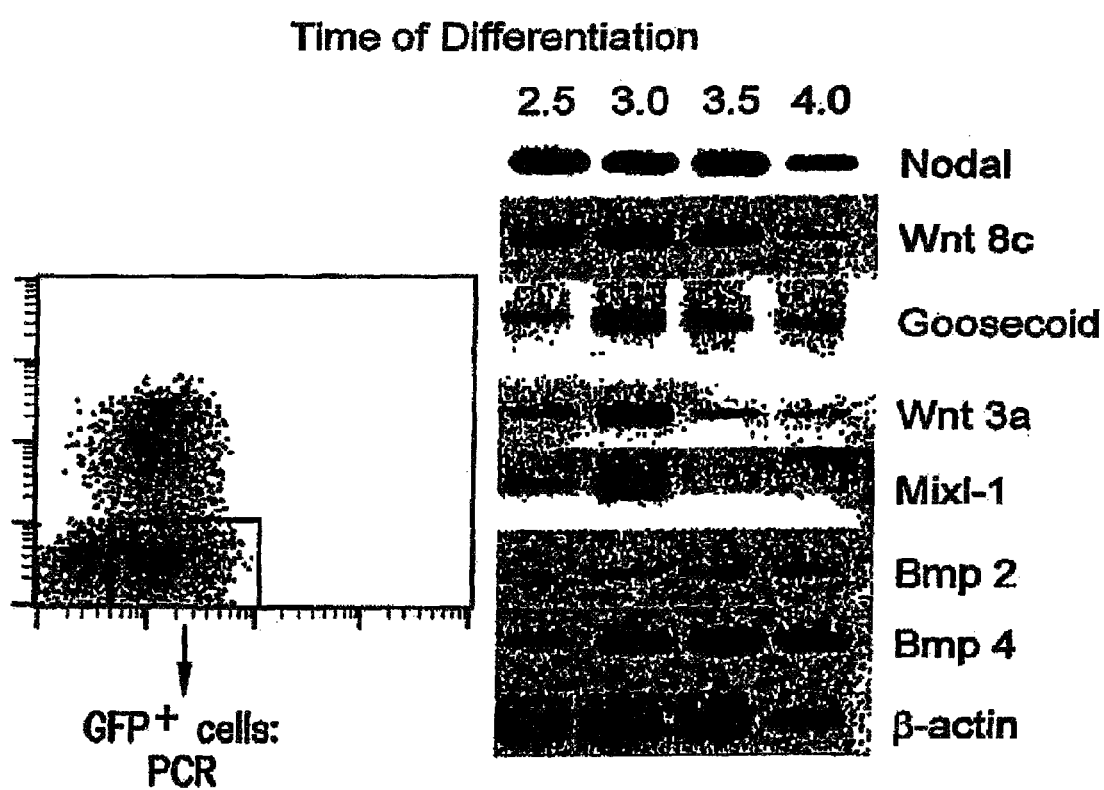
FIG. 20 provides the RT-PCR expression analysis of the indicated genes in the four GFP$^+$ EB-derived cells populations. Numbers indicate day of EB differentiation.

The preliminary kinetic analysis described in Example 6 demonstrated that subpopulations of mesoderm with distinct developmental fates were generated in a defined temporal fashion. A more detailed kinetic analysis showed the dynamic development of the GFP$^+$Flk1$^-$ (hereafter referred to as the GFP$^+$ population) population between days 2.5 and 4.0 of differentiation (FIG. 18). When isolated and reaggregated, the day 2.5 and 3.0 GFP$^+$ fractions generated blast cell colonies (indicated as hemangioblast potential in FIG. 19) that represent the earliest stages of hematopoietic and endothelial commitment (FIG. 19). This population of GFP$^+$ cells displayed little cardiomyocyte (cardiac) potential. In contrast to the early GFP$^+$ cells, those isolated from day 3.5 EBs showed significantly reduced BL-CFC potential, but were efficient at differentiating into cardiomyocytes. GFP$^+$ cells isolated from day 4 EBs did not give rise to cardiomyoctes and had little capacity to generate BL-CFC, suggesting they may be fated to some other mesodermal lineage. Gene expression analysis supported these functional assays and demonstrated molecular differences between the four GFP$^+$ fractions (FIG. 20). While some genes were expressed in all populations, others showed intriguing differential patterns. Wnt3a, a gene thought to be important for hematopoietic development and inhibitory for cardiac differentiation, was expressed in the day 2.5 and 3.0 populations and down regulated in the day 3.5 and 4.0 cells. This pattern is consistent with the change in developmental potential of these populations from hematopoietic/vascular to cardiac muscle. A second pattern of interest is that of the gene Mixl-1. This gene, which plays a role in the development of mesoderm and endoderm, was expressed in the day 2.5 and 3.0 GFP populations but not in the day 3.5 and 4.0 fractions. Taken together, the findings of this example clearly demonstrate that mesoderm populations with different developmental potential are generated in a defined temporal pattern within the EBs. In addition, expression analysis of the mesoderm/endoderm gene Mixl-1 indicates that cells with endoderm potential are also generated at a specific time, namely between day 2.5 and 3.0 of differentiation.

Figure 21:
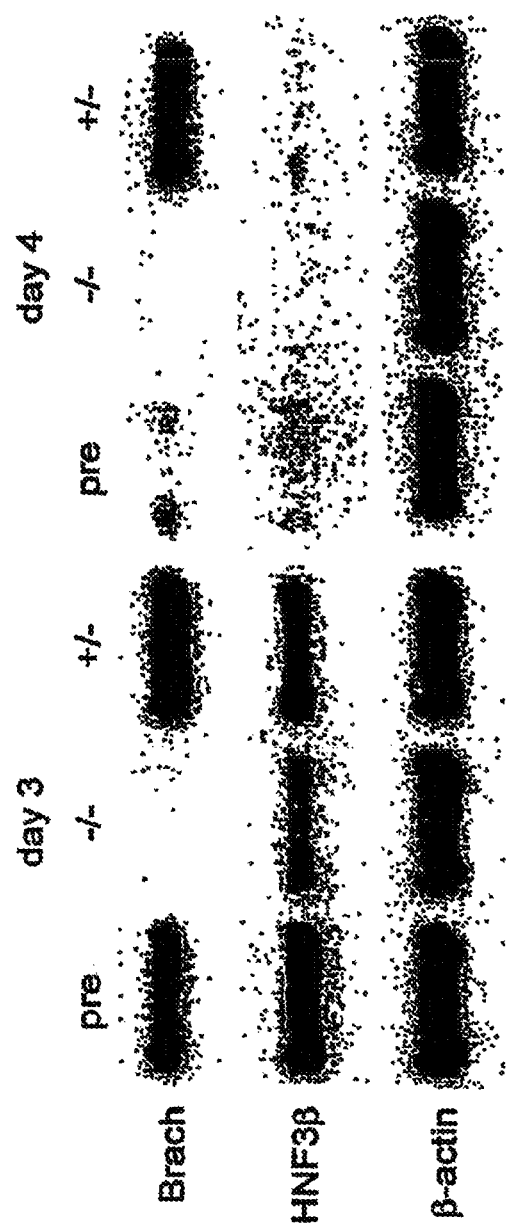
FIG. 21 shows HNF3 β expression in GFP$^+$ populations isolated from day 3.0 and 4.0 EBs. Pre represents cells prior to sorting, –/– are cells that express no GFP or Flk-1 and +/– represents the GFP$^+$ Flk-1$^-$ population.

To further investigate the kinetics of endoderm development, GFP+ cells from day 3.0 and 4.0 EBs were isolated and cultured under conditions that promote the differentiation into hepatocyte-like cells. As shown in FIG. 21, GFP+ cells (+/−) isolated from day 3.0 but not those from day 4.0 displayed endoderm potential as defined by expression of HNF3β. These findings indicate that endoderm is generated within the GFP+ population at a specific period of time, prior to day 4 of differentiation.

EXAMPLE 11

Developmental Potential of GFP+ Populations In Vivo

To further evaluate the endoderm potential of the GFP+ population, GFP+ and GFP− day 2.5 EB cells were cultured for 14 day days under conditions known to promote hepatocyte differentiation and then transplanted under the kidney capsule of recipient SCID-beige mice. Several mice were sacrificed immediately following the transplant, the kidney with the graft was sectioned and the sections were stained with antibodies against Hep1 and AFP. Hep1 is a specific marker of hepatocytes whereas AFP is expressed in definitive endoderm and immature cells of the hepatocyte lineage. Some of the cells within the section stained positive for Hep1, whereas other cells, in the vicinity of the Hep1+ cells were found to express AFP. No Hep1+ or AFP+ cells were found in the graft of the GFP− negative cells. These findings support PCR data and demonstrate that there culture conditions support the development of cells with characteristics of immature hepatocytes, as defined by express of Hep1.

While these transplantation experiments demonstrate the presence of hepatocyte-like cells in the grafts immediately following transplantation, it was difficult to monitor the maturation of these populations over time, as the transplanted tissues generated tumor-like masses known as teratomas. The teratomas likely develop from contaminating undifferentiated ES cells or from GFP+ primordial germ cells that are known to be of mesoderm origin and to express brachyury.

EXAMPLE 12

Induction of Mesoderm and Endoderm by Activin

Figure 22A:
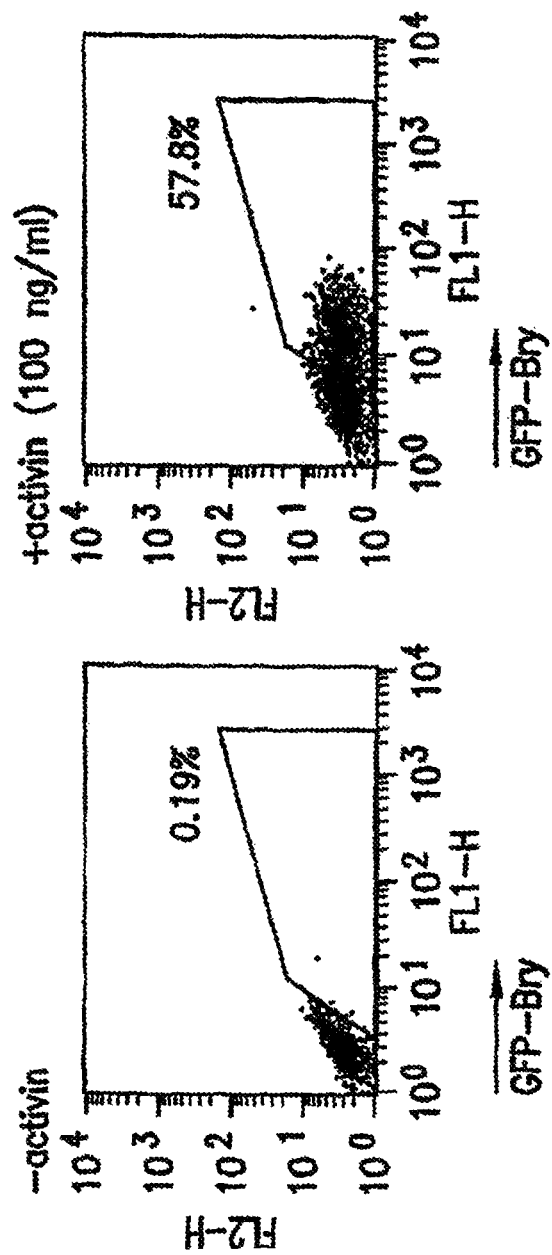
FIGS. 22A, 22B and 22C demonstrate the effects of activin on development of EBs in serum-free cultures. A) FACS profile showing GFP expression in day 6 EBs differentiated in the presence of 100 ng/ml of activin. B) Kinetics of GFP induction in cultures containing 100 ng/ml of activin. Open circles are EB differentiated in the presence of activin, closed squares are EBs differentiated in absence of activin. C) RT-PCR expression analysis of indicated genes in day 6 EBs grown in the presence (+activin) or absence (–activin) of activin. Numbers indicate day of EB differentiation.
Figure 22B:
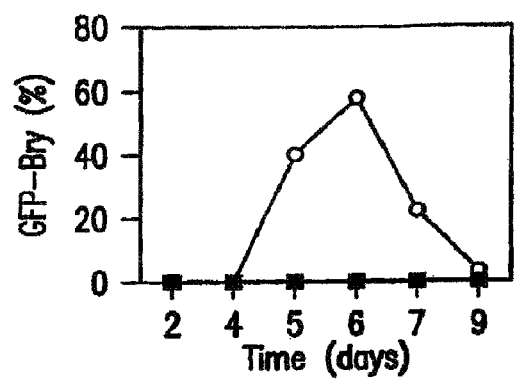
Figure 22C:
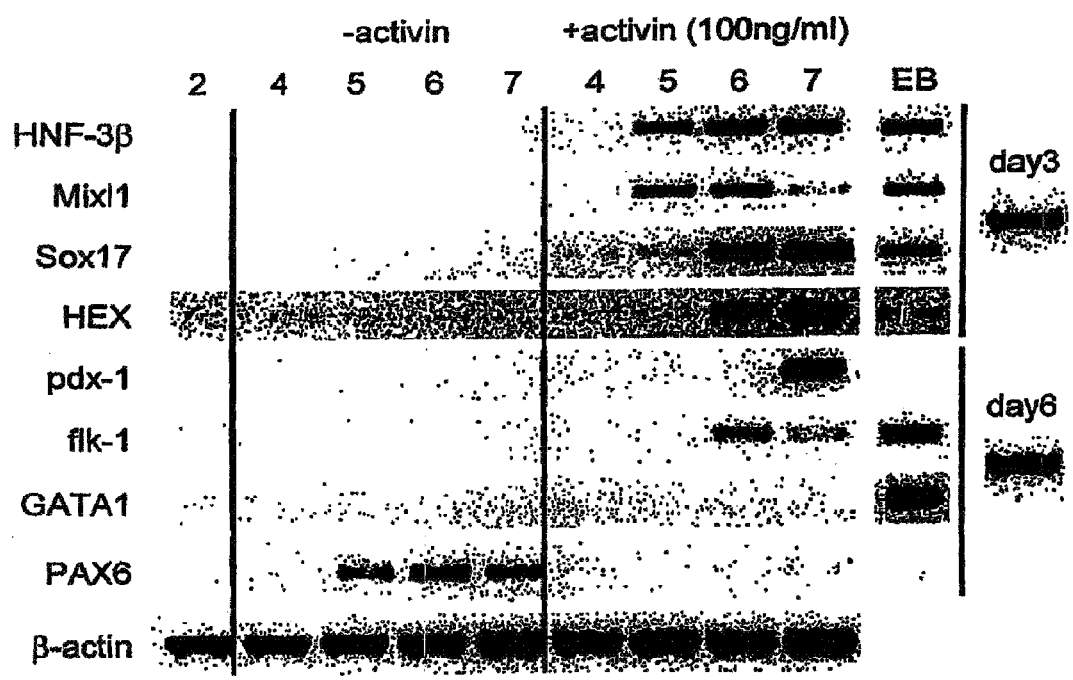

To further enrich for cells with endodermal potential, the effects of growth factors known to induce this cell population in other model systems were tested. Studies in *Xenopus* have shown that activin will induce both mesoderm and endoderm from ectoderm in culture. Of particular interest was the observation that activin behaved as a morphogen in this model in that it induced different cell types at different concentrations used. To determine if activin displayed similar potential in the ES/EB system, it was added to the EB cultures using the following protocol. ES cells were differentiated for 2 days in Stem Pro 34 medium without serum. At this stage, the developing EBs were harvested and recultured in IMDM supplemented with serum replacement (serum free) and activin at a concentration of 100 ng/ml. EBs were harvested at different days and assayed for GFP+ expression and expression of genes indicative of ectoderm, mesoderm and endoderm development. As shown in FIG. 22A,B this amount of activin-induced brachyury as measured by GFP. While the kinetics of GFP induction was delayed compared to EBs differentiated in serum, this concentration of activin did induce substantial numbers of brachyury positive cells (60%) by day 6 of differentiation. Molecular analysis indicated that the activin-induced cells expressed a broad spectrum of genes associated with endoderm development including HNF3β, Mixl-1, Soxl7, Hex-1, and pdx-1 (FIG. 23C). Induction of pdx-1 is of interest, as this gene is essential for pancreas development. Genes associated with hematopoietic development, such as GATA-1 and those indicative of neuroectoderm differentiation such as PAX6 were not induced by activin.

Figure 23A:
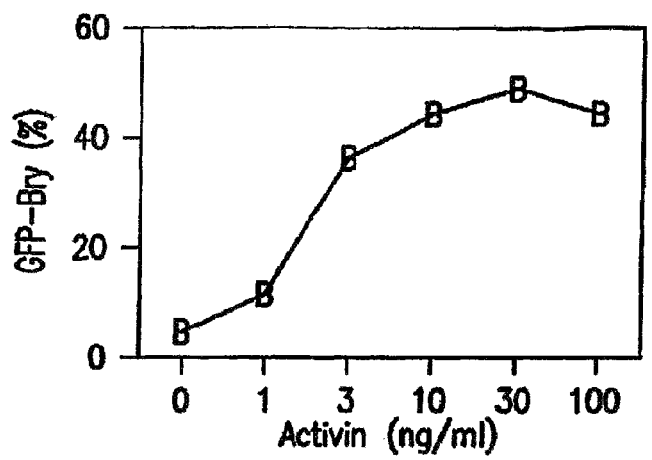
FIGS. 23A and 23B show the effects of different concentrations of activin on the developmental potential of EBs. A) GFP expression in day 7 EBs induced with different concentrations of activin. B) RT-PCR expression analysis of day 7 EBs induced with different concentrations of activin.

To determine if activin displayed morphogenic properties in the ES differentiation model, different concentrations of the factor were added to the EB cultures. As little as 1 ng/ml of activin induced GFP+ expression (10% of the total population) by 7 days of culture (FIG. 23A). The frequency of GFP+ cells increased to 40% in cultures stimulated with 3 ng/ml and reached plateau levels of greater than 50% at 30 ng/ml. Gene expression analysis of these populations indicated that different concentrations of activin did induce different developmental programs. EB differentiated in the presence of 1 or 3 ng/ml of activin showed weak, if any, expression of the genes indicative of endoderm development (FIG. 23A). HNF3β, Soxl7, Hex-1 were all induced in cultures stimulated with 10, 30, or 100 ng/ml of activin. Pdx-1 expression required the highest amount of activin and was induced best in EBs stimulated with 100 ng/ml. Neither GATA1 nor c-fms was expressed at any concentration of activin. The pattern of PAX6 expression was the reverse to that of the endoderm genes and was downregulated with increasing concentrations of activin.

Figure 24A:
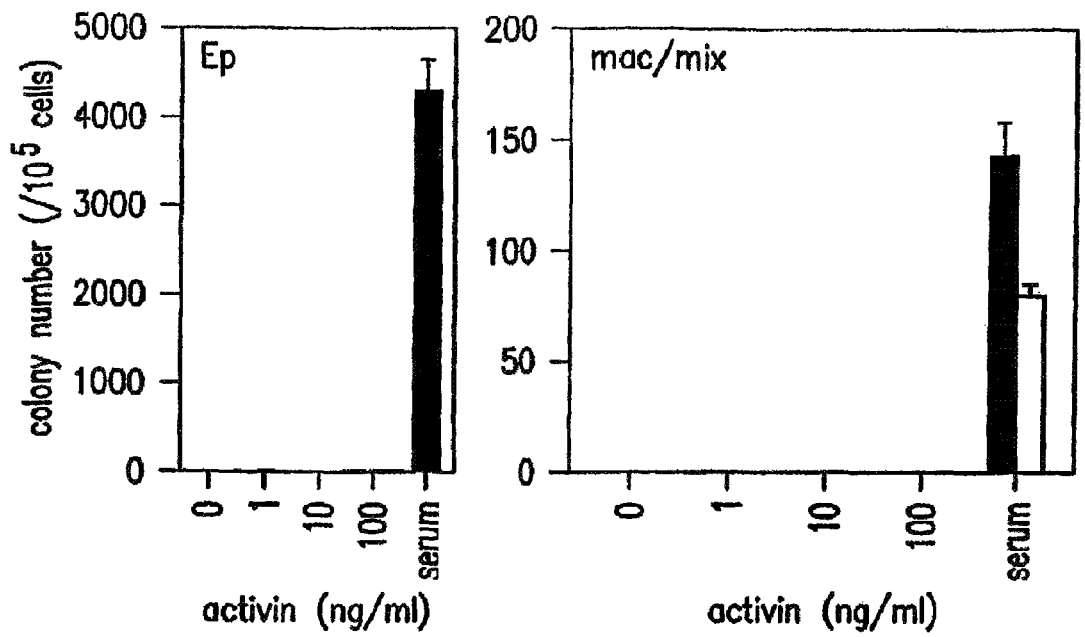
FIGS. 24A and 24B show the hematopoietic progenitor content of EBs differentiated in the presence of different concentrations of activin. A) Progenitor potential of day 7 EBs, Ep are primitive erythroid progenitors, mac/mix represent definitive hematopoietic progenitors. B) Progenitor potential of day 7 activin-induced EBs following 2.5 days of exposure to serum.
Figure 24B:
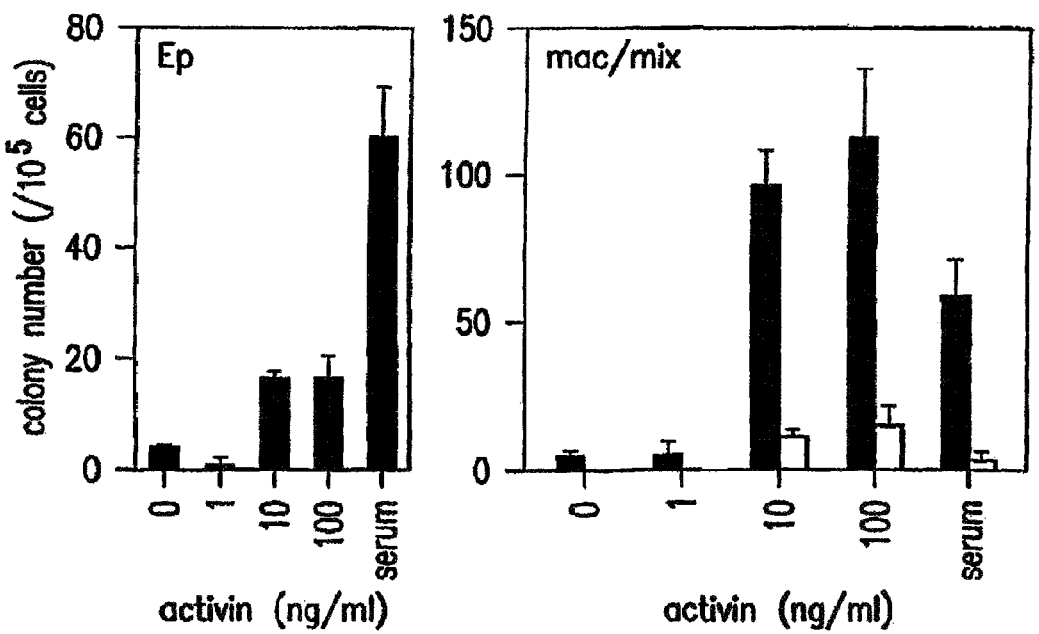

Activin-induced EBs did not express genes associated with hematopoietic commitment indicating that this developmental program was not induced. To further evaluate the hematopoietic potential of these EBs, they were analyzed for progenitor potential. As expected from the molecular analysis, these EBs contained no appreciable numbers of primitive (Ep) or definitive (mac/mix) hematopoietic progenitors (FIG. 24A). When these activin induced EBs were further stimulated with serum for 2.5 days, however, they did generate some hematopoietic progenitors, indicating that they do contain mesodermal potential (FIG. 24B).

PCR analysis demonstrated that activin induced expression HNF3β as well as other genes known to be involved in endoderm differentiation. To better estimate the proportion of endodermal progenitors in the activin-induced EBs, cells from cultures stimulated with 100 ng/ml activin were stained with antibodies against HNF3β and Hex1. EBs from un-induced cultures were used as controls (Activin-). A significant portion of the activin induced population (estimated at 50-60% of total) expressed both HNF3β and Hex1. None of the cells in the un-induced EBs expressed these proteins. These findings clearly demonstrate that a substantial number of cells within these EBs are of the endoderm lineage.

Figure 25:
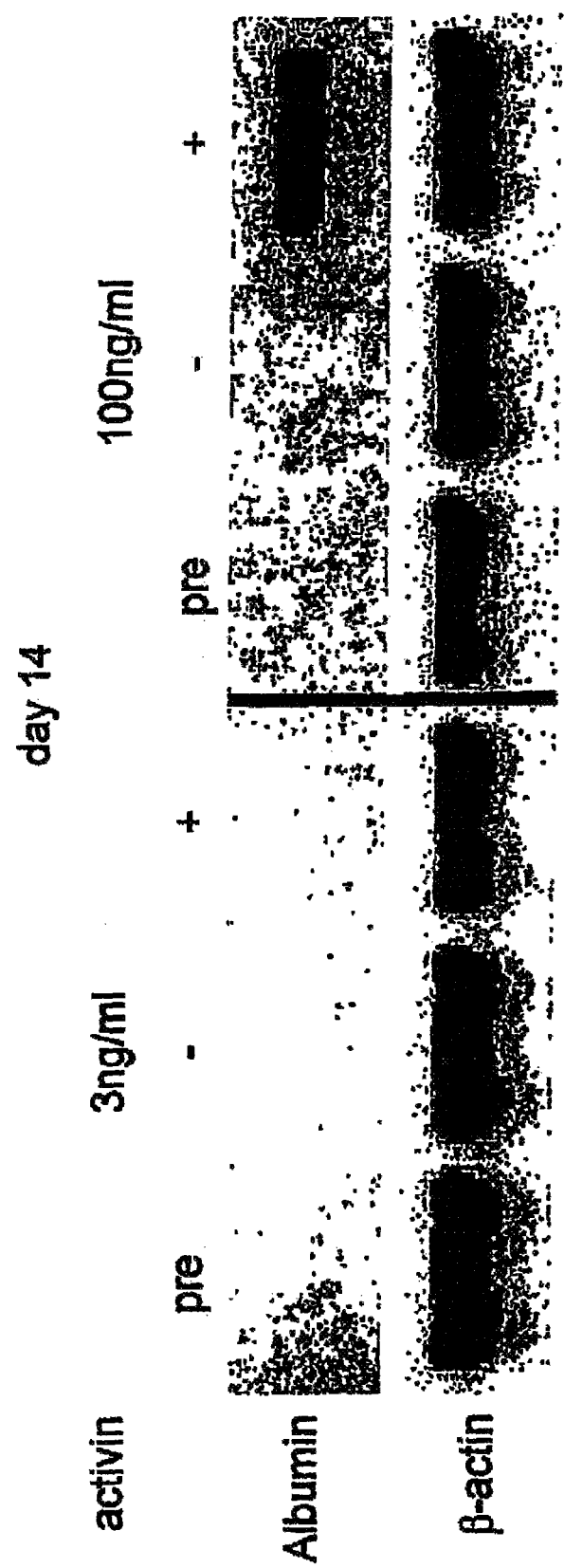
FIG. 25 shows the development of albumin expressing cells from GFP$^+$ cells induced with ether 3 or 100 ng/ml of activin. GFP$^+$ and GFP$^-$ cells were isolated at day 6 of differentiation and cultured for a further 8 days in the conditions previously described to support hepatocyte differentiation.

To further investigate the potential of these activin-induced populations, GFP+ cells were isolated from EBs stimulated with 3 ng or 100 ng and cultured further (14 day total) in hepatocyte conductions. As shown in FIG. 25, only cells from the 100 ng cultures differentiated into cells that expressed albumin consistent with liver differentiation. Taken together, the findings from these studies indicate that activin functions as a morphogen in the ES/EB system and that high concentration are required for endoderm induction.

Figure 26A:
FIGS. 26A and 26B depict three-week old renal grafts of bry+ (FIG. 26A) and bry− (FIG. 26B) cell populations.
Figure 26B:
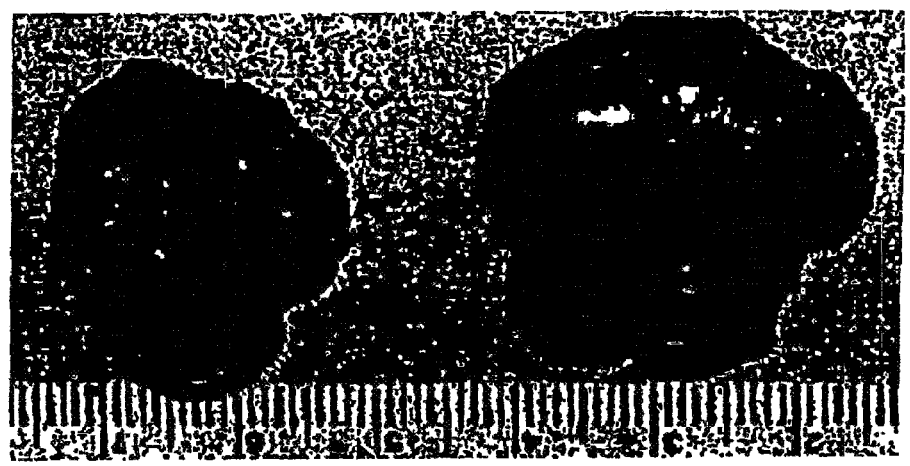
Figure 26C:
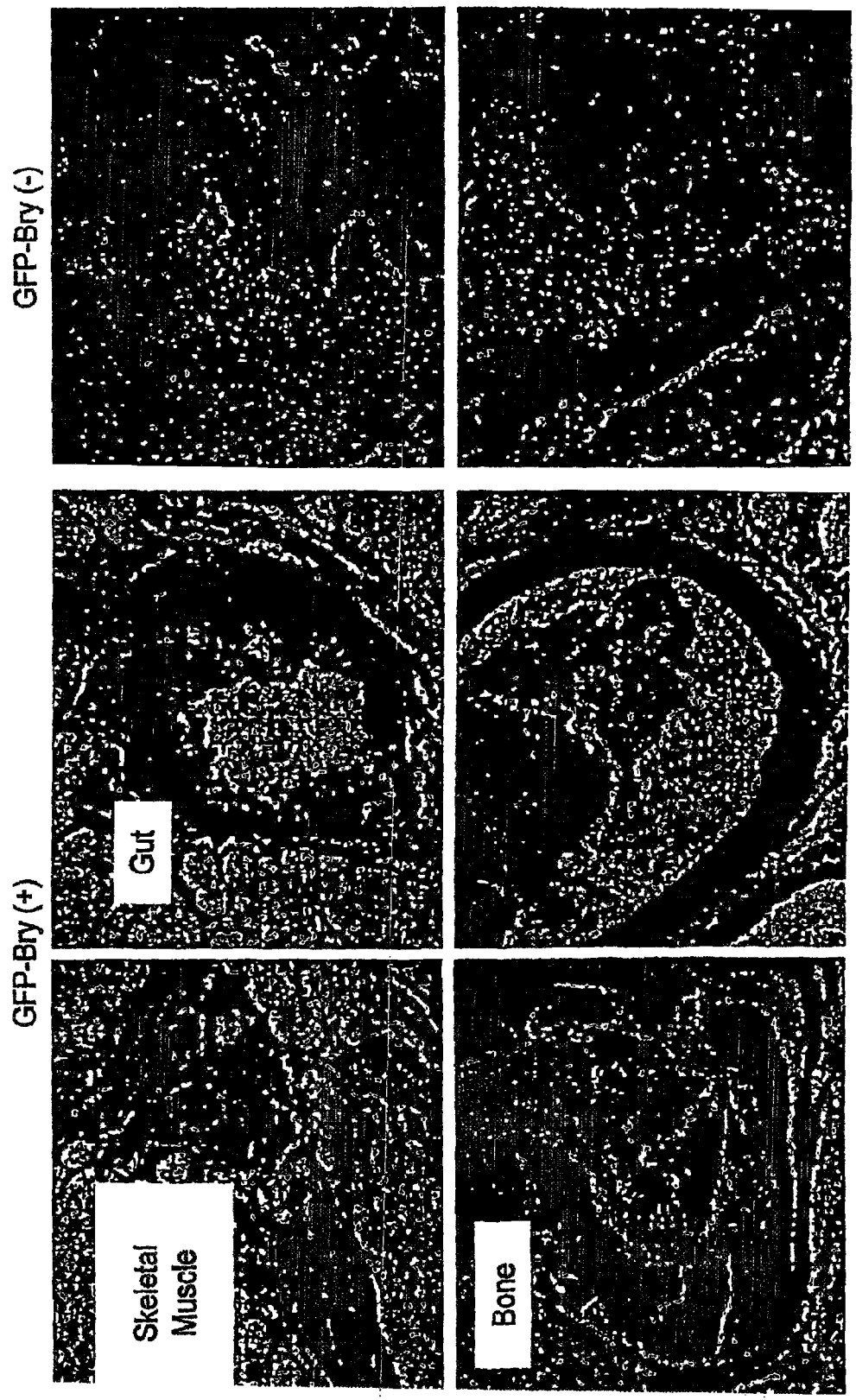
FIG. 26C depicts sections of grafts of the bry+ and bry− populations.

If the teratomas generated by the serum-induced brachyury+ cells resulted from the presence of primordial germ cells, it is possible that the activin induced cells may represent a better source of progenitors for transplantation, as the germ-cell program may not be induced under these conditions. To test this hypothesis, GFP+ and GFP− cells were isolated from EBs induced with 100 ng/ml of activin and cultured for 14 days to promote the differentiation of hepatocyte-like cells. Following this culture period, the cells were harvested and transplanted to the kidney capsule of recipient animals. Three weeks following transplantation, the mice were sacrificed and the kidneys analyzed. Results are shown in FIGS. 26A-C. All mice engrafted with GFP$^-$ cells developed large, multilineage teratomas, consisting of cells from all three germ layers. In contrast, no teratomas were detected in the animals transplanted with GFP$^+$ cells. These cells give rise to differentiated cell masses consisting of endodermal and mesodermal derived tissues including gut epithelium, bone and skeletal muscle. In some instances, skin was also observed in the graft from the GFP$^+$ cells, suggesting that this lineage might also develop from a bry$^+$ cell. These findings indicate that it is possible to generate GFP$^+$ populations that give rise to differentiated tissue without forming teratomas following transplantation.

EXAMPLE 13

Developmental Potential of bry$^+$/c-kit$^-$ and bry$^+$/c-kit$^+$ Cells

Figure 27A:
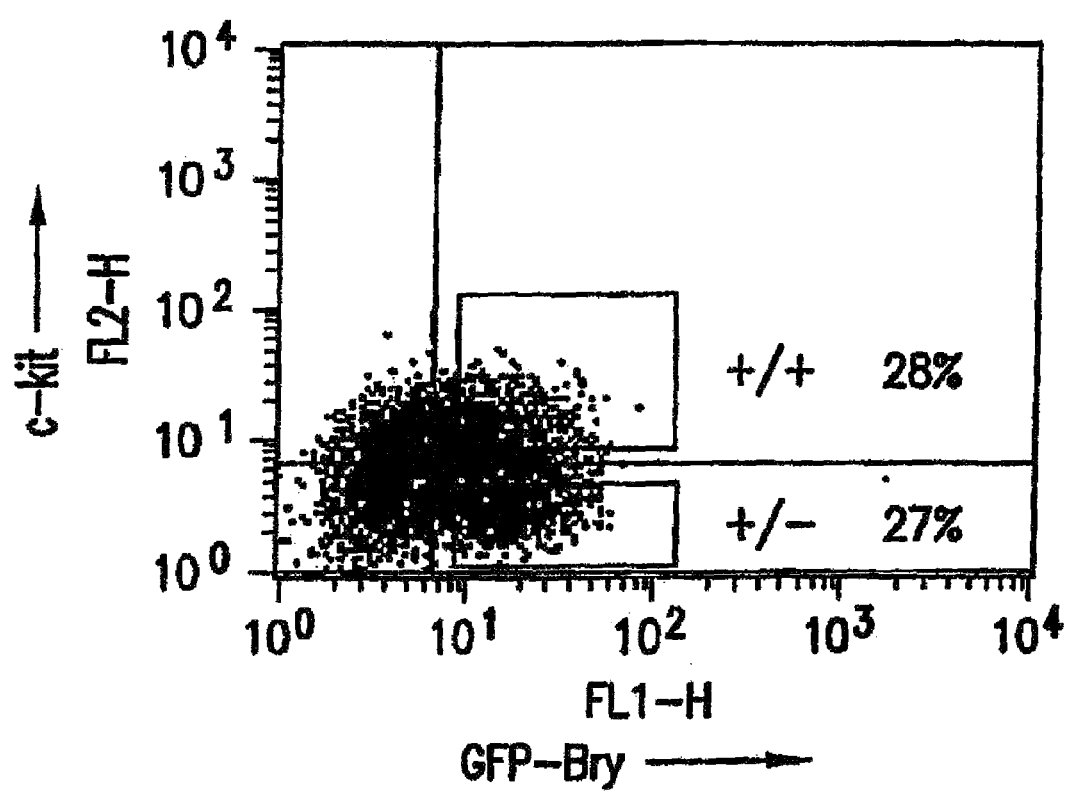
FIG. 27A is a FACS profile indicating the bry+/c-kit+ (+/+) and bry+/c-kit− (+/−) fractions isolated from day three serum-stimulated EBs. Numbers represent the proportion of cells in each of the fractions.
Figure 27B:
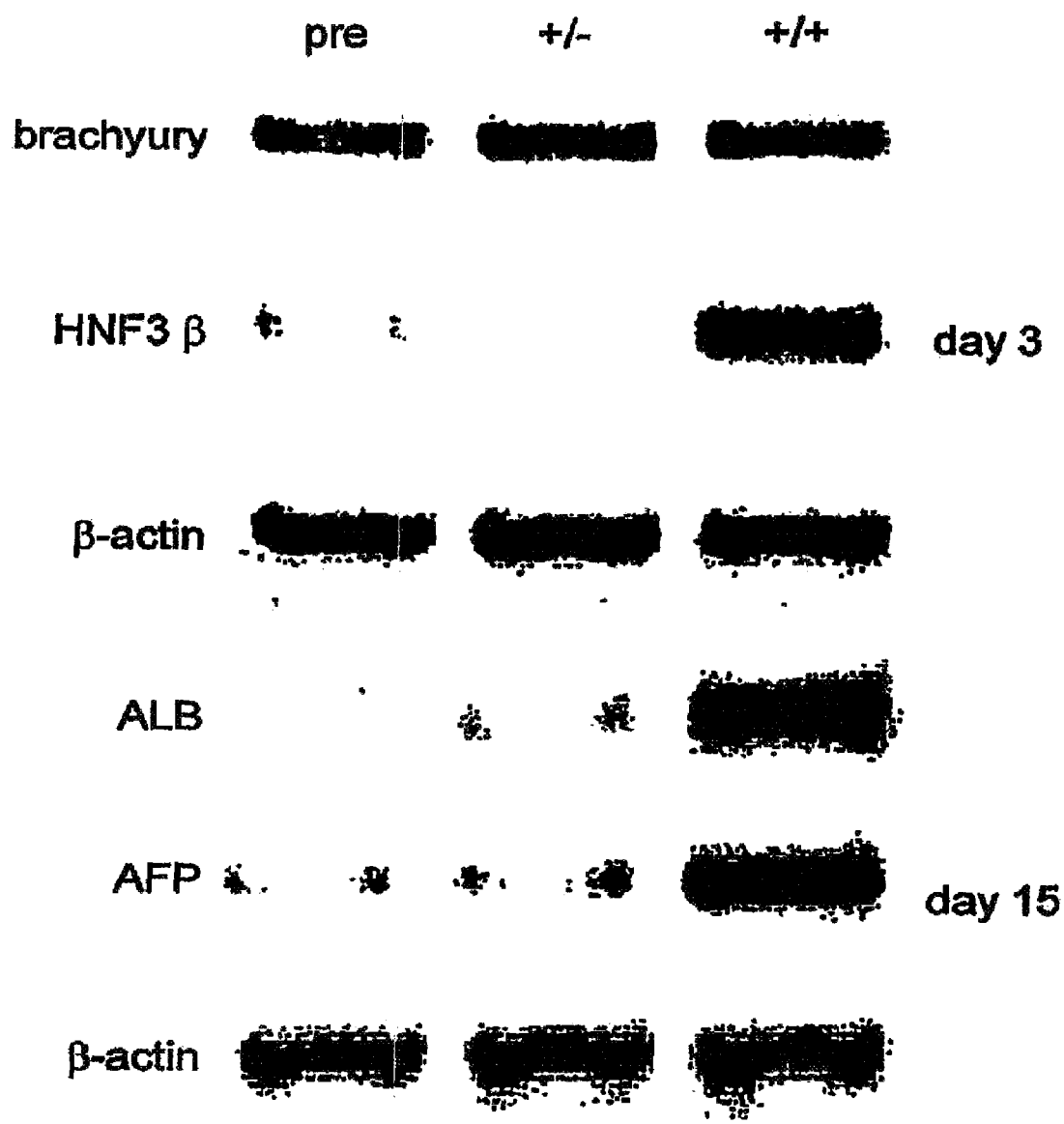
FIG. 27B shows expression analysis of each of the fractions. Day 3 represents cells analyzed immediately following sorting. Day 15 represents cell populations cultured for 15 days in hepatocyte conditions.

The foregoing examples clearly indicate that the hepatocyte lineage develops from a bry$^+$ cell population that has both mesoderm and endoderm potential. Analysis of the bry$^+$ fraction revealed that a subpopulation of these cells expressed the receptor tyrosine kinase c-kit (FIG. 27A) and that this population was distinct from those cells that expressed Flk-1. To determine if c-kit expression could be a useful marker for the segregation of cell with endodermal potential, bry$^+$/c-kit$^-$ (+/−) and bry$^+$/c-kit$^+$ (+/+) cells from day 3 serum-stimulated EBs were assayed for hepatocyte potential. As shown in FIG. 27B, HNF3β, AFP and ALB expressing cells were all derived from bry$^+$/c-kit$^+$ population. To estimate the endodermal potential of this fraction, sorted cells were plated onto glass coverslips and stained with an antibody to HNF3β. Greater than 80% of the bry$^+$/c-kit$^+$ cells expressed HNF3β protein, whereas less than 10% bry$^+$/c-kit$^-$ were positive. These findings indicate that endodermal progenitors express both brachyury and c-kit and that this population is highly enriched for cells with endoderm potential. Isolation of cells based on brachyury and c-kit expression provides a novel strategy for the isolation of endodermal progenitors.

EXAMPLE 14

Developmental Potential of Activin-Induced Cells

Figure 23B:
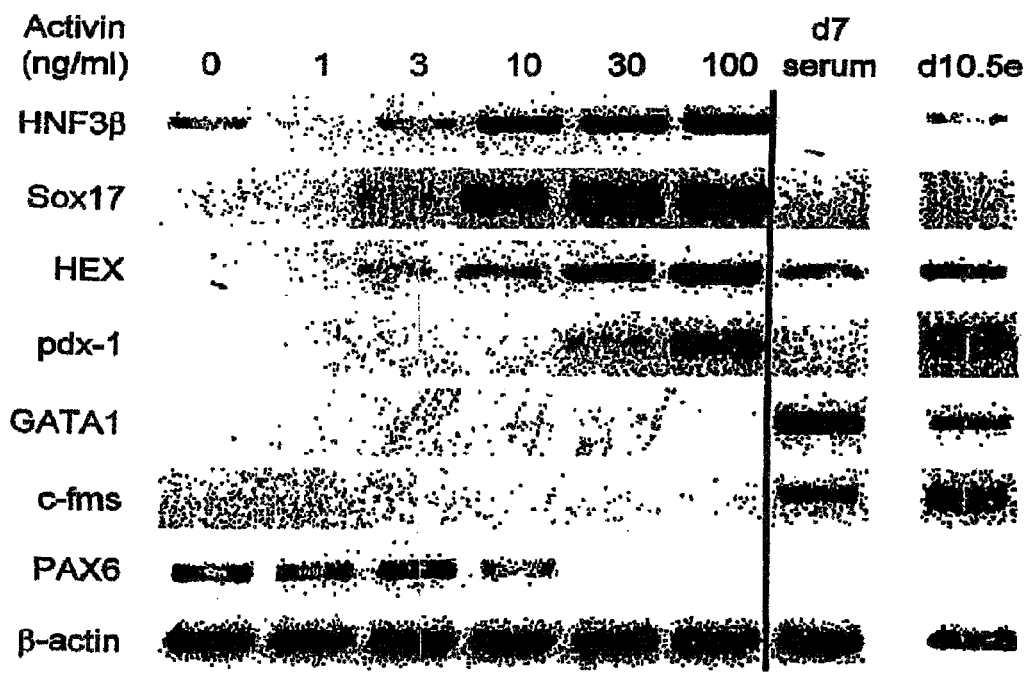

The PCR analysis presented in FIG. 23 indicates that different concentrations of activin induce different developmental programs and that cells with endodermal potential are induced with the highest levels of this factor. To quantify the differential response of activin, cells stimulated with different concentrations of activin were adhered to coverslips and stained with the anti-HNF3β antibody. More than 50% of the entire EB population stimulated with 100 ng/ml of activin expressed HNF3β whereas only 10% of the cells stimulated with 3 ng/ml were positive. Only background levels of staining were observed in the non-stimulated population. These findings demonstrate that high concentrations of activin can stimulate a robust endodermal program, representing a significant portion of entire EB population.

Figure 28:
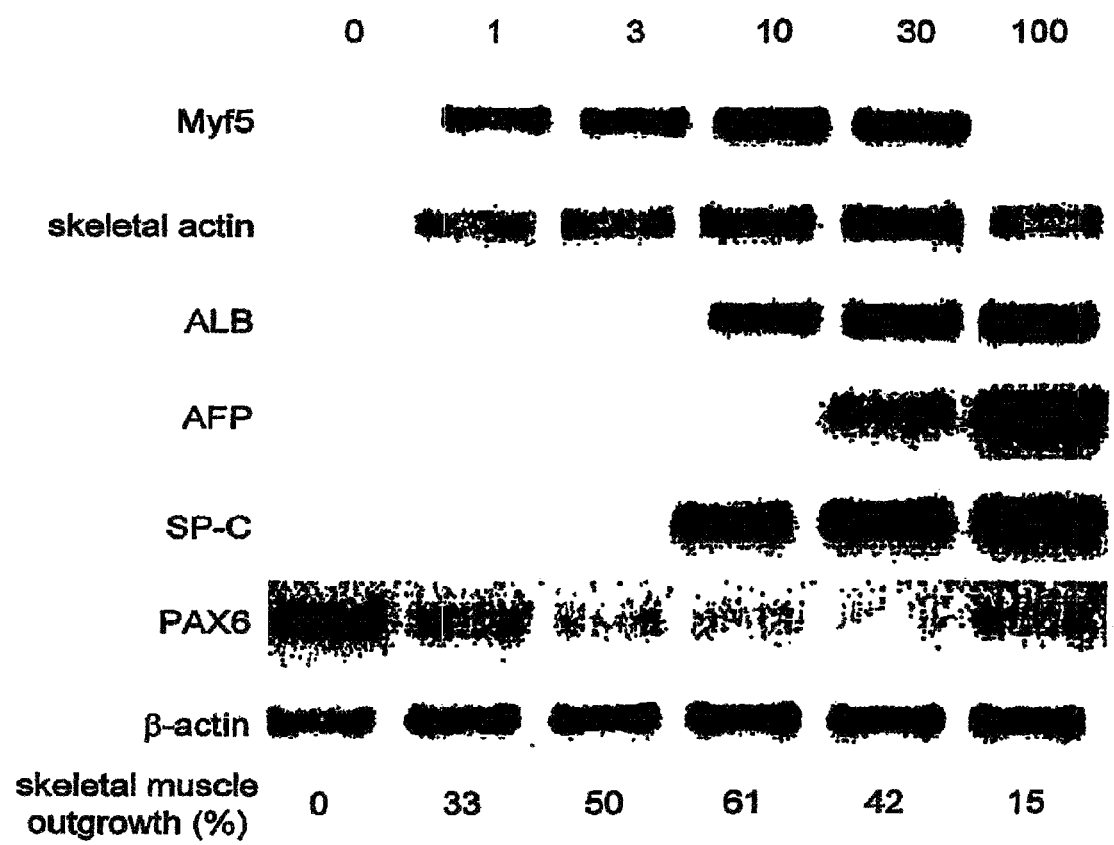
FIG. 28 depicts expression analysis of cell populations derived from EBs induced with different concentrations of activin. Numbers at the top of the figure indicate activin concentration. Numbers at the bottom of the figure represent an estimate of the proportion of EBs with skeletal muscle outgrowths.

As a further assessment of the potential of activin treated cells, day 6 EBs differentiated in the presence of different concentrations of this factor were transferred to serum replacement media for 4 days and then replated in hepatocyte conditions for an additional 4 days. At day 14 of culture, the cells from each group were harvested and subjected to PCR expression analysis. Expression of Myf5 and skeletal actin were monitored to evaluate skeletal muscle development representing an additional mesoderm-derived lineage. Surfactant protein C (SP-C), a lung-specific gene, was included as a marker of endoderm differentiation in addition to AFP and ALB. As shown in FIG. 28, Myf5 and skeletal actin were expressed in cultures stimulated with as little as 1 ng/ml of activin and this expression was detected over a broad range of factor concentrations. Expression of both genes was, however, downregulated at the highest concentration of activin (100 ng/ml). Cultures stimulated with low amounts of activin contained groups of cells with the morphology of skeletal muscle immunostaining demonstrated that these cells expressed both skeletal myosin and α-actinin, indicating that they are of the skeletal muscle lineage. Evaluation of the proportion of replated EBs that generated skeletal muscle outgrowths was consistent with the gene expression analysis, as those stimulated with 3 and 10 ng/ml displayed the most robust skeletal muscle development as depicted in FIG. 28. The expression patterns of the three endodermal genes differed from that observed for the skeletal muscle genes. None were expressed at low activin concentrations and all were readily detected in cultures stimulated with the highest concentrations of the factor. Expression of PAX6 was restricted to untreated cultures and those stimulated with low concentrations of factor. The findings from this analysis confirm and extend those from Example 12 hereinabove in demonstrating that different concentrations of activin induce different developmental programs, with low concentration favoring a mesodermal fate and high concentrations an endoderm fate. In addition, these results indicate that the endodermal cells induced by activin are able to differentiate and give rise to cells with hepatocyte and lung characteristics.

Figure 29:
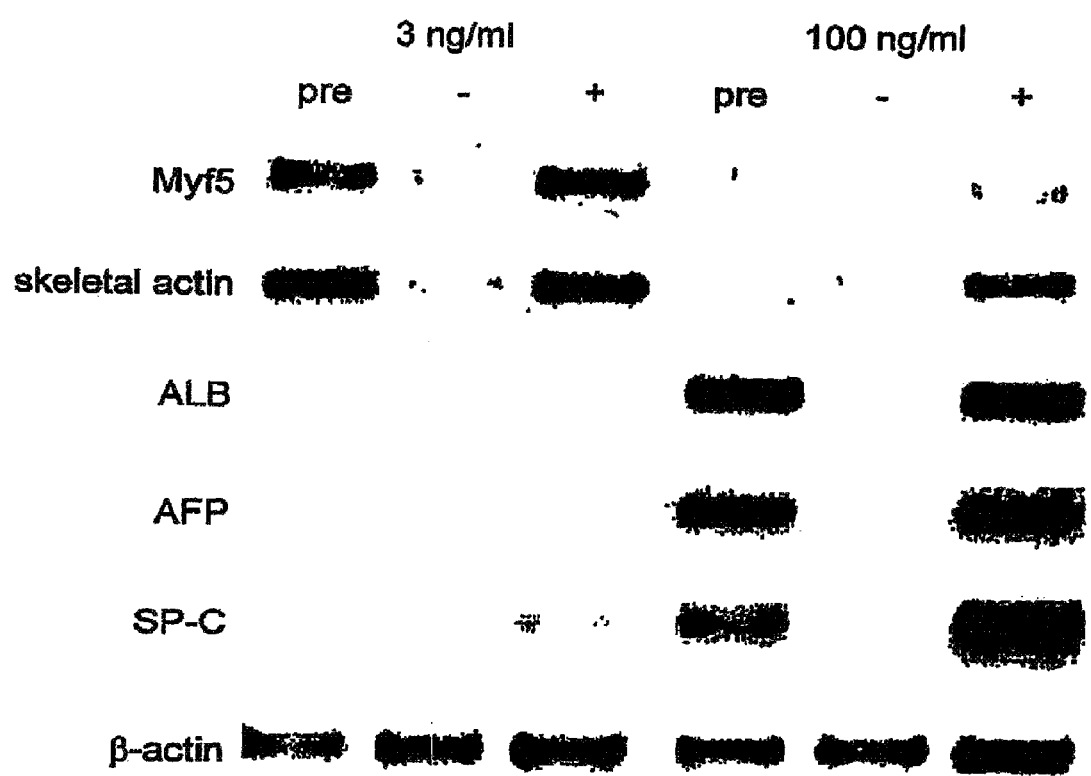
FIG. 29 depicts expression analysis of brachyury fractions isolated from activin-induced populations. Numbers at the top of the figure indicate activin concentration.

Brachyury positive and negative populations isolated from EBs stimulated with low and high concentrations of factor were also analyzed for expression of the skeletal muscle and endoderm genes. As shown in FIG. 29, both myf5 and skeletal actin expression were restricted to the population generated from the bry$^+$ population isolated from EBs stimulated with 3 ng/ml of activin. Similarly, the endoderm genes were expressed in the brachyury$^+$-derived cells isolated from EBs generated in the presence of 100 ng/ml of factor. These findings further demonstrate that both mesoderm and endoderm develop from brachyury$^+$ cells.

EXAMPLE 15

Generation of HNF-CD4 Targeted ES Cells

In order to track and isolate endodermal as well as mesodermal populations during EB differentiation, ES cells which already have GFP targeted to the brachyury locus were targeted with human CD4 (hCD4) protein into the HNF3β locus. HNF3β is known to be expressed in most endodermal cell types, starting very early during embryonic development. Kaestner et al. (1994) Genomics 20:177-85. The targeting construct contains the human CD4 cDNA, truncated at amino acid number 424, and lacks most of the intracellular domain This cell surface molecule was chosen because it cannot transduce signals and there are readily available antibodies for flow cytometry, which recognize hCD4 and will not cross react with endogenous mouse CD4.

Figure 30A:
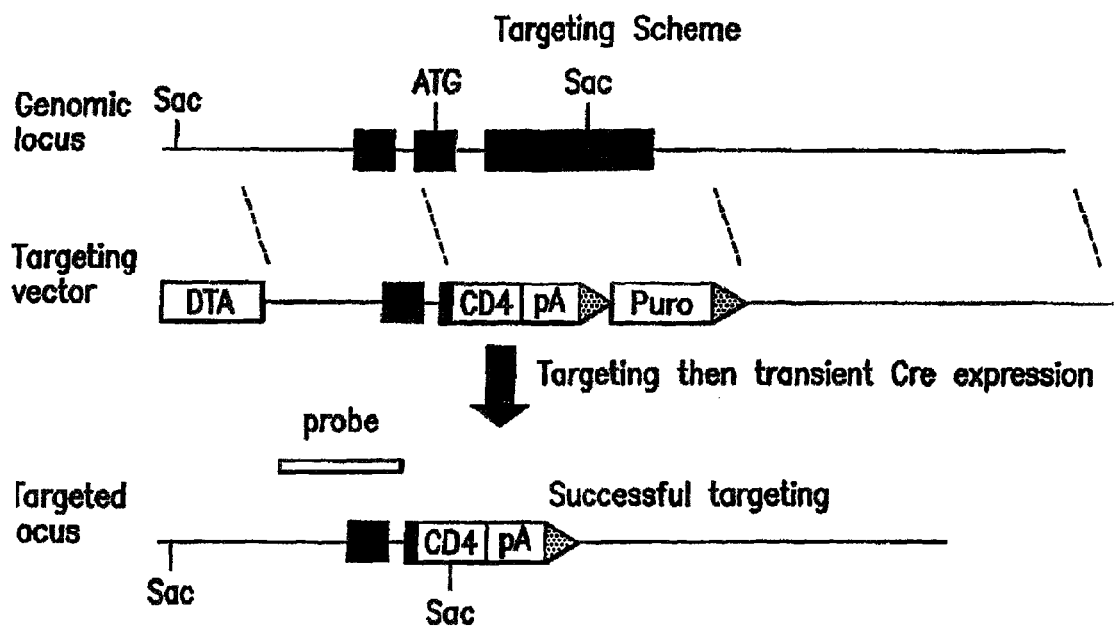
FIGS. 30A and 30B depict the method used to target human CD4 (hCD4) into the HNF3β locus.

The vector also contains two regions of homology to the mouse HNF3β locus, the bovine growth hormone poly(A) sequence, and a loxp flanked puromycin cassette as depicted in FIG. 30A. The diptheria toxin A (DTA) gene was included in the 5' end of the targeting vector to select against random integration. The targeting vector was constructed as follows.

The short arm and long arm of homology were obtained from a published HNF3B targeting vector. Weinstein et al. (1994) Cell 78: 575-588. The same long arm was used while a 1.8 kb fragment of the short arm was used to create the hCD4 knock in vector. The short arm contains part of the HNF3B promoter, exon 1, intron 1, and part of exon 2, ending just before the endogenous ATG initiation site. The long arm consists of a 7 kb sequence starting 3 kb downstream of the end of the last exon. Using standard molecular biology techniques, hCD4 with a kozak sequence followed by the bovine growth hormone poly(A) sequence along with a puromycin cassette was cloned in between the two arms of homology as shown in FIG. 30A.

Figure 30B:
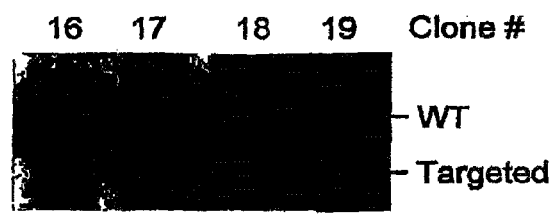

The GFP-Bry ES cells described in example 2 were electroporated with the HNF3β targeting vector. The cells were then selected with puromycin and clones were picked and expanded. Genomic DNA was isolated, cut with the restriction enzyme Sac I, and a Southern blot analysis was performed with a probe upstream of the endogenous ATG as indicated in FIG. 30B. The wild type allele gives a 3.3 kb band while the targeted allele gives a 2.8 kb sized band. Of 48 clones screened, 2 targeted clones were generated, corresponding to a 4.2% targeting efficiency. Both targeted clones were transiently transfected with a modified Cre recombinase expression vector to remove the puro gene. The targeted clones are referred to hereinafter as CD4-HNF/GFP-T ES cells.

HNF3B is expressed transiently in EBs during serum induced differentiation. To determine whether hCD4 expression in CD4-HNF/GFP-T ES cells accurately reflects expression of the HNF3β gene during EB development, CD4 versus GFP expression was assessed.

Figure 31A:
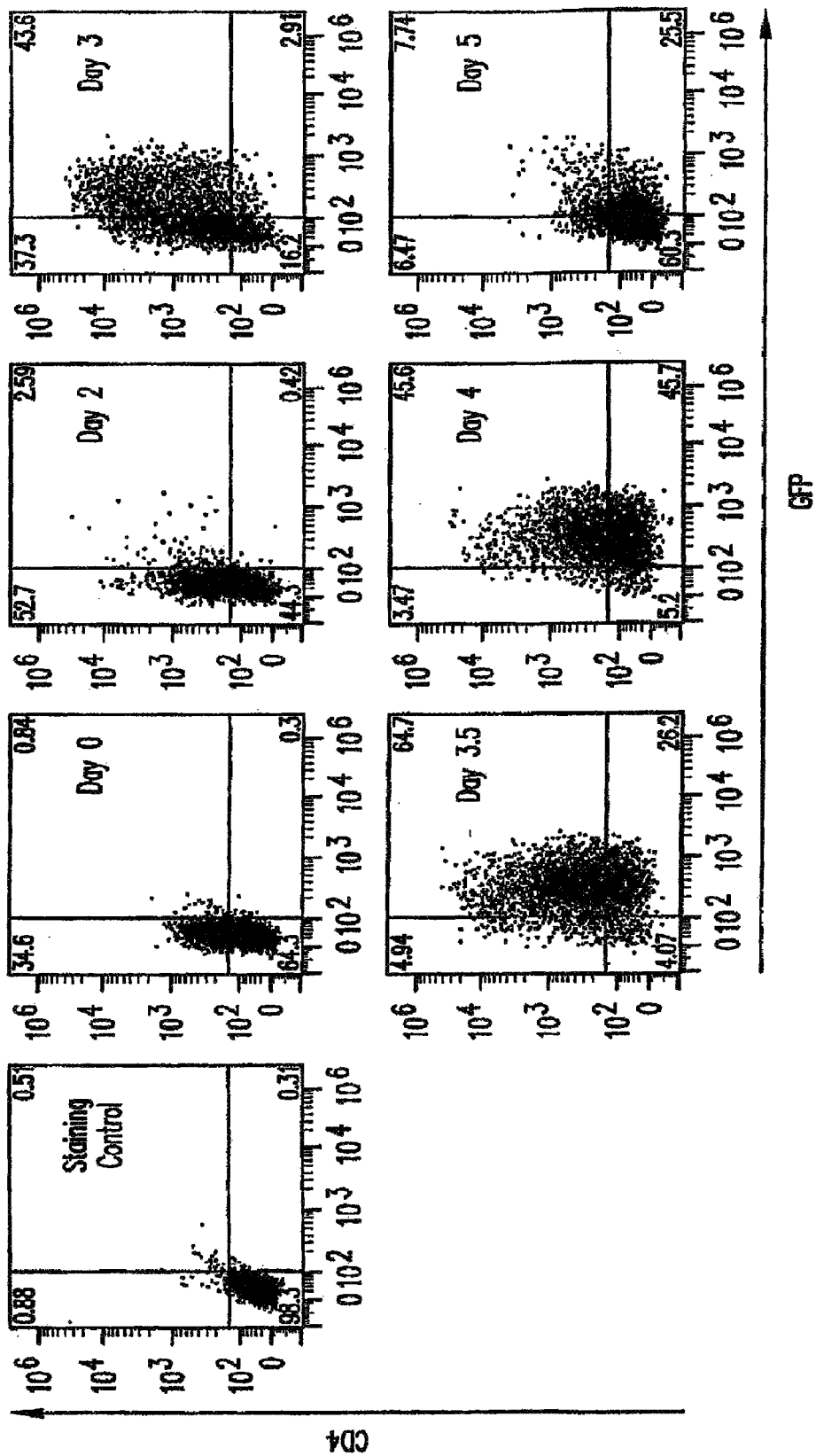
FIGS. 31A, 31B and 31C depict the expression of GFP, hCD4, Brachyury, and HNF3β in developing EBs induced with serum.
Figure 31B:
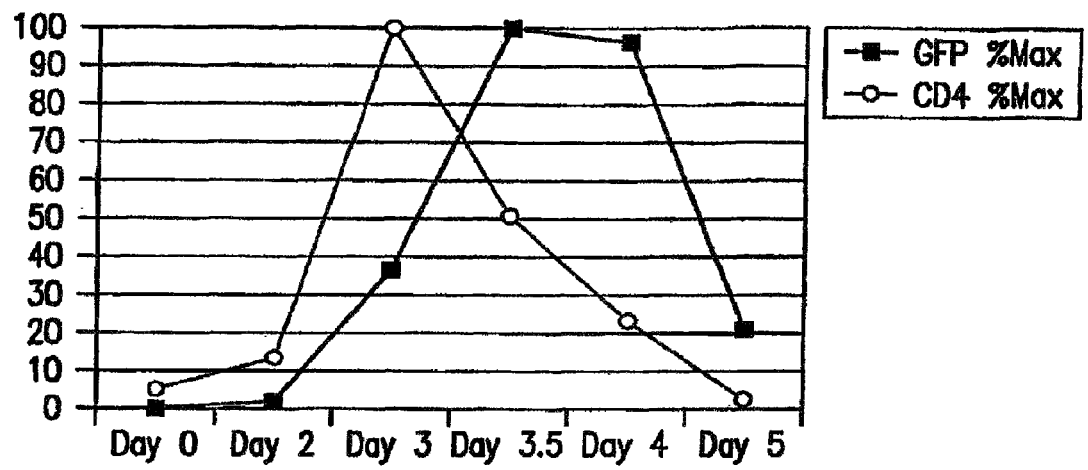
Figure 31C:
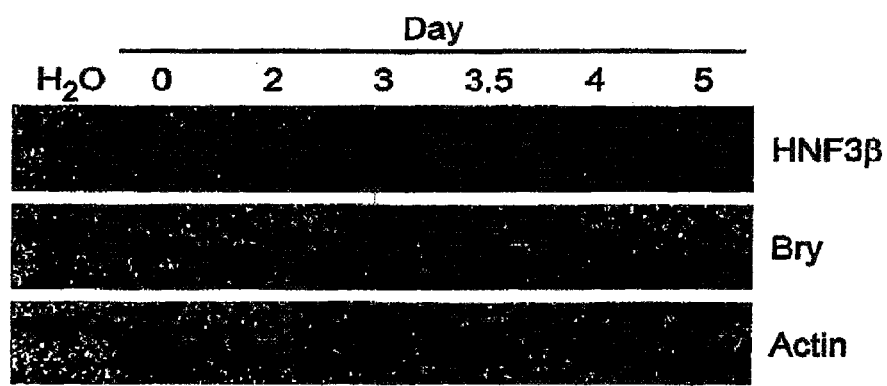

A typical expression pattern of GFP versus hCD4 during a 5 day serum induced EB differentiation is shown in FIG. 31A. ES cells are low to negative for hCD4 expression. Following differentiation, hCD4 expression is sharply upregulated specifically in the GFP$^+$ cells at day 3. Expression falls rapidly by day 3.5 and is almost undetectable by day 5. In contrast, GFP expression persists to day 4 and decreases by day 5. The mean fluorescence intensity for GFP and hCD4 expression is shown in FIG. 31B. It is seen that hCD4 peaks at day 3 and is lost quickly while GFP peaks at days 3.5 to 4. Semi-quantitative RT PCR for HNF3B and Brachyury expression was also performed on the samples (FIG. 31C). The PCR for the endogenous genes follows what is seen using flow cytometry for GFP and hCD4. HNF3B and Brachyury are both expressed by day 3, while HNF3B expression decreases by day 3.5 and is undetectable by day 5. Brachyury expression continues at high levels up to day 4. These data confirm that hCD4 is mirroring the expression of endogenous HNF3B. In addition, hCD4 expression is seen to decline along with HNF3B RNA levels, suggesting that the half live of the hCD4 protein is not excessively long and can be used to accurately select cells expressing HNF3B. It is also seen that all GFP$^+$ cells are initially hCD4$^+$, but then rapidly lose expression of hCD4. This data is suggestive of a mesendoderm precursor to both endoderm and mesoderm, supporting the data in example 9. This population has been demonstrated in lower organisms such as *c. elegans* but has not been established in mammals. The conditions used above have been selected for robust mesoderm induction. It is possible that mesendoderm is formed but is rapidly converted into mesoderm.

EXAMPLE 16

EB Differentiation as a Model for Primitive Streak Formation

During embryogenesis, both the mesoderm and endoderm lineages are derived from a structure called the primitive streak. Beddington and Robertson (1999) Cell 96: 195-209. The primitive streak is characterized by expression of specific genes such as Brachyury, which is expressed along the whole streak. HNF3B is also expressed in the streak, though it has only been detected in the anterior section. HNF3B expression as demonstrated by hCD4 was seen to be heterogeneous in the Bry-GFP$^+$ population. It is possible that serum induction allows development of a group of primitive streak like cells, with the GFP$^+$ HNF3B$^{lo}$ cells representing the posterior streak while the GFP$^+$HNF3B$^{hi}$ cells correspond to the anterior streak.

Figure 32A:
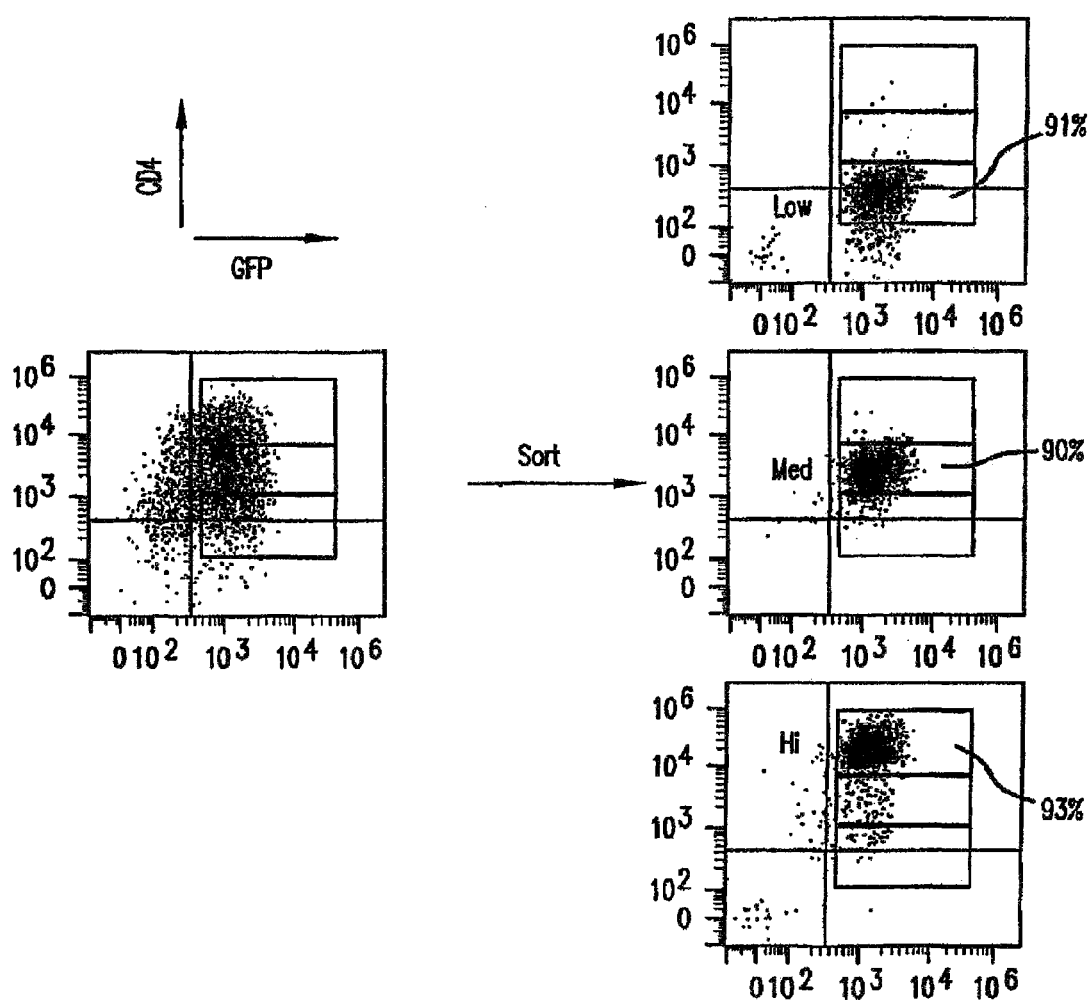
FIGS. 32A, 32B and 32C depict gene expression in different GFP hCD4 expressing population as well as tissue dissected from the primitive streak of mouse embryos. EBs were differentiated in serum for 3.25 days and sorted by the expression of GFP and hCD4.
Figure 32B:
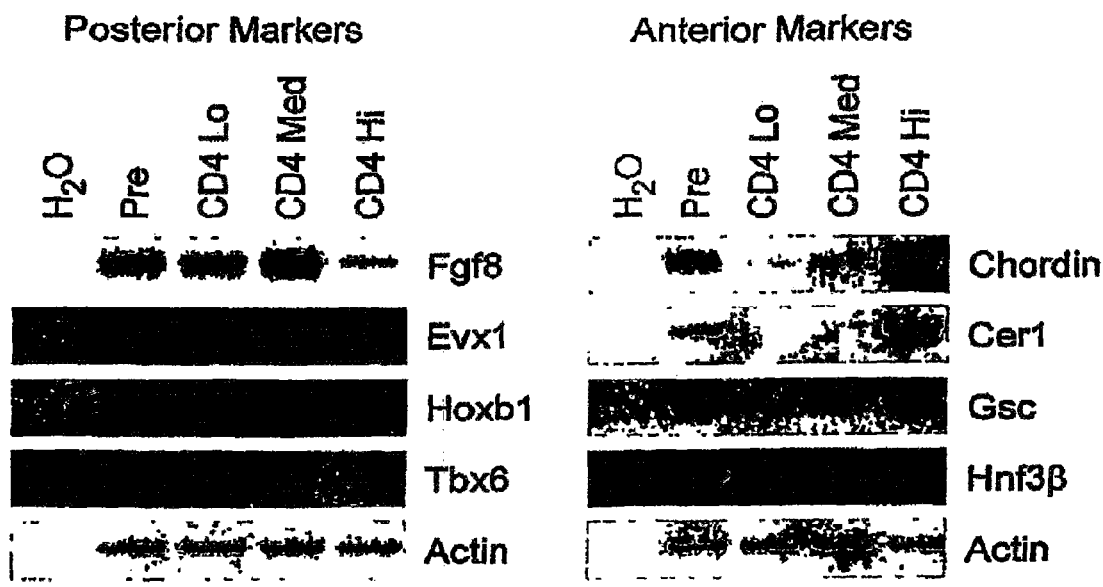
Figure 32C:
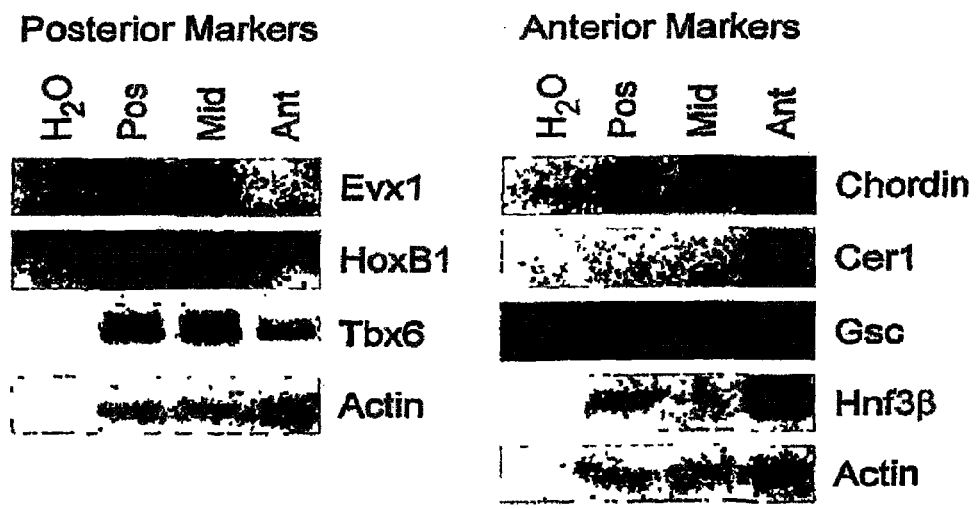

To determine if GFP and hCD4 expression could be used to separate posterior and anterior primitive streak like cells from CD4-HNF/GFP-T ES cells, EBs differentiated for 3.25 days were sorted into three populations: GFP$^+$ hCD4$^{lo}$, GFP$^+$ hCD4$^{med}$, and GFP$^+$hCD4$^{hi}$ (FIG. 32A). There are many genes that are recognized to be expressed asymmetrically in the primitive streak. RT PCR was performed on the sorted populations for genes known to be expressed in either the posterior or anterior primitive streak (FIG. 32B). The posterior primitive streak specific genes Fgf8, Evxl, HoxBl, and Tbx6 were all expressed at higher levels in hCD4$^{lo}$ and hCD4$^{med}$ populations compared to hCD4$^{hi}$ cells. In contrast, the anterior primitive streak genes Chordin, Cerl, and Gsc are all expressed at high levels in hCD4$^{hi}$ cells, low to negative in hCD4$^{med}$ cells, and not at all in hCD4$^{10}$ cells. HNF3B expression was also examined to verify that the hCD4 sorting isolated cells expressing different levels of the HNF3B gene. The highest levels of HNF3B were seen in the hCD4$^{hi}$ population with decreasing amounts in the hCD4$^{med}$ and hCD4$^{lo}$ populations as expected. To confirm that the expression patterns in the various hCD4 populations is an accurate representation of gene expression in the primitive streak, the primitive streaks of day 7.25 mouse embryos were dissected and analyzed for gene expression. Mice embryos were used that were derived from the GFP-Bry ES cells. The anterior, middle, and posterior primitive streak tissues were then dissected under a fluorescent dissection scope to ensure that the tissues obtained were from the GFP$^+$ (primitive streak) portions of the embryo. FIG. 32C shows the results of RT PCRs performed from the dissected streak tissues. These data indicate that the sorted hCD4 populations show similar relative gene expression profiles for the anterior and posterior genes examined These data indicate that the expression of hCD4 and GFP in CD4-HNF/GFP-T ES cells can be used to isolate cells with gene expression patterns indicative of the anterior and posterior primitive streak.

EXAMPLE 17

Function Potentials of Different Populations of hCD4 Expressing Cells

Figure 33A:
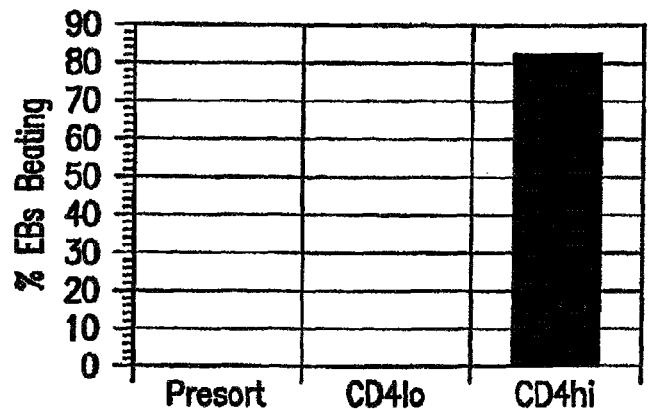
FIGS. 33A, 33B and 33C depict the developmental potential of different GFP hCD4 expressing populations. EBs were differentiated and cell sorted as in FIG. 32. Only two populations were sorted, GFP+ hCD4$^{lo}$ and GFP+ hCD4$^{hi}$ cells. After sorting, cells were reaggregated in serum replacement containing medium for 2 days.
Figure 33B:
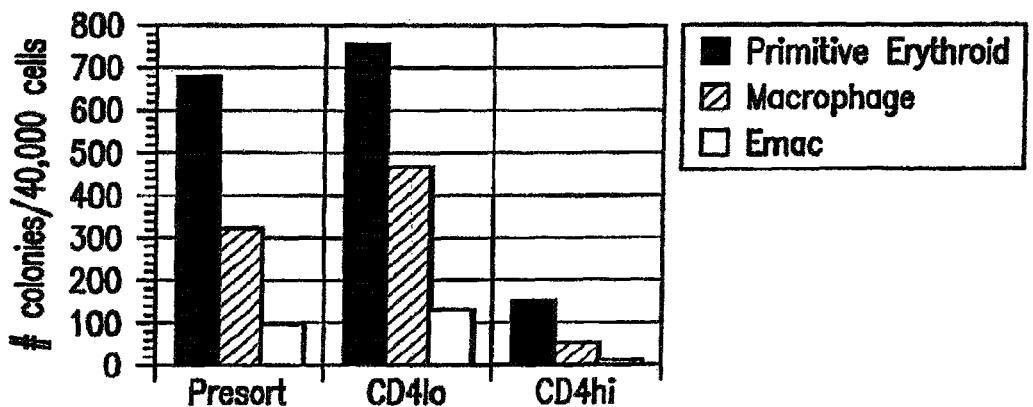
Figure 33C:
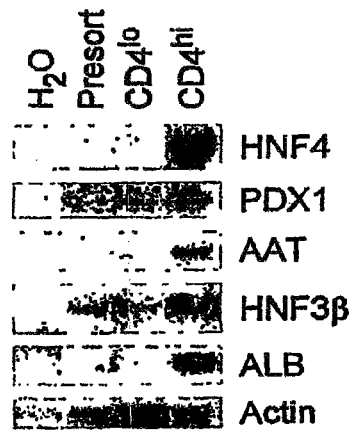

Lineage tracing experiments have demonstrated that the anterior and posterior primitive streak develop into distinct lineages. The posterior streak gives rise to the yolk sac and hematopoietic cells while the anterior streak forms endoderm and anterior mesoderm such as cardiac tissue. Robb and Tarn (2004) Sem. Cell & Dev. Biol. 15: 543-554. To determine if the primitive streak like cells from EBs behave functionally like the endogenous primitive streak, CD4-HNF/GFP-T ES cells were differentiated for 3.25 days, sorted for GFP+ hCD4$^{lo}$ and GFP+ hCD4$^{hi}$ populations and assayed for hematopoietic, cardiac, and endoderm potential. For all assays, the sorted populations were allowed to reaggregate for 48 hours in serum free conditions. FIG. 33 A shows cardiac potential of sorted cells which were plated onto matrigel after reaggregation. Individual EBs were scored for the presence of beating cells 24-48 hours after adhering. Beating EBs were only seen from the hCD4$^{hi}$ population at this time point. FIG. 33B demonstrates hematopoietic potential of the sorted populations. Cells were trypsinized after reaggregation and plated in methylcellulose with hematopoietic growth factors. The presences of hematopoietic colonies were counted 5-7 days later. The majority of all hematopoietic colonies were found in the hCD4$^{lo}$ population. FIG. 33C shows RT PCR for endoderm specific genes of the sorted populations which were plated onto matrigel in serum free conditions after reaggregation. Only the hCD4$^{hi}$ cells expressed the endodermal genes HNF4, Pdx1, AAT, ALB, and HNF3B after 5 days on matrigel. These data demonstrate that the expression of hCD4 and GFP can be used to segregate populations with different developmental potentials. These potentials are consistent with hCD4$^{lo}$ and hCD4$^{hi}$, cells being similar to the posterior and anterior primitive streak respectively.

EXAMPLE 18

Figure 34A:
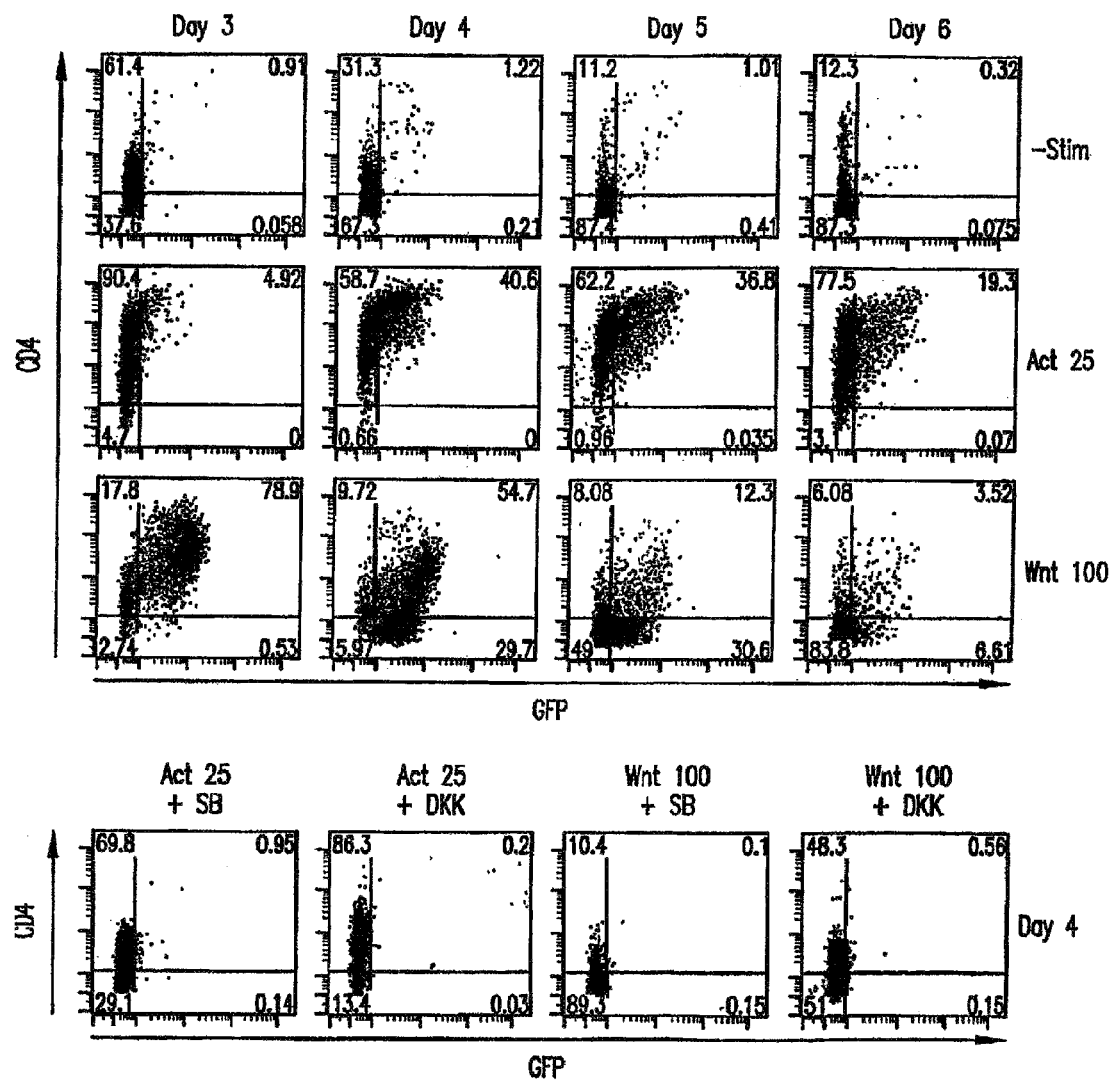
FIGS. 34A, 34B and 34C depict ES cells differentiated in serum free conditions with Activin A Wnt3a and/or inhibitors of these pathways. ES cells were cultured in serum free media for two days then trypsinized to obtain a single cell population. These cells were then reaggregated with the indicated conditions. At day six, the EBs were plated on matrigel coated dishes in serum free media.
Figure 34B:
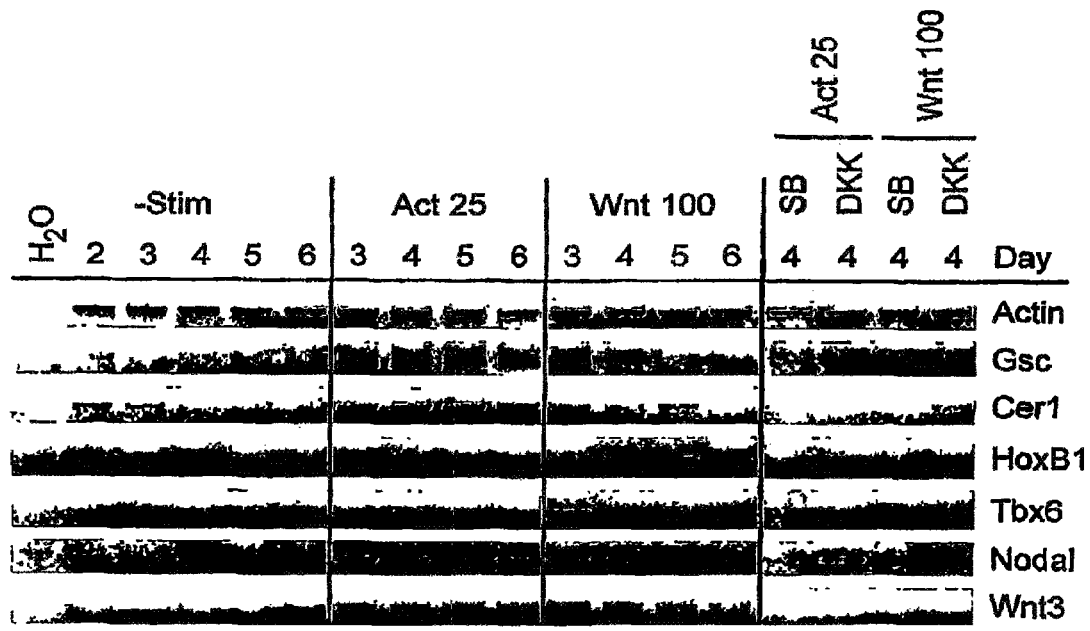
Figure 34C:
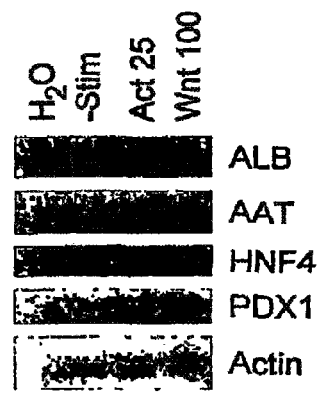

Activin Signaling and Wnt Signaling are both Required for ES Derived Primitive Streak Like Cells Studies in mice have demonstrated the importance of Wnt signaling as well as nodal/activin signaling in gastrulation and endoderm/mesoderm induction. Liu et. al. (1999) Nat. Genet. 22: 361-4. Example 12 hereinabove demonstrates that activin can induce both mesodermal and endodermal populations from ES cells in serum free cultures. To determine the effects of activin and Wnt signaling on the differentiation of ES derived primitive streak like cells, CD4-HNF/GFP-T cells were differentiated in serum free culture with either recombinant Wnt3a or activin A. Both activin and Wnt can initially induce GFP+ CD4+ cells, though Wnt displays a faster kinetics (FIG. 34A). Activin stimulation leads to high levels of CD4 expression that persist after loss of GFP-Bry expression at day 6. In contrast, GFP+ cells induced with Wnt have lower levels of CD4 and rapidly lose expression by day 5. activin also induces robust expression of other anterior primitive streak markers such as Gsc and Cerl while Wnt does not (FIG. 34B). Wnt does however stimulate expression of the posterior primitive streak markers HoxBl and Tbx6, while activin only induces Tbx6. These data suggest that activin induces ES anterior primitive streak cells while Wnt induces ES posterior primitive streak cells. At day 6, EBs that were stimulated with either activin or Wnt3a were plated on matrigel in serum free media to allow further development. After a further 6 days, these cultures were harvested and endodermal gene expression was determined by RT-PCR (FIG. 34C). activin induction allowed development of cells expressing the endodermal genes Alb, Aat, HNF4, and Pdx1, confirming findings in example 12. However, the Wnt3a induced cultures did not express any of these markers suggesting that activin signaling is required for endoderm development.

Considering that Wnt stimulation induces nodal and activin treatment induces Wnt3 (FIG. 34B), it is unknown whether activin/nodal signaling or Wnt Signaling alone can induce primitive streak formation or whether both factors are required together. CD4-HNF/GFP-T ES cells were induced with either activin or Wnt in conjunction with specific inhibitors of these pathways. DKK1 was used to inhibit Wnt signaling while the small molecule inhibitor SB-431542 (SB) was used to block Nodal/TGFβ signaling. DKK1 functions by binding the Wnt co-receptors, LRP5 and LRP6, which are essential for activation of the βcatenin signaling pathway. SB is a specific inhibitor of the receptors ALK4, 5, and 7 and thus is able to block TGFβ, activin, and Nodal signaling. It does not, however, block BMP signaling. Inman et. al. (2002) Mol. Pharmacol. 62: 65-74. Both inhibitors completely blocked the development OfGFP+ CD4+ cells with either inducer (FIG. 34A). The primitive streak markers Gsc, Cerl, HoxBl, and Tbx6 were also absent or greatly reduced (FIG. 34B). This indicates that Wnt and activin/nodal signaling are required together to induce ES derived primitive streak like cells. Therefore, to induce mesoderm and endoderm germ layers and their derivative tissues, both activin/Nodal and Wnt signals are required initially.

EXAMPLE 19

Activin Signaling and Wnt Inhibition can Induce Endoderm Differentiation

Figure 35A:
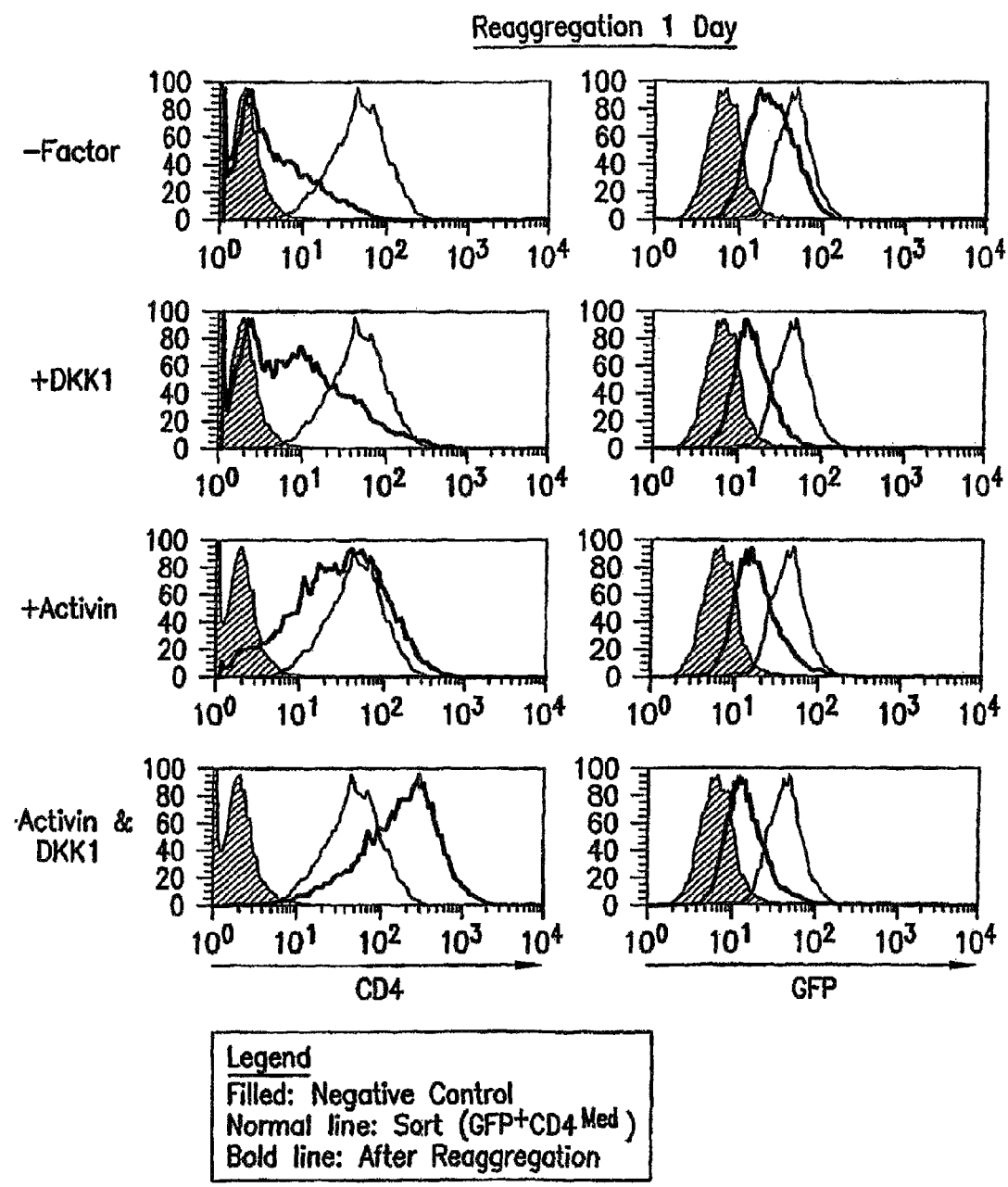
FIGS. 35A and 35B depict, the effects of DKK1 and activin on EB differentiation. EBs differentiated and sorted as in FIG. 32 for GFP+ hCD4$^{med}$ were allowed to reaggregate in serum replacement containing media alone or with the addition of human DKK1 100 ng/ml, activin 100 ng/ml, or both factors together.
Figure 35B:
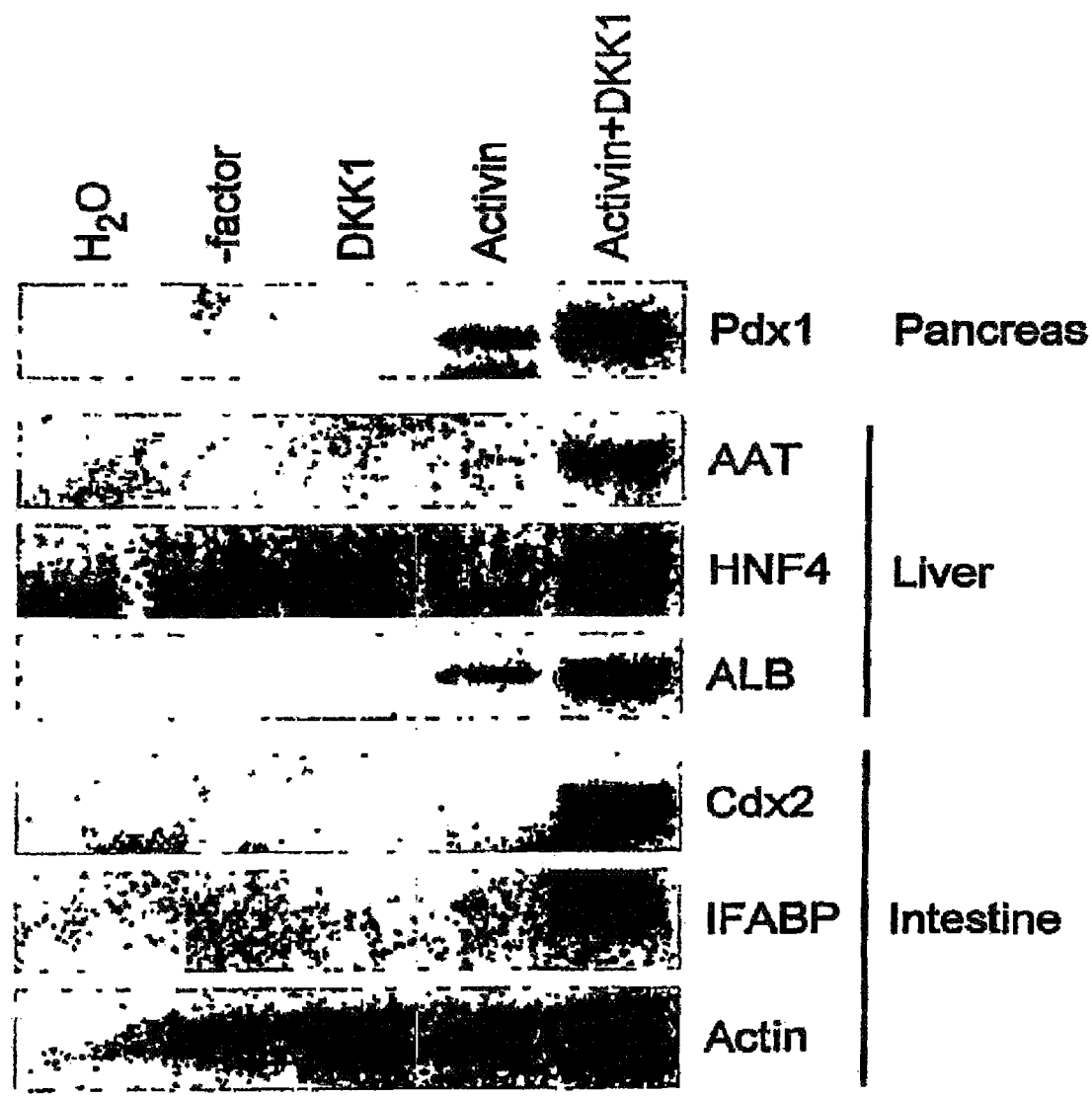

Example 12 demonstrated that high levels of activin could induce endodermal gene expression from EBs differentiated in completely serum free conditions. Nodal, a key molecule involved in mesoderm/endoderm induction in vivo, signals through the same receptors as activin. It is also known that Nodal as well as inhibitors for Wnt signaling are expressed preferentially in or around the anterior primitive streak. Considering that the endoderm forms from the anterior primitive streak, it is possible that nodal/activin signaling in combination with inhibition of Wnt signals induces endoderm formation. To test this hypothesis, CD4-HNF/GFP-T ES cells were differentiated for 3.25 days in serum and GFP+ hCD4$^{med}$ cells were sorted and reaggregated in serum free media with no factor, DKK1 (Wnt inhibitor), activin, or activin and DKK1. The effect of these culture conditions on hCD4-HNF3β and GFP-Bry levels were analyzed by flow cytometry (FIG. 35A). With serum free media alone, hCD4 expression was lost after 1 day reaggregation Inhibition of Wnt signaling by the addition of DKK1 allowed some cells to retain low levels of hCD4. Addition of activin allowed the retention of HNF3β levels similar to newly sorted cells. Lastly, activin and DKK1 worked synergistically to increase hCD4 levels almost one log over the levels after sorting. GFP levels were lost for all of the conditions tested, suggesting that differentiation was proceeding in all cultures but that the cultures expressing more hCD4 were differentiating into endodermal lineages. To further test this idea, sorted cells reaggregated for two days in the culture conditions above were washed with serum free media without factors and plated onto martrigel in serum free media. After 5 days, the cultures were harvested and gene expression determined by RT PCR. FIG. 35B shows the expression of several endoderm genes specific for the pancreas, liver, and intestine. None of these genes were detected in either media alone or DKK1 treated cultures. Very low levels of just two of the genes, Pdx1 and ALB were detected in the cultures treated with activin alone. Treatment with both activin and DKK1 led to high expression of Pdx1, AAT, HNF4, ALB, Cdx2, and IFABP. These data demonstrate that the combination of signaling through the activin receptor and inhibition of Wnt signals by DKK1 treatment induces endoderm formation from a cell population that would not form endoderm when cultured in media alone. These culture conditions have the potential to allow the large scale production of endodermal derived tissues such as the pancreas and liver. These experiments also demonstrate the utility of the CD4-HNF/GFP-T ES cells as a tool to assess endoderm development in a quantitative manner

EXAMPLE 20

Generation of Hepatocytes from Endoderm-Derived Mouse Embryonic Stem Cells

By using the GFP-Bry, hCD4-Foxa2 ES cell line described in Example 15 hereinabove, endoderm cells were tracked by flow cytometry by their GFP and hCD4 expressions upon ES cell differentiation. (The terms HNF3β and Foxa2 are used interchangeably.

GFP-Bry, hCD4-Foxa2 ES cells were maintained in absence of serum and feeder cells in a media consisting of Neurobasal, DMEM/F12, N2 supplement, B27 with retinoic acid, 10% BSA, MTG ($1.5 \times 10^{-4}$M), Glutamin, LIF (1000 U/ml) and BMP-4 (10 ng/ml). In these conditions, cells form tight colonies that remain undifferentiated. In order to induce the endoderm program, ES cells were harvested and cultured in presence of activin-A (50 ng/ml) in a serum-free media (IMDM, F12 media, B27 with retinoic acid, N2 supplement, BSA, MTG, glutamin, ascorbic acid) at low density (35,000 cells/5 ml) in a ultra low attachment dishes to allow embryoid bodies (EB) formation. As the ES cells differentiate, expression patterns for GFP-Bry, hCD4-Foxa2 and the receptor for stem cell ligand c-Kit have been defined. A large cell population GFP-Bry$^+$, hCD4-Foxa2$^{high}$ and cKit$^{high}$ (named +++) emerged at day 4, and was assayed for its endoderm potential and hence hepatic fate versus their counterpart population GFP-Bry+, HCD4$^{low}$ and c-Kit$^-$ (named +L−). To address these issues, both populations were reaggregated for 2 days in presence of the two cytokines known to specify endoderm cells into liver in the embryo, BMP-4 (30 ng/ml) and bFGF (10 ng/ml) in the serum free media indicated above. Zaret (2001) Curr Opin Genet Dev 11:568-574. In addition to the two cytokines, activin-A (50 ng/ml) has been added to maintain an endoderm potential of the cells as opposed to a mesoderm fate. To allow maturation of the hepatocyte progenitors (hepatoblasts), aggregates were then plated on gelatin-coated dishes in a media that is appropriate for hepatoblast/hepatocyte maturation and growth. This media consists of the basic differentiation media indicated above supplemented with VEGF (10 ng/ml), dexamethasone and other cytokines present in the Block media known to promote hepatoblast/hepatocyte growth Those include human recombinant HGF (20 ng/ml), EGF (10 ng/ml), bFGF (10 ng/ml) and TGFalpha (20 ng/ml). Block et al., (1996) J Cell Biol 132:1133-1149. Six days later, +++ aggregates gave rise to numerous "hepatic colonies" attached to the dish as well as a large number of floating aggregates that did not attach. All +L− aggregates attached to the dish and formed very few "hepatic colonies", but no floating aggregates were seen in the culture. These results suggest that the day 4 +++ population is highly enriched in endoderm cells and demonstrate that the combination of BMP-4, bFGF and activin-A promote strongly the specification of the day 4 +++ cells into hepatocytic lineage.

One day following plating on gelatin-coated dishes, ⅔ of the +++ aggregates remained floating in culture, while the other ⅓ attached and formed hepatic colonies that were sometimes surrounded by other cells. At this early time point, many cells within the colonies expressed albumin and AFP assayed by immunohistochemistry. The surrounded cells were all CD31 positive cells suggesting that they are endothelial cells.

Later on at day 12, hepatic colonies grew larger. At this later time point, most of the cells within the colonies are AFP and albumin positive, and most of the cells surrounding the colonies are the presumptive endothelial CD31 positive cells. Immunohistochemistry for hCD4 showed that all the cells contained in hepatic colonies expressed foxa2, and that this expression was restricted to the colonies. These results confirmed the endoderm origin of the hepatic colonies.

Similarly, day 12 floating +++ aggregates grew much larger and were processed for immunohistochemistry for AFP and albumin Most of the aggregates were hollow, and cells lining up the aggregates expressed AFP and albumin, while the IgG control section was negative. In addition, AFP and albumin were also stained inside the aggregates, suggesting secretion of both these proteins.

Figure 36A:
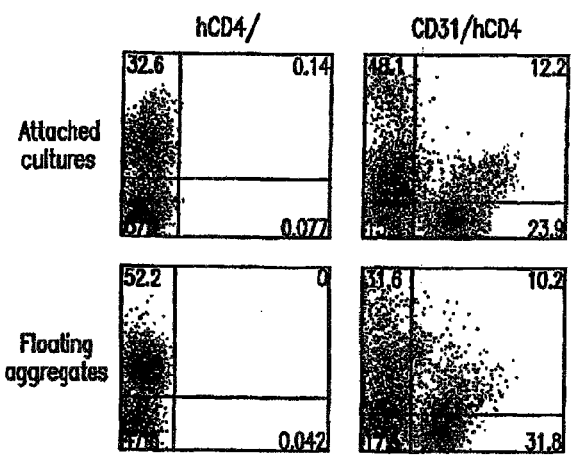
FIGS. 36A, 36B and 36C shows flow cytometry analysis (36A, B) and gene expression analysis (36C) of hepatic colonies.
Figure 36C:
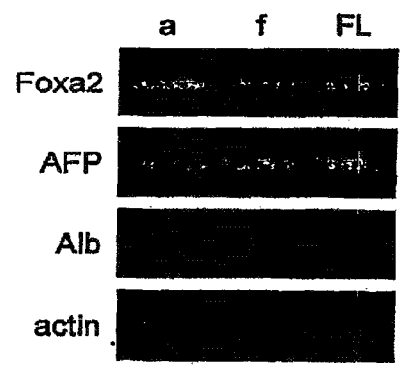
Figure 36B:
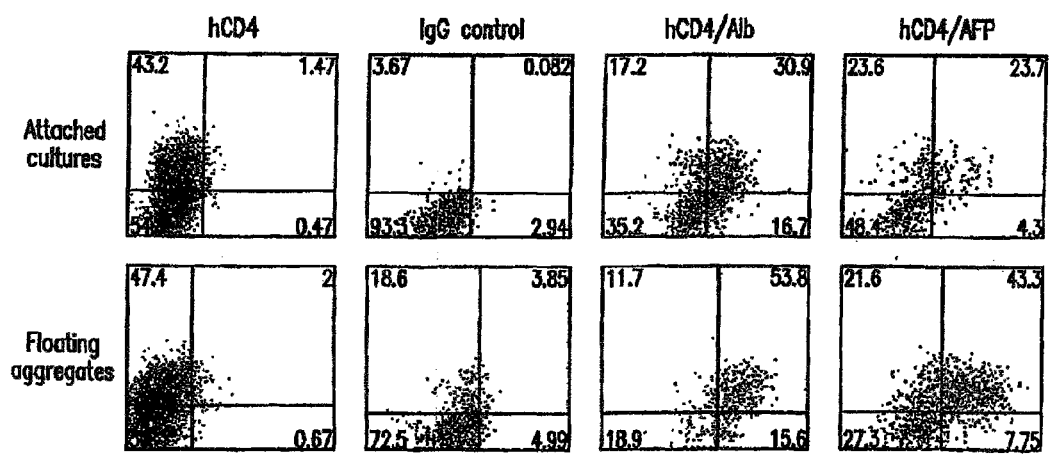

In order to further characterize the day 12 +++ cultures, flow cytometry analysis was performed on both attached cultures and floating aggregates to quantify the endoderm-derived population (hCD4-Foxa2$^+$), endothelial cell population (CD31+ or PECAM-I), hepatoblast/hepatocyte population (hCD4+/alb+, or hCD4+/AFP+) (FIG. 36A, 36B). 30% to 40% of the cells contained in the attached cultures were positive for the endoderm marker hCD4-Foxa2, while 50% were CD31$^+$ endothelial cells. Floating aggregates consisted of a larger (50% to 60%) of hCD4-Foxa2$^+$ cells and a smaller cell population of CD31+ endothelial cells (30%) (FIG. 36A). Most of the hCD4-Foxa2$^+$ cells were also albumin$^+$ and AFP$^+$ assayed by intra-cytoplasmic staining (FIG. 36B). Gene expression analysis by RT-PCR confirmed that the attached cultures (a) as well as the floating aggregates (f) from day 12 +++ cultures expressed foxa2, AFP and albumin (FIG. 36C).

Functional assays were performed to attest the hepatocyte identity. Acid period Schiff Assay indicates in the cytoplasm the presence of glycogen storage that is characteristic of mature hepatocytes. Day 12 +++ attached cultures were stained directly in the dish and showed numerous cells within the colonies containing the typical red cytoplasmic staining for glycogen. Moreover, electro microscopy was performed on day 12 +++ floating aggregates. Most of the cells that lined up the floating aggregates displayed hepatocyte characteristics including a large nucleus/cytoplasmic ration, large amount of glycogen storage and presence of bile canaliculi.

Altogether these data indicate that hepatocytes are generated efficiently from mouse ES cells by mimicking in vitro the developmental progression of the ES cells to an endoderm stage by activin-A induction, a liver specification step with the combination of BMP-4, activinA and bFGF, and finally a proliferation/maturation of the hepatoblast/hepatocyte population

The invention claimed is:

1. A method of making a cell population enriched for hepatocytes comprising the steps of (a) culturing pluripotent stem cells in the presence of activin to induce differentiation into endoderm lineages, (b) further culturing the cells of step (a) in the presence of BMP-4 and bFGF and in the absence of serum to induce differentiation into a hepatic lineage, and (c) culturing the cells from step (b) with one or more cytokines that promote hepatocyte growth to produce a population enriched for hepatocytes.

2. The method of claim 1 wherein the cells are human cells.

3. The method of claim 1 where activin is present at a concentration of about 30 ng/ml to about 100 ng/ml.

4. The method of claim 1 wherein activin is present at a concentration of about 50 ng/ml.

5. The method of claim 1 wherein BMP-4 is present at a concentration of about 10 ng/ml to about 30 ng/ml.

6. The method of claim 1 wherein BMP-4 is present at a concentration of about 30 ng/ml.

7. The method of claim 1 wherein bFGF is present at a concentration of about 1.0 ng/ml to about 10 ng/ml.

8. The method of claim 1 wherein bFGF is present at a concentration of about 10 ng/ml.

9. The method of claim 1 wherein the cytokines are selected from the group consisting of VEGF, human recombinant HGF, EGF, bFGF, and TGFalpha.

10. The method of claim 9 wherein VEGF is present at a concentration of about 10 ng/ml.

11. The method of claim 9 wherein human recombinant HGF is present at a concentration of about 20 ng/ml.

12. The method of claim 9 wherein EGF is present at a concentration of about 10 ng/ml.

13. The method of claim 9 wherein bFGF is present at a concentration of about 10 ng/ml.

14. The method of claim 9 wherein TGFalpha is present at a concentration of about 20 ng/ml.

* * * * *